US006175227B1

(12) United States Patent
Graham et al.

(10) Patent No.: US 6,175,227 B1
(45) Date of Patent: *Jan. 16, 2001

(54) POTENTIAL-SENSING METHOD AND APPARATUS FOR SENSING AND CHARACTERIZING PARTICLES BY THE COULTER PRINCIPLE

(75) Inventors: Marshall D. Graham, Nicholasville, KY (US); Harvey J. Dunstan, Hitchin (GB); Gerry Graham, Nicholasville, KY (US); Ted Britton, Sunrise, FL (US); John Geoffrey Harfield, Harlington (GB); James S. King, Parkland, FL (US)

(73) Assignee: Coulter International Corp., Miami, FL (US)

( * ) Notice: Under 35 U.S.C. 154(b), the term of this patent shall be extended for 0 days.

This patent is subject to a terminal disclaimer.

(21) Appl. No.: 09/108,997

(22) Filed: Jul. 1, 1998

Related U.S. Application Data

(63) Continuation-in-part of application No. 08/887,588, filed on Jul. 3, 1997, now Pat. No. 6,111,398.
(51) Int. Cl.⁷ .................................................. G01N 27/00
(52) U.S. Cl. ...................... 324/71.4; 324/446; 73/61.73; 73/861.41
(58) Field of Search .................................. 324/71.4, 446, 324/450, 693; 73/61.71, 61.73, 149, 861, 861.08, 861.41

(56) References Cited

U.S. PATENT DOCUMENTS

| 2,656,508 | 10/1953 | Coulter . |
| 2,869,078 | 1/1959 | Coulter et al. . |

(List continued on next page.)

OTHER PUBLICATIONS

Thomas, R.A., et al., "Computer–based Electronic Cell Volume Analysis with the AMAC II Transducer", *The Journal of Histochemistry and Cytochemistry,* 22:626–641 Feb. 1974.

(List continued on next page.)

*Primary Examiner*—Glenn W. Brown
(74) *Attorney, Agent, or Firm*—Warren W. Kurz; Mitchell E. Alter

(57) ABSTRACT

A Coulter apparatus comprises a volumeter assembly containing a conduit through which a particle suspension is caused to pass simultaneously with an electrical current. In preferred embodiments the volumeter assembly comprises at least one traditional Coulter conduit wafer, i.e., a dielectric wafer containing a central circular conduit, and at least two electrically conductive collars. The conductive collars approximate the conduit diameter in thickness, are uninsulated, and are attached to opposite sides of the conduit wafer, the openings being congruent with the Coulter conduit. The Coulter conduit in the dielectric wafer and the openings in the conductive collars collectively form a hydrodynamically smooth conduit, in which the electric and hydrodynamic fields of the Coulter conduit are amended. The electric field is shaped to confine the particle-sensitive zone of the novel volumeter conduit within the conduit's physical boundaries, thereby decreasing the zone's coincidence volume. The hydrodynamic field is caused to develop quasi-laminar flow, thereby increasing the proportion of particles per second transiting the zone's electrically homogeneous areas. The conductive collars are provided with electrical connections and also function as electrodes, used either in a passive mode to allow potential-sensing of particle characteristics or in an active mode in response to such particle characteristics. The volumeter assembly substantially eliminates need to compensate for the effects of particles either transiting the sensitive zone on trajectories near the conduit wall or recursing through the exit portion of the particle-sensitive zone.

44 Claims, 16 Drawing Sheets

U.S. PATENT DOCUMENTS

| | | |
|---|---|---|
| 2,985,830 | 5/1961 | Coulter et al. . |
| 3,122,431 | 2/1964 | Coulter et al. . |
| 3,259,842 | 7/1966 | Coulter et al. . |
| 3,299,354 | 1/1967 | Hogg . |
| 3,361,965 | 1/1968 | Coulter et al. . |
| 3,444,463 | 5/1969 | Coulter et al. . |
| 3,502,973 | 3/1970 | Coulter et al. . |
| 3,502,974 | 3/1970 | Coulter et al. . |
| 3,603,875 | 9/1971 | Coulter et al. . |
| 3,628,140 | 12/1971 | Hogg et al. . |
| 3,668,531 | 6/1972 | Hogg . |
| 3,700,867 | 10/1972 | Hogg . |
| 3,701,029 | 10/1972 | Hogg . |
| 3,710,263 | 1/1973 | Doty et al. . |
| 3,710,264 | 1/1973 | Doty et al. . |
| 3,714,565 | 1/1973 | Coulter et al. . |
| 3,739,268 | 6/1973 | Karuhn et al. . |
| 3,746,976 | 7/1973 | Hogg et al. . |
| 3,771,058 | 11/1973 | Hogg . |
| 3,781,674 | 12/1973 | Claps . |
| 3,783,391 | 1/1974 | Hogg et al. . |
| 3,790,883 | 2/1974 | Bergegere . |
| 3,793,587 | 2/1974 | Thom et al. . |
| 3,810,010 | 5/1974 | Thom . |
| 3,863,159 | 1/1975 | Coulter et al. . |
| 3,863,160 | 1/1975 | Doty . |
| 3,871,770 | 3/1975 | von Behrens et al. . |
| 3,902,115 | 8/1975 | Hogg et al. . |
| 3,924,180 | 12/1975 | Salzman et al. . |
| 3,936,739 | 2/1976 | Hogg . |
| 3,940,691 | 2/1976 | Hogg . |
| 3,944,917 | 3/1976 | Hogg et al. . |
| 3,949,197 | 4/1976 | Bader . |
| 3,949,198 | 4/1976 | Coulter et al. . |
| 3,961,249 | 6/1976 | Coulter . |
| 3,963,984 | 6/1976 | Coulter . |
| 3,979,669 | 9/1976 | Godin . |
| 3,987,391 | 10/1976 | Hogg . |
| 4,009,443 | 2/1977 | Coulter et al. . |
| 4,014,611 | 3/1977 | Simpson et al. . |
| 4,019,134 | 4/1977 | Hogg . |
| 4,157,498 | 6/1979 | Johnson . |
| 4,161,690 | 7/1979 | Feier . |
| 4,165,484 | 8/1979 | Haynes . |
| 4,184,766 | 1/1980 | Hogg . |
| 4,220,916 | 9/1980 | Zimmermann et al. . |
| 4,224,567 | 9/1980 | Hoffman . |
| 4,253,058 | 2/1981 | Kachel et al. . |
| 4,290,011 | 9/1981 | Berg et al. . |
| 4,395,676 | 7/1983 | Hollinger et al. . |
| 4,412,175 | 10/1983 | Maynarez . |
| 4,434,398 | 2/1984 | Berg et al. . |
| 4,438,390 | 3/1984 | Hogg . |
| 4,450,435 | 5/1984 | James . |
| 4,484,134 | 11/1984 | Halloran . |
| 4,491,786 | 1/1985 | Godin . |
| 4,510,438 | 4/1985 | Auer . |
| 4,515,274 | 5/1985 | Hollinger et al. . |
| 4,525,666 | 6/1985 | Groves . |
| 4,710,021 | 12/1987 | von Behrens et al. . |
| 4,760,328 | 7/1988 | Groves . |
| 4,775,833 | 10/1988 | Roos et al. . |
| 4,778,657 * | 10/1988 | Spohr ............................... 324/71.4 X |
| 4,791,355 | 12/1988 | Coulter et al. . |
| 4,797,624 | 1/1989 | Dunstan et al. . |
| 4,891,575 * | 1/1990 | Kogo et al. ......................... 324/71.4 |
| 4,972,137 | 11/1990 | Dunstan et al. . |
| 5,125,737 | 6/1992 | Rodriguez et al. . |
| 5,130,639 * | 7/1992 | Hachey ............................... 324/71.4 |
| 5,150,037 | 9/1992 | Kouzuki . |
| 5,402,062 | 3/1995 | Barnes et al. . |
| 5,432,992 | 7/1995 | Barnes et al. . |
| 5,616,501 | 4/1997 | Rodriguez et al. . |
| 5,623,200 | 4/1997 | Ogino . |
| 6,098,471 * | 8/2000 | Berndtsson et al. ................. 73/61.71 |

OTHER PUBLICATIONS

Salzman, G.C., et al., "A Coulter Volume Spectrometer Employing a Potential Sensing Technique", Biophysical Society Abstracts, 17th Annual Meeting, Abstract FPM–F11, *Biophysical Journal,* 13:302a (1973) (month unavailable).

* cited by examiner

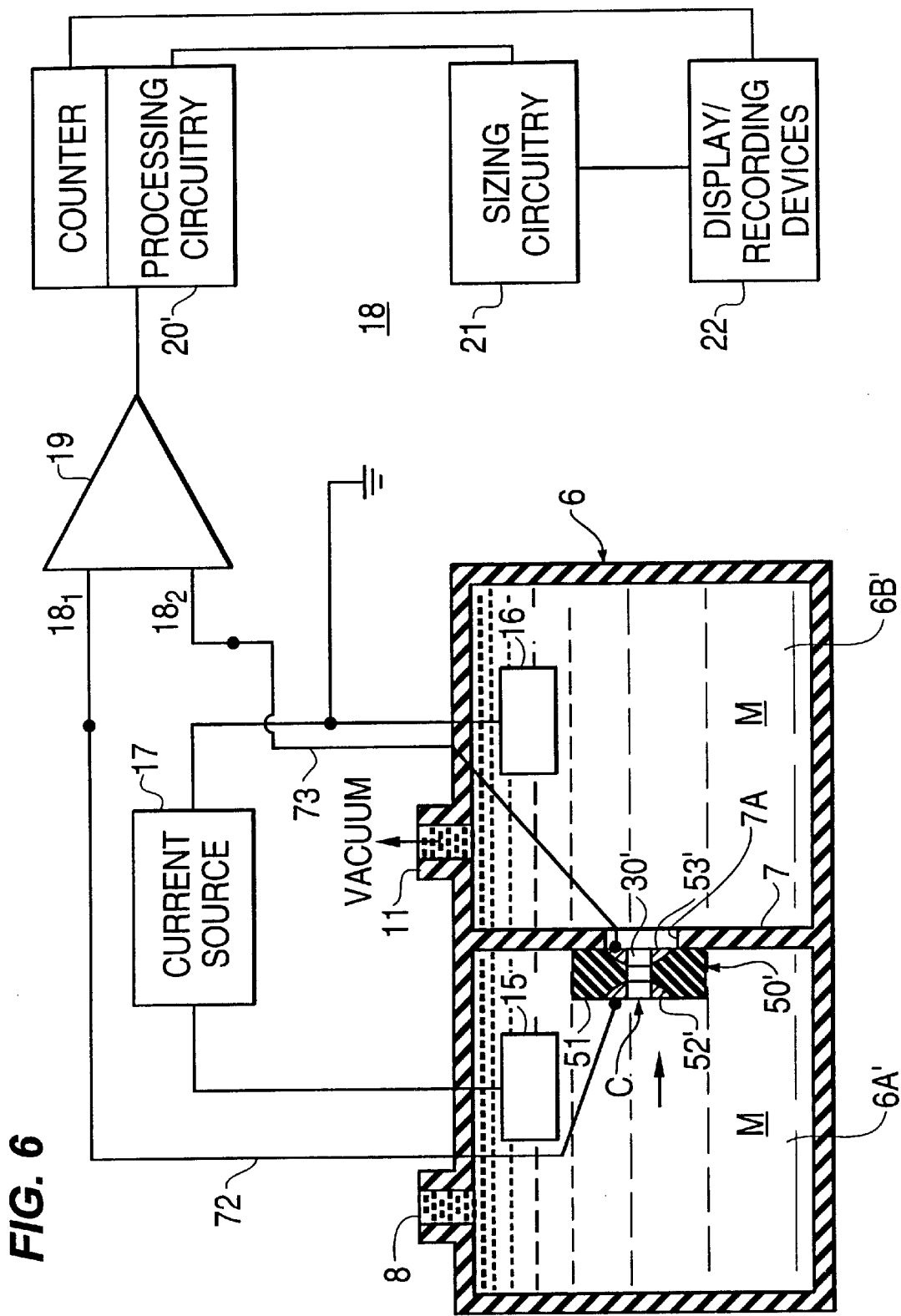

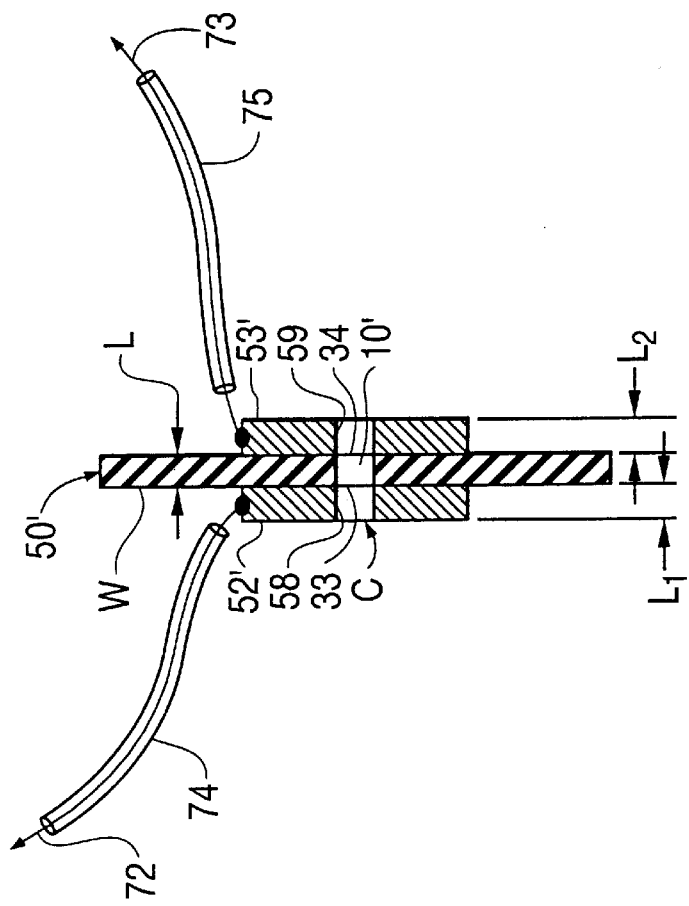
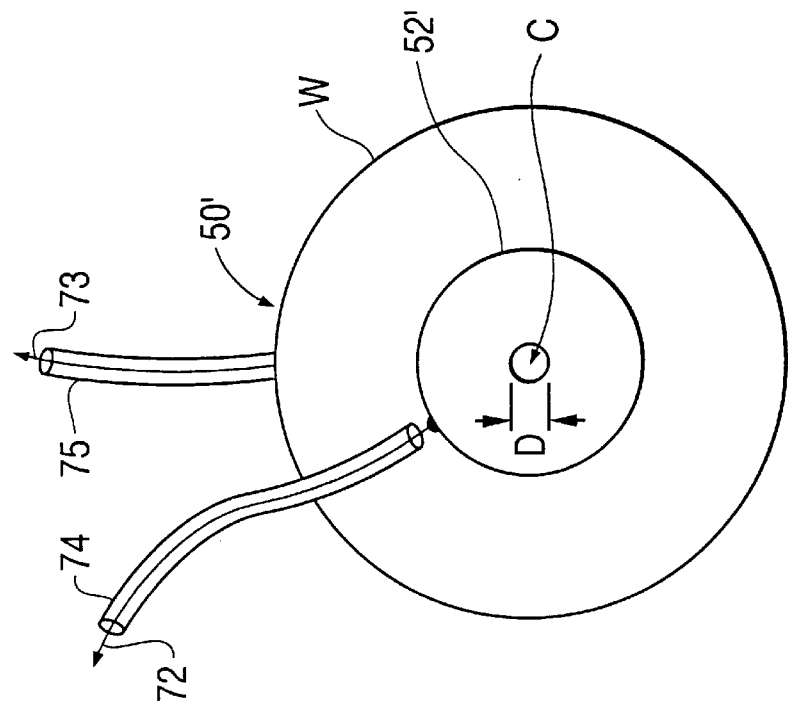

POTENTIAL-SENSING METHOD AND APPARATUS FOR SENSING AND CHARACTERIZING PARTICLES BY THE COULTER PRINCIPLE

REFERENCE TO RELATED APPLICATION

This application is a continuation-in-part of U.S. application Ser. No. 08/887,588 filed on Jul. 3, 1997 now U.S. Pat. No. 6,111,398 and having the title "Method and Apparatus for Sensing and Characterizing Particles" and same assignee.

BACKGROUND OF THE INVENTION

1. Field of the Invention

The present invention relates to improvements in methods and apparatus for sensing and characterizing small particles, such as blood cells or ceramic powders, suspended in a liquid medium having an electrical impedance per unit volume which differs from that of the particles. More particularly, it relates to improvements in methods and apparatus for sensing and characterizing such particles by the Coulter principle.

2. Discussion of the Prior Art

U.S. Pat. No. 2,656,508 to Wallace H. Coulter discloses a seminal method for sensing particles suspended in a liquid medium. An exemplary apparatus for implementing such method comprises a dual-compartment dielectric vessel which defines first and second compartments separated by a dielectric wall. Each of the compartments is adapted to contain, and is filled with, a liquid medium. The particles to be sensed and characterized are suspended at an appropriate concentration in the liquid medium and introduced into one compartment through a suitable inlet port formed therein. The separating wall is provided with a relatively large opening which is sealed by a thin wafer made of a homogeneous dielectric material. A small through-hole formed in the wafer provides a conduit, which constitutes the only operative connection between the two compartments. An appropriate vacuum applied to an outlet port suitably formed in the second compartment causes the particle suspension to flow from the first compartment to the second compartment through said conduit, discussed in detail below. Each particle in the suspension displaces its own volume of the particle-suspending liquid, and the conduit provides a consistent reference volume against which that displaced volume may be compared. If the dimensions of the conduit and the concentration of particles in the suspension are appropriately selected, particles can be made to transit the conduit more or less individually. The conduit thus functions as a miniature volumeter, capable under suitable conditions of making sensible the liquid displaced by individual microscopic particles.

To enable convenient sensing of the liquid displacement occasioned by particles transiting the conduit, the particle-suspending liquid is made to have an electrical impedance per unit volume which differs from that of the particles. The contrast in electrical impedance between particle and suspending liquid thus converts the volume of displaced liquid into a proportional change in the electrical impedance of the liquid column filling the conduit. An excitation electrode is positioned in each of the two compartments and operatively connected to a source of electrical current, whereby a nominal electrical current (the excitation current) is caused to flow through the conduit simultaneously with the particle suspension. Consequently, passage of a particle through the conduit produces a pulsation in the current flowing through the conduit which is proportional to the volume of liquid displaced by the particle. An extensive art has developed whereby such particle pulsations may be sensed and monitored to provide particle-characterization information. This art has taken two forms, the first based on the original two-terminal sensing approach described in the '508 patent and the second based on four-terminal, potential-sensing approaches. The second form of Coulter art evolved from the first and shares similar limitations; both forms will be discussed.

In the '508 patent the excitation current is applied from a voltage source through the two electrodes immersed in the suspending liquid of the two compartments interconnected by the conduit. An AC-coupled sensing circuit, also operatively connected to the excitation electrodes, operates to sense the pulsations in current between these electrodes. Thus, as individual particles pass through the conduit, said sensing circuit produces an electrical signal pulse having an amplitude which is characteristic of the particle volume. Additional circuits further process the particle signal pulses to provide a count of particles exceeding some particular volumetric threshold or, via the elegant positive-displacement metering system disclosed in U.S. Pat. No. 2,869,078 to Wallace H. Coulter and Joseph R. Coulter, Jr., the particle concentration. The volumetric distribution of the particles may be conveniently characterized by causing the current source to provide a constant current and analyzing the particle pulses with multiple-thresholding sizing circuitry as described in U.S. Pat. No. 3,259,842 to Wallace H. Coulter et al. Alternatively, if the current source is caused to provide combinations of electrode excitation, including at least one source of high-frequency alternating current as discussed in U.S. Pat. Nos. 3,502,973 and 3,502,974 to Wallace H. Coulter and W. R. Hogg, an apparent volume reflecting the internal composition of certain particles may be similarly characterized. Such characterization results are displayed or recorded by appropriate devices. This method of sensing and characterizing particles, by suspending them in a liquid medium having an electrical impedance per unit volume which differs from that of the particles and passing the resulting particle suspension through a constricting conduit while monitoring the electrical current flow through the conduit, has become known as the Coulter principle. Because of their simplicity, the two-terminal sensing methods were the only ones in use for many years and still see exclusive use in commercially available apparatus incorporating the Coulter principle.

Central to the Coulter principle is the volumeter conduit which enables electrical sensing of particle characteristics by constricting both the electric and hydrodynamic fields established in the dual-compartment vessel. Due to their excellent dielectric and mechanical properties, ruby or sapphire jewels developed as antifriction bearings for precision mechanical devices were indicated for use as conduit wafers in U.S. Pat. Nos. 2,985,830 and 3,122,431 to Wallace H. Coulter et al. As shown in the enlarged longitudinal section of a traditional Coulter conduit wafer W in FIG. 1, a Coulter volumeter conduit comprises a continuous surface or wall 30 of length L which defines a right cylindrical opening of circular cross-section and diameter D through a homogeneous dielectric material of thickness L. (Conduit wafer W is often called an "aperture wafer", and volumeter conduit 10 in conduit wafer W is commonly referred to as a "Coulter aperture".) Due to material homogeneity, the electrical resistivity of conduit wall 30 surrounding the flows of particle suspension and current through the conduit is substantially axisymmetric and uniform in any longitudinal conduit section.

In practice, FIG. 1 conduit diameter D must approach twice the maximum particle diameter to minimize risk of clogging, and conduit length L is usually made as short as possible to minimize coincidence artifacts due to two or more particles simultaneously transiting the conduit. For many medical and scientific applications, conduit diameter D ranges between approximately 0.030 mm and 0.200 mm, and the conduit length-to-diameter ratio UD ranges between 0.75 to 1.2. With these small conduits, physical clogging may limit application, especially to samples of biological origin, while their limited dynamic range in particle size may limit application where polydisperse industrial samples are involved. Critical applications can benefit from splitting such samples through a plurality of conduits and appropriately processing the multiple data streams. Parallel-conduit systems typically comprise a single entry compartment containing a first electrode, but provide each conduit with an electrically isolated exit compartment containing an individual second electrode, with all conduits being simultaneously transited by parcel streams split from the sample suspension in the entry compartment. As taught by Wallace H. Coulter and W. R. Hogg, the several conduits may be either of identical geometry (U.S. Pat. No. 3,444,483) or of dissimilar geometry (U.S. Pat. No. 3,603,875). Each conduit independently generates pulse data for the particles in its portion of the split sample. In the first case voting logic may be used to eliminate from the redundant particle data any data originating in a clogged conduit, while in the second, pulse-analytic circuitry may be used to process the dissimilar data into a composite volumetric distribution for polydisperse samples. Such parallel-conduit systems are fundamentally combined duplicated forms of the '508 apparatus, modified to appropriately handle the multiple pulse-data streams.

Of interest are the functional characteristics of Coulter volumeter conduits such as 10 in FIG. 1 and the prior art which has been developed to facilitate application of such conduits in practical instruments for particle characterization. In the related patent application the characteristics, limitations, and facilitating art of the Coulter conduit have been given a comprehensive review, which is herein incorporated in its entirety by reference. Significant conduit characteristics include: 1) Those defining the conduit sensitive zone Z; 2) Those explaining anomalous pulses generated by particles transiting sensitive zone Z on wall trajectories; and 3) Those explaining extraneous pulses generated by exiting particles recirculating into the exit ambit of sensitive zone Z. For convenience, relevant points of specific interest to the present application may be summarized from said review as follows:

1. As shown in FIG. 1, the partice-sensitive zone Z functionally includes not only the geometric volumeter conduit 10 defined by wall 30 but also the two semielliptical ambit electric fields 31 and 32 coaxial with, and outside the opposing ends of, the geometric conduit; the scale of these ambit fields depends only on the diameter D of the respective entrance and exit orifices, 33 and 34. In addition to producing current pulsations as they transit the geometric conduit, particles may also produce current pulsations if they pass through that portion of the suspending liquid containing the ambit fields. Consequently, the semielliptical equipotentials corresponding to the desired detectability threshold determine the effective spatial extent of the ambit fields 31 and 32. It has been demonstrated that the effective ambit feeds extend outward from the respective entrance and exit orifices 33 and 34 of volumeter conduit 10 approximately one conduit diameter D, with lateral intercepts at 1.15D, if pulse amplitudes from peripheral passages are to be limited to one percent of the theoretical maximum signal-pulse amplitude. For these one-percent equipotentials 35 and 36, the axial length of sensitive zone Z is (L+2D), and for UD=1.2 more than 85 percent of the particle-sensitive zone can be shown to be external to the geometric Coulter conduit 10. The spatial extent of sensitive zone Z increases the likelihood of particle coincidence, requiring greater sample dilution and processing times. Particle coincidence degrades count data directly through lost particle pulses. It also degrades volumetric data indirectly through inappropriate inclusion of misshapen pulses in the volumetric distribution. Adaptive dilution may acceptably limit coincidence artifact (U.S. Pat. No. 3,979,669 to T. J. Godin), or adaptive extension of the counting period may acceptably compensate it (U.S. Pat. No. 4,009,443 to Wallace H. Coulter et al.); but the resulting variable processing times are undesirable in many applications. In principle, the pulse loss due to coincidence can be predicted statistically, and many postcollection corrective techniques have been described in the scientific and patent literature; see, e.g., U.S. Pat. No. 3,949,197 to H. Bader for a review and example. Other approaches estimate pulse loss based on pulse occurrence rate, count, or duration, e.g., U.S. Pat. No. 3,790,883 to P. Bergegere; U.S. Pat. Nos. 3,936,739 and 3,940,691 to W. R. Hogg; U.S. Pat. No. 3,949,198 to Wallace H. Coulter and W. R. Hogg; and U.S. Pat. No. 3,987,391 to W. R. Hogg. Limitations of several are discussed in U.S. Pat. No. 4,510,438 to R. Auer, which proposes correction for the actual coincidence rate as determined by an independent optical sensing modality. These methods may acceptably correct count data for coincidence pulse loss when automated for specific applications, but only those which inhibit incorporation of misshapen pulses can improve the population volumetric distribution.

In addition to coincidence effects, the spatial extent of sensitive zone Z limits pulse signal-to-noise ratios, and therefore particle detectability, in two ways. First, particle contrasts and so pulse amplitudes are limited, since the volumetric sensitivity depends on the ratio of liquid volume displaced by each particle to the volume of liquid in the sensitive zone; and secondly, the noise tending to mask particle contrasts is increased, since it originates thermally throughout this latter volume. Noise originates by two mechanisms, heating noise resulting from dissipation of the excitation current in the resistance of the particle-sensitive zone, and Johnson noise generated in this resistance. These limit the maximum practicable excitation current, on the one hand, and fundamental particle detectability on the other. In the prior art, heating noise has been reduced by providing thermally conductive paths leading away from conduit 10. U.S. Pat. No. 3,361,965 to Wallce H. Coulter and Joseph R. Coulter, Jr., describes one such structure, in which one electrode is formed as a plated metallic coating on the outer surface of a tube closed except for conduit 10 in wafer W. In U.S. Pat. No. 3,714,565 to Wallace H. Coulter and W. R. Hogg the electrical path length through the suspending liquid, and so the thermal noise, is reduced by replacing the second electrode with a metallic element either composing, or coated onto the inner surface of, the tube wall. The thermal effects are described more fully in U.S. Pat. No. 3,771,058 to W. R. Hogg; here, volumeter conduit 10 is formed in a wafer of thermally conductive dielectric and thermally connected to remote cooler regions via electrically and thermally conductive metallic coatings extending onto both planar surfaces of the conduit wafer. In U.S. Pat. No. 4,760,328 the same geometry is described in a structure which integrates sensing electronics onto the sapphire wafer. In all four of these patents the conductors cover extensive areas of the structure and variously approach volumeter conduit 10, but do not extend so close to the conduit as to interact with the effective ambit fields of its particle-sensitive zone Z. However, in U.S. Pat. No. 3,924,180 the Coulter conduit structure is modified by incorporation of thin conductors into the conduit structure, contiguous to conduit orifices 33 and 34, so forming potential-sensing electrodes in a dielectric sandwich through which the conduit penetrates; the intent is to minimize noise contributions to the sensed particle signal from the liquid outside the conduit ambits 31 and 32. Other techniques attempt to minimize noise effects, as for example the noise discriminator described in U.S. Pat. No. 3,781,674 to W. A. Claps, or the averaging of signals from tandem conduit/electrode structures similar to those of aforementioned U.S. Pat. No. 3,924,180 to reduce Johnson noise as described in U.S. Pat. No. 4,438,390 to W. R. Hogg. In critical applications, certain of these may reduce heating noise generated in the conduit, but none significantly improves the volumetric sensitivity. U.S. Pat. Nos. 3,924,180 and 4,438,390 are the subject of further discussion, to follow.

In principle, shorter conduit lengths L can decrease particle coincidence, increase conduit volumetric sensitivity, and decrease thermal noise; in practice, the benefits of decreasing conduit length are limited because, as L approaches zero, sensitive zone Z collapses to the ambit ellipsoid with volume determined by the conduit diameter and the desired threshold of pulse detectability. As indicated in discussion to follow, axial homogeneity of the electric field inside the geometric portion of sensitive zone Z also decreases with decreasing L, and the amplitude of pulses generated by particles transiting conduit 10 correspondingly decreases, with attendant reduction in pulse signal-to-noise ratio.

2. In volumetric applications of Coulter volumeter conduits, the most significant hydrodynamic effects are those on particle trajectory, shape, and orientation during passage through sensitive zone Z. In response to the driving pressure gradient, particles P in the sample compartment are entrained in a developing concentric flow and accelerated toward the entry orifice 33 of volumeter conduit 10. At the entry orifice 33 in FIG. 1, the velocity profile of the constricting flow is quasi-uniform and of a magnitude determined by the desired sample volume, the time allowed to process it, and the cross-sectional area of the conduit The flow just inside the conduit includes a shear layer at conduit wall 30, and particularly for L/D ratios less than about 3.0, the flow profile depends on the edge sharpness of entry orifice 33 and on how closely the kinematic viscosity of the suspending liquid permits it to follow the orifice geometry (for practical reasons, orifice edges are usually sharp, and the shear layer surrounding the developing laminar flow may thicken to appreciably constrict the apparent flow cross-section). When curvature of the edge at orifice 33 is sufficiently gradual, viscosity causes a transition from a quasi-uniform velocity profile toward the parabolic velocity profile of laminar flow. As has been noted, the sensitive zone Z extends outward about one conduit diameter D from the entry orifice 33 in FIG. 1 and is thus overlapped by the convergent flow into conduit 10. The electric field forming that portion of particle-sensitive zone Z within the geometric volumeter conduit 10 is inhomogeneous, only approaching homogeneity at the conduit midpoint for L/D ratios of 2.0 or greater. As a result of the midpoint field inhomogeneity, particles transiting conduit 10 along axial trajectories fail to generate fully-developed pulse amplitudes for conduits with L/D ratios less than 2.5; in addition, particles with similar contrasts generate pulse amplitudes depending on the radial position of the particle trajectory, particularly near wall 30, regardless of the L/D ratio of the conduit As they enter the entry ambit 31 of the sensitive zone, particles on near-axial trajectories (e.g., trajectory $A_T$) may be deformed by the pressure field, and non-spherical particles will be oriented with their long dimension parallel to flow; such particles generate Gaussian-shaped pulses. Particles entering the sensitive zone outside an axial cone approximately 50 degrees in half-angle will, in addition, be accelerated around the edge at orifice 33 and through the conduit in the annulus near wall 30 containing intense orifice gradients. These orifice gradients cause particles on trajectories such as $B_T$ in FIG. 1 to generate M-shaped pulses of anomalous amplitude and duration due to gradients in, respectively, conduit field and liquid flow. Particles on an intermediate trajectory such as $C_T$ may generate asymmetric pulses, which demonstrate anomalous amplitude only on their leading edge. Due to their anomalous pulse amplitudes, particles following near-wall trajectories (e.g., $B_T$ and $C_T$ in FIG. 1) introduce artifactual high-volume skewness into the sample volumetric distribution, so degrading system ability to resolve particles of nearly identical volumes. The frequency of such pulses depends on the average radial position of the modal trajectories, which in turn is determined by the length L of the conduit, and the portion of the conduit cross section occupied by the orifice gradients. This region, from conduit wall 30 inward to a radius $r=0.75(D/2)$ for typical Coulter volumeter conduits, also defines the maximum particle diameter for which linear volumetric response is obtained. Conduits with L/D=3.3 have been shown to reduce skewness inaccuracies; then, exit modal trajectories are centered inside $r=0.66(D/2)$.

The characteristic M-shaped pulses produced by particles transiting volumeter conduit 10 on trajectories such as $B_T$ or $C_T$ introduce artifacts into the volumetric distribution, the importance of which is attested by the large amount of remedial prior art addressing them. This art is divided between two approaches, the early post-collection one of excluding M-shaped pulses from the processed data and the later direct one of hydrodynamically controlling presentation of particles to the sensitive zone of the conduit. Deletion of such pulses from the volumetric distribution data is suggested in U.S. Pat. No. 3,668,531 to W. R. Hogg, from which FIG. 1 is adapted. Other approaches have been described (U.S. Pat. Nos. 3,700,867 and 3,701,029 to W. R. Hogg; U.S. Pat. Nos. 3,710,263 and 3,710,264 to E. N. Doty and W. R. Hogg; U.S. Pat. No. 3,783,391 to W. R. Hogg and Wallace H. Coulter; U.S. Pat. No. 3,863,160 to E. N. Doty; and U.S. Pat. No. 3,961,249 to Wallce H. Coulter), all of which incorporate gating circuitry responsive to various anomalous parameters of the misshapen pulses by which these pulses may be deleted from the pulse train processed for population distributions. Some of these are discussed in U.S. Pat. No. 3,863,159 to Wallace H. Coulter and E. N. Doty and in U.S. Pat. No. 4,797,624 to H. J. Dunstan et al., either of which well illustrates such gating methods. Gating may also be done in response to a detection signal from an auxiliary electrode (U.S. Pat. No. 4,161,690). The complexity of working implementations encouraged other approaches, and a simple flow-aligning device in front of the Coulter conduit was shown to improve volumetric accuracy (U.S. Pat. Nos. 3,739,268; 4,290,011; and 4,434,398). Further improvement was gained by injecting the particle stream directly into the conduit through an auxiliary flow director (U.S. Pat. No. 3,793,587 to R. Thom and J. Schulz and U.S. Pat. No. 3,810,010 to R. Thom), a technique now known as hydrodynamically focused flow. If the particle suspension is introduced through the flow director while additional liquid medium is appropriately metered through a port in the entry compartment of the dual-compartment vessel, the particles entering this compartment will be entrained into a sheath of the liquid medium and carried through conduit 10 in the core of the composite flow pattern, with two important consequences. Firstly, the directed flow pattern prevents particles entering conduit 10 on trajectories such as $B_T$ and $C_T$ in FIG. 1, thereby eliminating M-shaped pulses. Secondly, all particles transit conduit 10 inside the sheath liquid, which serves to center the particle trajectories inside the cross section of conduit 10 having relatively homogeneous electric fields, further reducing occurrence of anomalous particle pulses. Numerous conduit subassemblies incorporating focused flow have been described (e.g., U.S. Pat. No. 4,014,611 to R. O. Simpson and T. J. Godin; U.S. Pat. No. 4,395,676 to J. D. Hollinger and W. R. Hogg; U.S. Pat. No. 4,484,134 to M. T. Halloran; U.S. Pat. No. 4,515,274 to J. D. Hollinger and R. I. Pedroso; and U.S. Pat. No. 4,525,666 to M. R. Groves; U.S. Pat. Nos. 3,871,770; 4,165,484; 4,253,058; 4,760,328; 5,150,037; and 5,623,200), some of which also include provisions addressing recirculating particles and the best of which can yield nearly ideal volumetric distributions. All add complexity to practical apparatus, and the large fluid volumes required for effective sample focusing make it impractical to volumetrically determine particle concentration by positive-displacement methods. Because the entraining sheath flow restricts the sample stream to a small central portion of the geometric volumeter conduit, a functional concentration of particles within this volume occurs and limitation of coincidence effects typically requires use of lower particle concentrations than with unfocused systems.

3. Regardless of the sharpness of the edge of the entry orifice 33 in FIG. 1, flow at the exit orifice 34 is jetting flow, with a toroidal low-pressure region surrounding the jet and overlapping the exit ambit field 32. For particles exiting orifice 34, the modal trajectories occur in annuli centered at radii r=0.82(D/2) or 0.76(D/2) for conduits with L/D=0.75 or 1.20, respectively, and significant numbers of particles transit the conduit outside r=0.75(D/2), through the orifice gradients of the sensitive zone. The combination of a sharp edge at orifice 33 and the low L/D ratios of typical volunteer conduits also minimizes the stabilizing effect of viscosity, and as a consequence, both the through-flow and jetting patterns are sensitive to imperfections in the edge of entry orifice 33. Conduit L/D ratios of 2.0 or greater result in both smoother flow through the geometric volumeter conduit and less turbulence in the jetting zone outside the exit orifice; exit modal trajectories for such conduits are centered inside r=0.725(D/2). Decelerating particles that have exited the geometric volumeter conduit 10 may be drawn back into the exit ambit 32 (e.g., trajectory $D_T$ in FIG. 1) as the suspending liquid recirculates into the toroidal low-pressure region surrounding the exit jet; if so, they generate extraneous pulses of low amplitude and long duration. Recirculation trajectories also have adverse consequences significant in many applications of the Coulter principle. In contrast to an ideal volumetric distribution, the recirculating particles (e.g., trajectory $D_T$ in FIG. 1) result in a secondary low-volume distribution in the actual sample distribution; this spurious distribution reduces dynamic volumetric range and, for polydisperse samples, may altogether preclude analysis of the smaller particles.

At cost of reduced sample throughput, recirculation pulses may be excluded by pulse gating, either through analysis of pulses from the standard conduit or in response to a thin auxiliary detection electrode located in the conduit's geometric cylinder (aforementioned U.S. Pat. No. 4,161,690). Longitudinal conduit profiles can mechanically reduce the liquid volume available to such particles and may be beneficial in some applications, as noted in U.S. Pat. No. 3,628,140 to W. R. Hogg and Wallace H. Coulter. Other applications are more critical, and many subassemblies incorporating the volumeter conduit have been described which attempt to prevent particles from recirculating into the conduit ambit fields. These either structure the exit flow path so that particles are mechanically prevented from re-entering the sensitive zone (U.S. Pat. Nos. 3,299,354 and 3,746,976 to W. R. Hogg or U.S. Pat. No. 4,484,134 to M. T. Halloran), use auxiliary fluidic circuits to dynamically sweep exiting particles away from the exit orifice (U.S. Pat. No. 4,014,611 to R. O. Simpson and T. J. Godin) or combine these two approaches (U.S. Pat. No. 3,902,115 to W. R. Hogg et al. and U.S. Pat. No. 4,491,786 to T. J. Godin, which contains a review of such methods). Several other implementations have also been described (U.S. Pat. Nos. 4,253,058; 4,290,011; 4,434,398; 4,710,021; 5,402,062; 5,432,992; and 5,623,200). The dynamic sweep-flow method is widely used and involves metering appropriate volumes of the liquid medium through a second inlet port in the exit compartment of the dual-compartment vessel, whereby the particles exiting conduit 10 are swept out of exit ambit field 32. These complex subassemblies can essentially eliminate recirculating particles, may include shaped conduits, and often include additional structure addressing effects of particles following wall trajectories. However, all add complexity to practical apparatus, and the large fluid volumes required for effective sweep-flow make it impractical to volumetrically determine particle concentration by positive disablement methods. An approach due to M. T. Halloran (in aforementioned U.S. Pat. No. 4,484,134) potentially avoids need for auxiliary fluidic circuits and structures, by extending the insulating discs of aforementioned U.S. Pat. No. 3,924,180; of an inner diameter substantially equal to that of the volumeter conduit, such extensions mechanically prevent recirculation of exiting particles into the exit ambit of the conduit and when carefully constructed can provide hydrodynamic advantages of long conduits. However, for many applications of the Coulter principle such structures require complex mechanical designs difficult to implement and which tend to clog in use.

In the invention of the related application, electric and hydrodynamic fields in the vicinity of the two-terminal volumeter conduit are directly amended, whereby the need for dynamic sweep flow is avoided and the need for hydrodynamically focused low is minimized. In addition the coincidence volume of the said field-amending conduit is about 30 percent of that of the Coulter conduit used in the apparatus of the '508 and '328 patents, for geometric conduits of the same configuration and dimensions. Consequently, many of the inaccuracies encountered with the prior-art apparatus is avoided, so eliminating much complexity in apparatus make up. Prior-art two-terminal apparatus of the '508 type, containing none of the aforementioned facilitating art, provided substantially ideal volumetric measurements when the new field-amending volunteer assembly was substituted for the wafer W comprising the FIG. 1 conduit.

Maximum particle-pulse amplitudes are obtained with a given Coulter volumeter conduit when used with the greatest excitation current compatible with generation of acceptable thermal artifacts in the liquid column within the conduit, but practicable current densities may be limited in biological applications to ones incapable of causing breakdown of cell membranes. To minimize artifacts due to electrochemical effects such as polarization and generation of gas bubbles, large-area electrodes located well away from the sensitive zone Z of conduit 10 are preferred. The capacitance of typical electrodes acts to limit rise times and fall times of potential changes between the electrodes, whether these be due to particles transiting the sensitive zone of the conduit or ramping the aperture current so that cellular internal conductivity may be determined, viz., U.S. Pat. No. 4,220,916. Although some two-terminal conduit structures incorporated comparatively small electrodes (e.g., U.S. Pat. No. 4,157,498; aforementioned U.S. Pat. No. 3,361,965 to Wallace H. Coulter and Joseph R. Coulter, Jr.; U.S. Pat. No. 3,714,565 to Wallace H. Coulter and W. R. Hogg; U.S. Pat. No. 3,771,058 to W. R. Hogg; or U.S. Pat. No. 4,760,328), these electrodes only approached the volumeter conduit and did not extend into the ambit electric fields 31 or 32 of its sensitive zone, to limit electrochemical artifacts. However, aforementioned U.S. Pat. Nos. 4,290,011 and 4,434,398 describe an elongate conduit which incorporates at its entry orifice one of the two excitation/sensing electrodes as a ring encircling, and in electrical contact with, the conduit flow stream. In addition, U.S. Pat. No. 4,224,567 and aforementioned U.S. Pat. No. 4,484,134 describe similar elongate structures incorporating two thin excitation/sensing electrodes, each surrounding the suspension stream at an orifice of the functional Coulter conduit. (As indicated in the latter patent, control of electrochemical artifacts may require use of auxiliary excitation electrodes, located in remote vessels and connected to the orifice electrodes via channels filled with suspending medium.) These structures are complex, tend to clog, and have received little application.

Substitution of a conduit of different geometry or changes in resistivity of the suspending medium may affect the excitation current density in the conduit; in U.S. Pat. No. 3,944,917 to W. R. Hogg et al. a set of auxiliary sensing electrodes, located in the suspending medium near the conduit orifices, provides a control signal which enables compensation of the excitation current applied to the excitation electrodes for resultant changes in resistance of the liquid column within the conduit. Controlling the diversion of excitation current through the fluidic subsystem requires a means of isolating the conduit from the remainder of this system, and other four-terminal art can achieve this through active means, by which auxiliary control electrodes are driven by a bootstrap circuit, viz., U.S. Pat. No. 4,972,137 to H. J. Dunstan and I. D. Gilbert. Additional examples are known of similar four-terminal art, but all suffer more or less indeterminate electrode placement relative to the conduit. In some desirable applications of such art the result is an unacceptable degradation in the dynamic characteristics of the operational mechanism.

In the 1970s it was recognized that if no current were passed through independent electrodes (i.e., the electrodes are potential sensing rather than current sensing) such electrodes could then be both compactly designed and advantageously fixed near the conduit orifices, thereby reducing electrode capacitance, pulse rise times, and locational uncertainty. Such four-terminal sensing art developed around two distinct approaches, one by Leif and another by Salzman, both using high-impedance sensing circuits. Both approaches also contain the volumeter conduit within a stacked five-layer assembly, each of the four outer layers including an opening coaxially aligned with the functional Coulter conduit through the central layer. However, functional properties of the two resulting sensitive zones differ appreciably, due to structural differences in the two five-layer assemblies.

In the Leif structure, potential-sensing electrodes are located near, but not in, the sensitive zone of a conventional Coulter conduit. The most relevant example is described by R. A. Thomas, B. F. Cameron, and R. C. Leif [Computer-based electronic cell volume analysis with the AMAC II transducer, *The Journal of Histochemistry and Cytochemistry*, 22:626–641, 19741]. This example (12 in FIG. 2) comprises thick platinum potential-sensing electrodes 13 and 14, each separated from a conventional Coulter conduit wafer W by a circular insulating spacing-element 23 or 24. The individual components 13, 14, 23, and 24 are several tens of times the diameter of volumeter conduit 10' (D=0.100 mm, L/D=1.0), and each contains a central circular opening 25, 28, 26, or 27, respectively, of diameter 0.010" (0.254 mm or approximately 2.5D) aligned coaxially with the smaller Coulter conduit 10' during assembly. The thickness of each electrode 13 and 14 and each spacing-element 23 and 24 is also 0.010". In use, conduit 10' and combined openings 25/26 and 27128 in each electrode/spacing-element couple 13/23 and 24/14, respectively, form a fluid-filled channel interconnecting the two compartments of the dielectric vessel containing the suspending liquid in which excitation electrodes are immersed. Sensing electrodes 13 and 14 are in electrical contact with the suspending medium carrying the particles through said channel and are operatively connected to high-impedance sensing circuits, so that no significant current flows between them.

As for the conventional Coulter conduit 10 in FIG. 1, characteristics of the electric and hydrodynamic fields within volunteer conduit 10' of FIG. 2 Leif structure 12 are co-determined, and within the fluid-filled channel surrounded by wall 30 the electric flow established by the current between the excitation electrodes is inhomogeneous. As indicated in FIG. 2, in and near Coulter conduit 10' the field distribution is similar to that for conduit 10 of the Coulter wafer W used conventionally, as in FIG. 1. Particles P carried through the FIG. 2 sensitive zone $Z_L$ by coaxial hydrodynamically focused flow (e.g., on trajectory $A_T$) produce particle pulses having improved rise times when sensed between electrodes 13 and 14. When the flow director is positioned off the conduit axis so that particles transit conduit 10' on off-axis trajectories such as $B_T'$, anomalous pulses result similar to those seen for particles on trajectory $B_T$ in FIG. 1; the frequency of such pulses (and therefore the severity of resultant skewness the volumetric histogram) increases as the flow director is positioned to cause near-wall trajectories, thus demonstrating orifice and wall gradients in the Leif structure comparable to those encountered when Coulter wafer W is used conventionally.

As also indicated in FIG. 2, the one-percent equipotentials 35' and 36' of the ambit fields delimiting sensitive zone $Z_L$ do not directly approach sensing electrodes 13 and 14. In comparison with sensitive zone Z in FIG. 1, the primary coincidence volume contained between the one-percent equipotentials 35' and 36' is of similar axial extent, but somewhat flattened and curtailed laterally by the inner wall of openings 26 and 27. Consequently, the primary coincidence volume of Coulter wafer W when used in Leif structure 12 is somewhat smaller than when used conventionally. However, while the field distribution in and near Coulter conduit 10' in FIG. 2 is similar to that for the conventional Coulter wafer W of FIG. 1, it is superimposed on a lower-gradient field distribution (not shown) due to the impedance of the liquid columns within openings 26 and 27 in spacing-elements 23 and 24. Therefore, both the excitation electrodes and the sensing electrodes 13 and 14 respond to impedance changes in the liquid columns within these openings as well as in sensitive zone $Z_L$, and pulses generated by single particles consist of a substantially conventional pulse generated during passage through sensitive zone $Z_L$. However, such particle pulses are superimposed on a low-amplitude pedestal originating in the field gradient along these fluid columns in openings 26 and 27. If two particles simultaneously occupy positions within any responsive portion of the total fluid channel, the resultant pulse amplitude will be artifactual for both particles. Consequently, conduit 10' of Leif structure 12 has a secondary coincidence volume which does not exist for the FIG. 1 Coulter volumeter conduit 10, and this secondary coincidence volume is considerably larger than the primary coincidence volume, particularly when particle pulses are sensed between the excitation electrodes. The compound nature of the individual particle pulses generated by Leif structure 12 and the attendant secondary coincidence volume both tend to complicate analysis of the particle pulses.

In operation, convergent fluidic flow begins developing outside the entry to opening 25 in electrode 13 of Leif structure 12, with a further convergent transition at the entry to conduit 10'. Thus, the combined thicknesses of electrode 13 and spacing-element 23 act to straighten trajectories of particles entering the sensitive zone $Z_L$ so that the frequency of particles on trajectories such as $B_T$ or (particularly) $C_T$ in FIG. 1 is reduced, together with the number of resulting anomalous particle pulses. However, a significant number of particles may still transit the FIG. 2 conduit 10' on near-wall trajectories similar to $B_T$', with resultant anomalous pulses, unless hydrodynamically focused-flow methods are used.

Thicknesses of insulating spacing-element 24 and electrode 14 in Leif structure 12 similarly reduce availability of the sensitive zone to particles on recirculating trajectories such as $D_T$ in FIG. 1, thereby substantially preventing extraneous particle pulses. However, suspension flow through conduit 10' of Leif structure 12 also retains characteristics of flow through conventional Coulter conduit 10 in FIG. 1, including sensitivity to orifice edge defects. Construction of Leif structure 12 to working precision is sufficiently difficult that in later work the design was simplified, by replacing circular platinum electrodes 13 and 14 of FIG. 2 with platinum pins fixed in insulating spacing-elements 23 and 24.

In the Salzman structure, the volumeter conduit passes through potential-sensing electrodes so that the sensing electrodes are located within the conventional volumeter conduit [G. C. Salzman, P. F. Mullaney, and J. R. Coulter; A Coulter volume spectrometer employing a potential sensing technique, Biophysical Society Abstracts, 17th Annual Meeting, Abstract FPM-F11; *Biophysical Journal*, 13:302a, 1973]. The only known description appears in aforementioned U.S. Pat. No. 3,924,180 to G. C. Salzman, J. R. Coulter, P. F. Mullaney, and R. D. Hiebert. The objects of the '180 patent were reduction of sensitive-zone coincidence volume and particle pulse-width, with improvement of pulse signal-to-noise ratio. In contrast to the FIG. 2 Leif structure 12, the Salzman structure (38 in FIG. 3) places thin platinum potential-sensing electrodes 41 and 42 in contact with functional Coulter wafer W', with each electrode isolated from the suspending liquid by a circular insulating element 43 or 44. As for the Leif structure, the individual sensing electrodes 41 and 42 and insulating elements 43 and 44 in the Salzman structure each contain a central circular opening (46, 47, 45, or 48, respectively) aligned coaxially with Coulter conduit 10"; however, in the Salzman structure 38 these openings are of the same nominal diameter as Coulter conduit 10". The openings through insulating element 43, electrode 41, Coulter wafer W, electrode 42, and insulating element 44 of the Salzman structure collectively form a continuous wall 30' defining volumeter conduit 40 of uniform diameter and interconnecting the two compartments of the vessel containing the suspending liquid in which excitation electrodes are immersed. The walls of openings 46 and 47 in sensing electrodes 41 and 42 are in electrical contact with the suspending medium carrying the particles through conduit 40, and electrodes 41 and 42 are operatively connected to high-impedance sensing circuits, so that no significant electrical current flows between them.

For the Salzman structure 38 of FIG. 3, characteristics of the hydrodynamic and electric fields are co-determined and theoretically identical to those for a Coulter conduit of length L', with one-percent equipotentials 35 and 36 in the latter when particles are sensed between the excitation electrodes. However, in the Salzman four-terminal approach it is intended that only that portion 10", of conduit 40 between sensing electrodes 41 and 42 produce a signal pulse on passage of a particle through the conduit. Due to the longer total conduit 40 the electric field in 10" is substantially homogeneous, being isolated from the orifice field gradients by the thickness of insulating elements 43 and 44. Because the separation between electrodes L (=0.144 mm), conduit length L' (=0.412 mm), and conduit diameter D (=0.087 mm) were important to the objects of the invention, these dimensions were specified in the '180 patent. However, neither the thicknesses nor the lateral extents of electrodes 41 and 42 and insulating elements 43 and 44 are related to the inventive objects, and none of these dimensions were addressed. Thus, in FIG. 3 of the '180 patent, insulating elements 43 and 44 are indicated to be identical to the functional Coulter wafer W', i.e., 0.144 mm thick for the example. Because the collective thicknesses of elements 43, 44, and W' then exceed the stated length L' of the conduit, electrodes 41 and 42 must be vanishingly thin, i.e., not a small fraction of a conduit diameter in thickness as illustrated in the present FIG. 3. Thin electrodes 41 and 42 thus coincide with equipotentials of the homogeneous electric field, viz., the electric field within the conduit is unaffected by the presence of the electrodes if the latter are connected to high-impedance sensing circuits. Thus, the extent of sensitive zone $Z_S$ is substantially defined by the thickness L of wafer W' separating electrodes 41 and 42. By decreasing the thickness L of functional Coulter wafer W' the coincidence volume of sensitive zone $Z_S$ may in principle be decreased, with correspondingly decreased particle pulse-width; insulating elements 43 and 44 serve to isolate sensing electrodes 41 and 42 (due to the fluid resistances within openings 45 and 48 therein) from noise originating in the suspending medium within the dual-compartment vessel. For sufficient thicknesses of elements 43 and 44, there are no substantial regions of high electric-field gradients near sensitive zone $Z_S$ to cause either anomalous or extraneous pulses.

In FIG. 3, the hydrodynamic field begins developing convergent flow near the entry to opening 45 in insulating element 43. If of sufficient combined thickness, electrode 41 and insulating element 43 permit trajectories of particles to be straightened, so that particle trajectories through sensitive zone $Z_S$ such as $B_T$ or $C_T$ in FIG. 1 are essentially eliminated. Sufficient combined thickness of electrode 42 and insulating element 44 similarly precludes availability of sensitive zone $Z_S$ to particles on recirculating trajectories such as $D_T$ in FIG. 1, thereby eliminating extraneous particle pulses. However, these hydrodynamic effects are less important than for the Coulter conduits 10 or 10' of FIGS. 1 or 2, since there are no significant electric-field gradients near electrodes 41 and 42. Consequently, particles on near-wall trajectories through sensitive zone $Z_S$ of FIG. 3 do not produce anomalous pulses when the particle pulse is sensed between electrodes 41 and 42. However, suspension flow through conduit portion 10" of the Salzman structure 38 retains characteristics of flow through conventional Coulter conduit 10 in FIG. 1, including sensitivity to defects in wall 30'. Construction of Salzman conduit structures to the requisite quality has also proven difficult.

Both the Leif and Salzman potential-sensing approaches introduce liquid columns of comparatively small diameter between the excitation electrodes and the sensitive zone of the conduit structures (liquid-filled openings in spacing-elements 23 and 24 in FIG. 2 or elements 43 and 44 in FIG. 3, respectively). Electrically in series with the volumeter conduit, these liquid columns not only isolate the sensitive zone from electrical noise coupled into the bulk of the suspending medium in the two compartments of the dielectric vessel, but form part of a voltage divider between the excitation electrodes. The portion of the total pulse signal developed between the sensing electrodes on passage of a particle is determined by the ratio of the change in impedance between the sensing electrodes to the total impedance existing between the excitation electrodes. Because the liquid columns separate the sensitive zone $Z_L$ from the two sensing electrodes 13 and 14 in the Leif structure of FIG. 2, particle pulses are superimposed on a low-voltage pedestal originating in the potential gradient along the column, and pulse processing may be complicated in some analytic methods, as has been noted. In the Salzman structure of FIG. 3, this disadvantage is avoided because sensing electrodes 41 and 42 are adjacent to sensitive zone $Z_S$, but at the expense of reduced particle-pulse amplitude between the two sensing electrodes. The reduced pulse amplitude is due to the voltage-divider effect of the small-diameter liquid columns through elements 43 and 44, by which $Z_S$ is electrically connected to the bulk of the suspending medium in the dual-compartment vessel.

In the '180 patent there is suggested, but not described in detail, a variant structure obtained through omission of both insulating elements 43 and 44 in FIG. 3; as shown in FIG. 4, uninsulated electrodes 41' and 42' of this variant structure are exposed to the suspending liquid on their lateral faces as well as on the wall of openings 46' or 47' through them. Omission of elements 43 and 44 does eliminate the voltage-divider effect due to the fluid columns in the openings therein, but also eliminates a stated goal of the '180 patent, the beneficial hydrodynamic effects of the long FIG. 3 conduit 40. The hydrodynamic field for this variant four-terminal structure is theoretically identical to that of a FIG. 1 two-terminal Coulter volumeter conduit of equivalent conduit dimensions, and its axial electric-field distribution is also similar to that of the conventional conduit. However, as illustrated in FIG. 4, the thin sensing electrodes on the lateral surfaces of functional Coulter wafer W' impose new equipotentials on the distribution of the electric field near W' and near the wall of conduit 40', with some reduction in the effective spatial extent of the electric field near W'. Thus, the one-percent equipotentials 35" and 36" of the FIG. 4 electric field distribution originate at the openings of conduit 40', rather than at a distance from these as for functional conduits 10 or 10' in the volumeter structures of FIGS. 1 or 2, respectively.

For particle pulses sensed between the excitation electrodes, particles on trajectories such as $A_T$, $A_T$, $C_T$, or $D_T$ generate pulses similar to those on similar trajectories through the FIG. 1 conduit, except that in the FIG. 4 conduit the latter trajectory can result in pulses of greater amplitude and shorter duration. For pulses sensed between electrodes 41' and 42', the pulse effects of electric-field gradients outside openings 46' and 47' therein are significantly reduced, and the anomalous or extraneous pulses generated by particles on trajectories $B_T$ and $C_T$ or $D_T$, respectively, are substantially eliminated. Suspension hydrodynamics through the FIG. 4 structure share with the FIG. 1 and FIG. 2 structures a sensitivity to imperfections in the entry region; further, due to contiguity of sensing electrodes 41' and 42' to the conduit orifices, the electric field distribution is significantly more sensitive to such imperfections in the variant Salzman structure than for either of the latter structures.

Structure 38 of FIG. 3 is illustrated in U.S. Pat. No. 4,019,134 to W. R. Hogg, as suited to providing a control signal responsive to changes in conductivity of the suspending liquid; and in aforementioned U.S. Pat. No. 4,224,567 it is specified as suited to resistance calibration of the primary apparatus. A derivative structure taught by M. T. Halloran (aforementioned U.S. Pat. No. 4,484,134) is yet another implementation; in it dielectric tubes similar to those in aforementioned U.S. Pat. Nos. 4,290,011 and 4,434,398 are used as elements 43 and 44 in the FIG. 3 structure. In aforementioned U.S. Pat. No. 4,161,690 a form of the Salzman structure is used to allow assessment of the time course of primary pulse development as sensed between the two-terminal excitation/sensing electrodes, viz., at least one auxiliary sensing circuit, connected between one of the excitation/sensing electrodes and a dedicated auxiliary electrode contacting the fluid within the conduit channel, provided an auxiliary signal permitting either selecting primary pulses having certain characteristics or sampling primary pulses at a desired stage in their development. In this latter patent, one insulating element (43 or 44) and one electrode (41 or 42) are omitted from the present FIG. 3 structure 38 to provide the preferred implementation.

Certain applications may benefit from use of sequential conduits, so that the same particle may be either passively sensed more than once (aforementioned U.S. Pat. No. 3,793, 587 to R. Thom and J. Schulz) or actively modified in the second conduit by a field-effected operation applied in response to the measurement made in the first (e.g., aforementioned U.S. Pat. No. 4,525,666 to M. R. Groves). Apparatus described in these patents incorporate plural discrete Coulter conduits, each conduit interconnecting sequential compartments containing two-terminal excitation/sensing electrodes immersed in the suspending liquid. For each conduit, electrical circuitry connected between a pair of adjacent electrodes provides excitation current and may derive a particle pulse, as in the =508 apparatus. However, fluidic subsystems substantially more complex than are needed in the '508 apparatus must be used. Further, the unavoidable separation between sequential discrete conduits requires use of additional methods (e.g., such as described in U.S. Pat. No. 4,184,766 to W. R. Hogg) for correlating the activities within the individual conduits; for these, correlation accuracy scales directly with particle size and inversely with conduit separation. Because the latter is grossly indeterminate with respect to particle size, these complex methods seldom achieve high creditability. Due to the jetting flow exiting traditional Coulter conduits, flow patterns in the fluidic gap separating such sequential conduits require hydrodynamically focused flow to maintain the particle stream within a useful portion of the second conduit (e.g., U.S. Pat. No. 3,793,587).

Integrated structures incorporating tandem sensitive zones should offer attractive advantages over the discrete sequential structures of aforementioned U.S. Pat. Nos. 3,793,587 and 4,525,666. In particular, the fluidic gap and its jetting flow would be eliminated, the need for complex fluidic subsystems and methods based on hydrodynamically focused flow would be minimized, and correlation problems experienced with discrete sequential-conduit structures would be significantly reduced by the fixed design of fluidically-closed integrated structures. Both the '180 patent and the aforementioned U.S. Pat. No. 4,161,690 suggested assemblies incorporating additional thin sensing electrodes into integrated structures containing a continuous composite conduit, but neither patent described or claimed such structures. An extended form of the '180 conduit, containing a plurality of functional Coulter conduits in fluidic sequence, was proposed in aforementioned U.S. Pat. No. 4,438,390. The many precision components and precise assembly requirements of such integrated structures make them extremely difficult to build, and few have been reduced to practice. Specifically, prototypes of the '180 structure are known to have been tested, and forms of art in aforementioned U.S. Pat. No. 4,161,690 have been commercialized. Other integrated conduit structures have received little practical use, including those of the '390 patent and the aforementioned U.S. Pat. No. 4,484,134, both having in common the assignee of the related and present applications.

Perhaps more pertinent to this lack of development may be the fact that the prior art regarding integrated structures containing electrodes does not anticipate aspects important to practical realization of these structures. In particular, the prior art only recognizes electrodes in integrated conduit structures as potential-sensing interface devices, whereby the passage of a particle through the volumeter conduit may be detected by the sensing circuitry. This prior art does not recognize any functional effect of the electrodes on the electric fields within conduits of such structures but, through use of thin electrodes, substantially prevents the electrodes from affecting conduit field distributions. Specifically, aforementioned U.S. Pat. Nos. 3,924,180; 4,019,134; 4,161,690; 4,224,567; 4,290,011; 4,438,390; 4,434,398; and 4,484,134 typically illustrate electrode thicknesses to be less than the diameter of the Coulter conduit in thickness, but little discussion is given. As has been noted in discussion of the FIG. 3 Salzman structure 38, the '180 patent describes neither the lateral extent nor the thicknesses of the electrodes, but gives dimensions of the other assembly components which force the thicknesses to be vanishingly thin. The structure of the '180 patent is illustrated, but not further described, in U.S. Pat. No. 4,019,134; and in U.S. Pat. No. 4,224,567 it is specifically cited, but not further described. U.S. Pat. Nos. 4,290,011 and 4,434,398 illustrate an elongate conduit, which incorporates at its entry orifice one of two excitation/sensing electrodes as a ring of unspecified dimensions. In U.S. Pat. No. 4,161,690 the thickness of the internal auxiliary electrode is said to be small in relation to length L of the fluid channel; in the '390 patent the thickness of each electrode is illustrated as being significantly less than Coulter wafer thickness L; and in U.S. Pat. No. 4,484,134 the thickness of each electrode is said to be of the order of 5 percent of the Coulter conduit diameter D. This universal use in the prior art of electrodes thin with respect to conduit dimensions demonstrates the unanticipated and non-obvious nature of the interaction between electrode dimensions and conduit functional characteristics.

Because the '390 patent claims conduit structure described or claimed in much of the prior art, it will be taken as representative.

In the '390 patent structure is claimed which is based on at least two Coulter wafers, assembled between at least three sensing electrodes; at least one electrode is sandwiched between two Coulter wafers and the volumeter conduit passes through said sandwich. Each pair of adjacent electrodes is operatively connected to a differential sensing circuit, so that as a given particle transits the plural portions of the composite conduit, multiple particle pulses sequenced in time can be developed.

1. If remote sensing electrodes are used, the conduit structure and symmetric ambit fields correspond to those of FIG. 3 structure 38, with Coulter wafer W' and electrode 42 omitted; Except for the surface constituting the wall of the opening through the electrode, the latter is insulated from the sample suspension by elements 43 or 44. The conduit structure is that of U.S. Pat. No. 4,161,690, in which connections of the sensing circuitry may be different.

2. If the second sensing electrode is located on the outer surface of one of the outer-most Coulter wafers, the conduit structure corresponds to that of FIG. 3 with either insulating element 43 or 44 omitted, and one ambit field resembles those of the FIG. 3 structure 38 while the ambit field at the affected orifice resembles those of the FIG. 4 structure 38'.

3. If the third sensing electrode is located on the outer surface of the second of the outermost Coulter wafers, a tandem version of the FIG. 4 variant Salzman structure 38' is formed, and both ambit fields resemble those shown in FIG. 4.

4. Any of the preceding structures can in principle be extended in an obvious manner, by adding Coulter wafers and/or electrodes in a fluidically continuous manner. Thus, adding a Coulter wafer to insulate the exposed electrode of the second structure results in the '180 patent structure 38 of FIG. 3, while appropriately adding two Coulter wafers and another electrode results in a tandem version of this structure.

Because of their thinness, each sensing electrode essentially coincides with an equipotential in the conduit field distribution. In all '390 structures, the internal ambits between adjacent Coulter conduits resemble those within openings 46 or 47 of electrodes 41 or 42 of the FIG. 3 Salzman structure 38. Consequently, particle pulses from the outer sensitive zones of any '390 structure are both asymmetric and unlike those from any internal sensitive zone. The dissimilar rise and fall times may significantly increase the difficulty of using such pulses, e.g., in the pulse-averaging method taught in the '390 patent. Of lesser importance, but of potential concern in some applications, is the trajectory-dependent difference in asymmetric pulse characteristics generated by particles transiting asymmetric '390 structure, e.g., any '390 structure having an equal number of Coulter wafers and electrodes.

A further limitation becomes apparent when integrated tandem-conduit structures are considered for use in applications requiring active control of conduit fields, e.g., aforementioned U.S. Pat. Nos. 4,525,666 and 4,972,137, both having in common the assignee of the related and present applications. In the first of these patents, remote excitation/sensing electrodes are used to actively modify a biological particle (cell) by ramping the electric field in a second discrete sequential conduit in response to a parameter sensed in a preceding discrete conduit; in the second, remote auxiliary electrodes are used to isolate a single discrete conduit from the rest of the fluidic subsystem. The confined fluid flow through integrated conduit structures would make such active use of incorporated electrodes very advantageous, although such use is unknown in the prior art. However, as illustrated in FIGS. 1 through 4, electric field distributions bulge convexly outward from regions of high field intensity in the sensitive zones into regions of lower field intensity, e.g., into the suspending medium in the compartments interconnected by the volumeter conduit. If a higher field intensity is induced in any selected portion of an integrated conduit structure, e.g., the FIG. 3 conduit 40, by appropriately connecting a second excitation source between any of the sequential pairs of electrodes (viz., the excitation electrode in the vessel external to element 43 and electrode 41, electrodes 41 and 42, or electrode 42 and the excitation electrode in the vessel external to element 44), the resultant high field intensity within said portion will cause the ambit fields of that portion to bulge through the openings 46 or 47 of thin electrode 41 or 42 into the adjacent portion more or less according to the ratio of the field intensities in the two portions. If the second excitation source is made to provide a time varying field within the selected conduit portion, the ambits of said portion will intrude into the adjacent portions in a time-varying manner. Thus, the thin electrodes of prior-art integrated conduit structures do not favor active use of the incorporated electrodes, since the field manipulations required to achieve the desired conditions in one sensitive zone will interact with and affect the electric fields of adjacent sensitive zones. The consequent substantial change in spatial extent of the effective sensitive zone in any adjacent portion of the volunteer conduit will degrade the volumetric accuracy of measurements made therein.

Although the prior art alludes to hydrodynamic advantages of longer conduit structures, it neither details the origin of such advantages nor suggests a specific method whereby such advantages may be systematically obtained. Further, other than nonspecific observations (e.g., in the '390 patent) that the walls of the conduit should be fluidically smooth in integrated conduit structures, the prior art does not recognize any functional effect of the electrodes on hydrodynamic fields within the incorporated conduits. Prior-art conduit structures often practically require hydrodynamically focused flow or sweep flow, and in addition to undesirable complexity, such apparatus precludes positive-displacement determinations of particle concentration.

There is no question that the accuracy, resolution, and convenience of the two-terminal Coulter art have substantially benefited through the teachings of the many patents cited above and in the related application. While the potential-sensing, tandem, and active forms of the Coulter art potentially offer many advantages which may enable new forms and applications of the Coulter principle, prior-art apparatus and methods based on these have demonstrated many practical limitations and disadvantages. Some of the latter originate in the functional properties of the traditional Coulter conduit, for which a rich prior art in facilitating apparatus and methods has developed. As discussed in the related application, it is preferable to obviate such facilitating apparatus and methods, by directly amending field characteristics of the volumeter conduit.

It is desirable that a practicable integrated volumeter structure be provided which offers improved characteristics in its hydrodynamic and electric conduit fields. It is desirable that the improved volumeter structure be useful with apparatus for four-terminal potential sensing methods, e.g., aforementioned U.S. Pat. Nos. 3,924,180; 4,019,134; 4,224, 567; or 4,484,134 or bridge methods such as described in the aforementioned publication by R. A. Thomas, B. F. Cameron, and R. C. Leif. It is also desirable that the improved volumeter structure lend itself to use in methods requiring plural tandem volumeter conduits, e.g., those of aforementioned U.S. Pat. Nos. 3,793,587 or 4,438,390. Furthermore, it is desirable that the improved volumeter structure be useful i n methods requiring active control of electrode potentials or electric-field intensity in one or more of plural conduits, e.g., aforementioned U.S. Pat. Nos. 4,525,666 or 4,972,137, respectively.

SUMMARY OF THE RELATED INVENTION

The two-terminal apparatus and method of the related application is characterized by a novel field-amending volumeter assembly which offers many advantages over the conventional Coulter particle-sensing conduit of FIG. 1. A comprehensive description of the field-amending volumeter, its construction, and its functional characteristics is contained in the related application, said description being incorporated herein in its entirety by reference. Because of the advantageous functional characteristics of the field-amending volumeter assembly, Coulter apparatus incorporating it may avoid need for the complex assemblies and subsystems required by aforementioned facilitating methods. Consequently, when compared with prior-art two-terminal apparatus for sensing and characterizing particles by the Coulter principle, apparatus incorporating the field-amending volumeter conduit of the invention affords some or all of the following advantages:

A. Facilitating subsystems related to methods based on pulse deletion, hydrodynamically focused flow, or dynamic sweep flow may be eliminated, with significant reduction in manufacturing costs and appreciable improvement in system reliability;

B. Because auxiliary fluidic subsystems may be eliminated, particle concentration may be readily determined by positive-displacement volumetric methods;

C. Because functional sample dilution due to sheath fluid is eliminated and need for post-collection pulse deletions may be significantly reduced, sample volumes and processing times may be reduced; and D. Because of the significantly reduced coincidence volume compared to prior-art volumeter conduits, the rate of sample throughput can be increased for a given detectability threshold and level of coincidence artifact, or a larger conduit diameter may be used to decrease clogging concerns.

For convenience, relevant points of present interest may be summarized as follows.

In the related application, limitations of the FIG. 1 Coulter volumeter conduit are alleviated via a two-terminal volumeter assembly so constructed that the electrical resistivity of the wall defining the volumeter conduit therein is made to effectively vary in an axisymmetric manner along the conduit length (i.e., in a direction parallel to the flow of suspension through the conduit) so as to define a conduit having in any longitudinal conduit section a delimited central region of high electrical resistivity which is smoothly contiguous on its opposing boundaries to uninsulated distal regions of substantially lesser electrical resistivity. The electrical resistivity of the delimited central region is substantially greater, and the electrical resistivity of the uninsulated distal regions less, than that of the liquid in which the particles to be characterized are suspended. The delimited central high-resistivity region of the improved volumeter conduit functions as a traditional Coulter volumeter conduit. The uninsulated distal elements of the new volumeter conduit are made to have a minimum dimension along the conduit wall depending upon the desired detectability threshold in particle size, i.e., this dimension is made at least equal to the axial extent of the effective ambit electric fields of a traditional Coulter volumeter conduit having a cross-sectional geometry identical to that of the delimited central region of high resistivity in the improved volumeter conduit. Through their immersion in the suspending liquid, the uninsulated distal elements of the new volumeter conduit are electrically coupled to the electric field established by the excitation current through the high-resistivity region of the conduit. The uninsulated distal regions of the improved volumeter conduit assume independent potentials and independently function to amend both the electric and hydrodynamic fields in the vicinity of the volumeter conduit by: (i) shaping the electric field resulting from the excitation current so as to substantially confine the particle-sensitive zone within the physical boundaries of the conduit; (ii) enabling development of quasi-laminar flow through the particle-sensitive zone so as to significantly increase the proportion of particles per second transiting the substantially homogeneous areas of the particle-sensitive zone; and (iii) preventing particles that have already passed through the conduit and are on recirculating trajectories from re-entering the particle-sensitive zone.

With reference now to FIG. 5, according to the related application conduit C is thus defined by a continuous, hydrodynamically smooth wall 30' collectively comprising sequential wall portions through elements 52, 51, and 53 of volumeter assembly 50. The contiguous complementary surfaces of elements 52 and 51 form hydrodynamically smooth delimiting boundary 54, and those of 51 and 53 form hydrodynamically smooth delimiting boundary 55, respectively, between the portions of conduit C bounded by the respective elements 52, 51, and 53. Each said wall portion of conduit C is thus circumferentially bounded by the uninsulated solid material composing the respective element and smoothly contiguous at delimiting boundaries 54 and 55, respectively, to a congruent adjacent wall portion. The electrical resistivity of the element 51 is substantially greater, and the electrical resistivity of the uninsulated elements 52 and 53 less, than that of the liquid in which the particles to be characterized are suspended. Consequently, the characteristic electrical resistivity of defining wall 30' is caused to be substantially axisymmetric, but is made to have significant axial gradients at delimiting boundaries 54 and 55 along the length of any longitudinal section of conduit C. The characterizing axial variation in axisymmetric resistivities substantially originates in the characteristics of the solid materials selected for the make-up of volumeter structure 50, although geometries of individual elements may be caused to augment certain properties of conduit C. Volumeter assemblies incorporating the characteristic axial variation in axisymmetric resistivity of wall 30' may be embodied by a variety of techniques in a broad range of designs, geometries, and materials. In a preferred embodiment, element 51 is a FIG. 1 Coulter wafer W and elements 52 and 53 are uninsulated collars formed of an electrically conductive material fixed to element 51 so that the congruent through-holes in the three elements 52, 51, and 53 align to form a hydrodynamically smooth wall 30'.

As with the prior-art conduits of FIG. 1 through 4, characteristics of signal pulses generated by particles passing through conduit C of FIG. 5 structure 50 result from a complex interaction of the particles with both the electric field established in the suspending medium by the excitation current between the excitation electrodes and the hydrodynamic field established by the particle-suspending medium carrying the particles through conduit C.

In distinct contrast to prior-art conduits of FIGS. 1 through 4, uninsulated elements 52 and of FIG. 5 structure 50 assume individual potentials over their surfaces under influence of the electric field established by the excitation current and as a result directly superimpose independent equipotentials in the vicinity of conduit C. The distribution of the resultant electric field making up particle-sensitive zone Z' in FIG. 5 depends on conduit diameter D' and axial length L' of conduit portion 10', whereas the distribution of the resultant hydrodynamic through-field depends on D' and the cumulative length (L'+$L_1$+$L_2$) of conduit C, where $L_1$ and $L_2$ are the dimensions along wall 30' of elements 52 and 53, respectively. It has been found that the diameter D' and length L' of conduit portion 10' can be selected to provide specific electrical characteristics in sensitive zone Z' of conduit C and that (without adversely affecting the electrical characteristics of the sensitive zone) non-minimal lengths of $L_1$ and $L_2$ of elements 52 and 53 can be made to facilitate quasi-laminar flow through the sensitive zone so as to significantly increase the proportion of particles per second transiting the substantially homogeneous areas of the sensitive zone. Consequently, it has been found that effects of the electric and hydrodynamic fields on pulses generated by particles transiting sensitive zone Z' of volumeter conduit C can be independently optimized. In particular, ambit electric fields external to physical conduit C can be eliminated.

In distinct contrast to prior-art integrated conduit structures incorporating electrodes, respective thicknesses $L_1$ and $L_2$ of FIG. 5 field-amending elements 52 and 53 are greater than the diameter D' of conduit C, so providing functional properties not attainable with the prior-art conduits. Generally, respective axial lengths $L_1$ and $L_2$ of elements 52 and 53 between one to four times the diameter D' of functional Coulter conduit 10' are preferred; it is this novel axial thickness which enables their field-amending function on the electric and hydrodynamic fields of conduit C. It is preferred that the axial length of both elements 52 and 53 be at least approximately equal to the diameter D' of functional Coulter conduit 10' so that sensitive zone Z' is made substantially independent of the cumulative length of conduit C, and this is necessary if the effects of electric and hydrodynamic fields on particle-pulse characteristics are to best be optimized. It is preferred that L'/D' be in the range between 0.2 and 2.5. Longer lengths for element 52 may be useful in establishing a desired position of modal particle trajectories through said functional Coulter conduit, while longer lengths for element 53 may be useful in establishing a desired pressure/flow-rate relation for conduit C. Axial lengths of elements 52 and 53 somewhat less than the diameter D' of the functional Coulter conduit 10' may be used if detectability thresholds greater than approximately one percent are acceptable and anomalous pulses are of small concept. For two-terminal applications, it is preferred that volumeter assembly 50 comprise elements 51, 52, and 53.

Further, thick elements 52 and 53 of FIG. 5 structure 50 are not electrodes, viz., they are not connected to external electrical circuitry, but function independently of any external circuitry to perform their field-amending function.

Thus, structure 50 of FIG. 5 differs from the prior-art of FIGS. 1 and 2, wherein conduit wafer W is constructed of homogeneous dielectric material so that the wall defining conduit 10 or 10' is of uniformly high electrical resistivity, and the electric and hydrodynamic fields in the conduits are consequently co-determined by the conduit diameter D and the thickness L of the conduit wafer W. A similar contrast is seen for the variant Salzman conduit structure 38' in FIG. 4, due to the thinness of the electrodes 41' and 42' in the latter. Further, the sensitive zone of conduits in FIGS. 1, 2, and 4 extends outside the physical conduit.

In further contrast to the prior-art Leif conduit structure 12 in FIG. 2, wherein thick electrodes 13 and 14 are located outside the ambit fields of conduit 10', structure 50 elements 52 and 53 of FIG. 5 are located so as to influence the ambit fields of conduit 10'.

In further contrast to the prior-art Salzman conduit structure 38 in FIG. 3, wherein thin electrodes 41 and 42 are insulated by additional elements 43 and 44, uninsulated elements 52 and 53 of FIG. 5 structure 50 are preferably exposed to the medium in which the particles to be characterized are suspended. Elements 43 and 44 of the FIG. 3 structure 38 increase the difficulty of manufacturing practical structures, so that the simpler FIG. 5 structure 50 offers attractive commercial advantages. The electric field established by the excitation current through conduit 40 extends outside the physical conduit of the FIG. 3 structure 38.

In further contrast to both the Leif structure 12 of FIG. 2 and Salzman structure 38 of FIG. 3, conduit structure 50 of FIG. 5 does not introduce liquid columns of small diameter in series with the sensitive zone of the volumeter conduit, e.g., liquid-filled openings in elements 23 and 24 in the FIG. 2 structure 12 or elements 43 and 44 in the FIG. 3 structure 38.

The field-amending volumeter conduit of FIG. 5 affords the following advantages, when compared with prior-art two-terminal volumeter conduits for sensing and characterizing particles:

1. The ambit electric fields of the particle-sensitive zone resulting from the excitation current are substantially smaller, thereby reducing the likelihood of particle coincidence while increasing volumetric sensitivity;
2. The cross section of the particle-sensitive zone containing substantially homogeneous field regions may be significantly increased, thereby reducing the frequency of anomalous pulses and increasing the range in particle diameter for which the dynamic response is linear;
3. The suspension flow profile through the particle sensitive zone may be quasi-amine rather than quasi-uniform, whereby the proportion of particles per second transiting the substantially homogeneous areas of the particle-sensitive zone may be increased, further reducing the frequency of anomalous pulses; and
4. Particles may be prevented from transiting the particle-sensitive zone on trajectories curving through the ambit electric fields, thereby eliminating both anomalous pulses due to particles entering the sensitive zone on high-angle trajectories and extraneous pulses due to exiting particles recirculating into the exit ambit field.

Consequently, for the volumeter conduit C of FIG. 5, coincidence volumes are decreased as compared with the FIG. 1 Coulter volumeter conduit 10, and extraneous pulses occasioned by particles recirculating into the exit ambit field are eliminated. In addition, the anomalous particle pulses resulting from particles transiting the conduit on near-wall trajectories may be eliminated. When used with prior-art two-terminal Coulter apparatus, the improved volumeter assembly enabled nearly ideal volumetric measurements, with the aforesaid advantageous simplifying impact on apparatus design and construction.

It is preferred that volumeter assembly 50 in FIG. 5 comprise elements 51, 52, and 53, and as noted, this is necessary if particle sensitive zone Z' of conduit C is to be substantially symmetric about its axial midpoint. Some advantages may be obtained through use of only a single element 52 or 53 arranged at, respectively, the entry or exit of the functional Coulter conduit 10' in volumeter assembly C of FIG. 5. Thus, if the concern is reduction of histogram skewness due to particles transiting the sensitive zone near the conduit wall, element 53 could be omitted, the asymmetric ambit fields of sensitive zone Z' then resembling 31' in FIG. 5 on the entry side and 32 in FIG. 1 on the exit side; element 52 will reduce occurrence of anomalous pulses, but recirculating particles near the exit of the dual-element volumeter assembly will produce extraneous pulses and an artifactual low-volume distribution. Conversely, if the concern is elimination of the artifactual low-volume distribution due to recirculating particles, element 52 could be omitted and the asymmetric ambit fields of sensitive zone Z' will resemble 31 in FIG. 1 the entry side and 32' in FIG. 5 on the exit side; element 53 will reduce the occurrence of circulation pulses, but particles transiting the conduit of the dual-element volumeter assembly near its wall will produce histogram skewness due to anomalous pulses.

Examples of the improved volumeter assembly are provided in the several volumeter embodiments of the related patent application, said embodiments being herein incorporated in their entirety by reference.

SUMMARY OF THE INVENTION

In view of the foregoing discussion, an important object of this invention is to provide an improved apparatus of the type discusses above for sensing and characterizing particles, said apparatus providing improved functional characteristics in the hydrodynamic and electric fields associated with the volumeter conduit.

Another object of the invention is to provide a volumeter assembly which, owing to its unique structure, operates to amend characteristics of the electric and hydrodynamic fields associated with the Coulter volumeter conduit, thereby simplifying the make-up of instruments of the type which sense and characterize particles by means of the Coulter principle, including those forms based on potential-sensing methods, multiple sensitive zones, and active control of field intensities in one or more portions of the particle suspension passing through the volumeter conduit.

Yet another object of this invention is to provide an improved method for sensing and characterizing particles by the Coulter principle.

In accordance with the present invention there is provided a new and improved apparatus for sensing and characterizing particles by the Coulter principle. As in the prior art, the apparatus of the invention comprises: (a) a volumeter conduit through which a liquid suspension of particles to be sensed and characterized can be made to pass, (b) a liquid handling-system for causing the particle suspension to pass through the volumeter conduit; (c) a first electrical circuit for producing a nominal electrical excitation current through the volumeter conduit, such excitation current being effective to establish in the vicinity of the volumeter conduit an electric field having a particle-sensitive zone in which changes in the nominal excitation current as produced by particles passing through the conduit simultaneously with the excitation current are measurable; and (d) at least one second electrical circuit for monitoring the amplitude of the electrical current through the volumeter conduit so as to detect the presence or to sense the characteristics of particles passing through said conduit, operatively connected as will be described. In contrast to the prior-art apparatus, the volumeter assembly in the new apparatus is so constructed that, in the broadest sense, the electrical resistivity of the wall defining the volumeter conduit therein is made to effectively vary in an axisymmetric manner along the conduit length (i.e., in a direction parallel to the flow of suspension through the conduit) so as to define a conduit having in any longitudinal conduit section a delimited region of high electrical resistivity which is smoothly contiguous on at least one of its opposing boundaries to an uninsulated region of substantially lesser electrical resistivity. At least one of the current-monitoring second circuits is electrically connected to at least one of the uninsulated regions of the volumeter conduit. The electrical resistivity of the delimited region is substantially greater, and the electrical resistivity of the uninsulated region less, than that of the liquid in which the particles to be characterized are suspended. The delimited high-resistivity region of the improved volumeter conduit functions as a traditional Coulter volumeter conduit. Each uninsulated region of the new volumeter conduit is made to have a minimum dimension along the conduit wall depending upon the desired detectability threshold in particle size, i.e., this dimension is made at least equal to the axial extent of the effective ambit electric fields of a traditional Coulter volumeter conduit having a cross-sectional geometry identical to that of the delimited central region of high resistivity in the improved volumeter conduit. Through immersion in the suspending liquid, each uninsulated region of the new volumeter conduit is electrically coupled to the electric field established by the excitation current through the high-resistivity region of the conduit. Each uninsulated region of the improved volunteer conduit assumes independent potentials and independently functions to amend both the electric and hydrodynamic fields in the vicinity of the volumeter conduit by: (i) shaping in the vicinity of the uninsulated region the electric field resulting from the excitation current so as to substantially confine a substantial portion of the particle-sensitive zone within the physical boundaries of the conduit; and (ii) either enabling development of quasi-laminar flow through the particle-sensitive zone so as to significantly increase the proportion of particles per second transiting the substantially homogeneous areas of the particle-sensitive zone or preventing particles that have already passed through the conduit and are on recirculating trajectories from reentering the particle-sensitive zone.

In yet other forms, the above-noted current-monitoring circuit is replaced or supplemented with an electrical circuit for producing a nominal electrical effector current through at least a portion of the volumeter conduit, such effector current being effective to establish in the vicinity of such portion of the volumeter conduit an electric field having a field intensity different from that established in other portions of the volumeter conduit by the first electrical circuit. Preferably, such additional electrical circuit is operatively connected to at least one uninsulated region of the volumeter conduit and is responsive to a signal provided by the second electrical circuit.

The field-amending volumeter conduit of the present invention substantially affords the aforesaid advantages of the related application to novel forms of the Coulter art based on potential-sensing methods, multiple sensitive zones, or active control of field intensities in at least one portion of the particle suspension passing through the volumeter conduit. Such novel apparatus include field-amending volumeter conduits variously derived from those of the related application.

According to another aspect of the invention, volumeter assemblies incorporating field-amending volumeter conduits may be embodied in a variety of dissimilar constructions. In one preferred embodiment, the field-amending volumeter conduit is defined by a through-hole formed in a disc of electrically inhomogeneous material. At the site selected for forming the through-hole, the electrical resistivity of the disc is made to effectively vary through the thickness thereof, e.g., by suitable doping, to define at least one delimited region of high electrical resistivity which is contiguously bounded on at least one of its boundaries by an uninsulated element of substantially lesser electrical resistivity which intersects the face of the disc. A hydrodynamically smooth opening of the desired cross-sectional and longitudinal geometry is then formed through the disc.

The delimited high-resistivity region of the volumeter conduit so formed functions as a traditional Coulter volumeter conduit. The delimited high-resistivity region and the bounding uninsulated lesser-resistivity element thus collectively form a hydrodynamically smooth volumeter conduit, in which the electric and hydrodynamic fields of the traditional volumeter conduit are advantageously amended in the manner above noted. According to an alterable embodiment, each delimited region of the improved volumeter conduit is defined by a traditional conduit wafer, i.e., a dielectric wafer containing a central circular conduit as described in U.S. Pat. Nos. 2,985,830 or 3,771,058, and each element of lesser resistivity is defined by an uninsulated, electrically conductive, circular collar attached to one of the opposite sides of the conduit wafer. Each such collar is made to have a convenient outer diameter and a thickness between one to four times the diameter of the conduit in the conduit wafer. Each such collar has a central opening which is dimensioned and shaped to precisely conform to the conduit in the conduit wafer, and the collars are arranged on at least one of the opposite sides of the conduit wafer so that the respective collar opening overlies and remains congruent with one of the orifices of the conduit therein. The conduit in each conduit wafer and the opening in the each conductive collar thus collectively form a hydrodynamically smooth volumeter conduit, in which the electric and hydrodynamic fields of the traditional volumeter conduit are advantageously amended in the manner above noted.

A multiplicity of volumeter assemblies according to these or other embodiments may be sequentially assembled to provide volumeter assemblies having a desired number of functional Coulter conduits in a fluidically continuous and hydrodynamically smooth volumeter conduit. Volumeter assemblies according to such embodiments of the field-amending concept may be adapted by prior-art methods to enable simultaneous passage of a suitable suspension of the particles to be analyzed and an electrical excitation current through the field-amending conduit.

Yet another aspect of the invention is the provision of an improved method for sensing and characterizing particles in which the particles to be characterized are suspended in a liquid medium having an electrical impedance per unit volume which differs from that of the particles and passed substantially one at a time through the field-amending volumeter conduit of the invention while changes in a pre-established electrical current through such conduit are monitored.

A further aspect of the invention is the provision of an improved method for sensing and characterizing particles in which the particles in at least a portion of such conduit may be subjected to electric fields of a different intensity than established by the preestablished electrical current through such conduit. The field within such portion of the conduit may be modified in response to sensing of the approach of particles to, presence or characteristics of particles passing through, or departure of particles from, said conduit.

The invention and its advantages will be better understood from the ensuing detailed description of preferred embodiments, reference being made to the accompanying drawings in which like reference characters denote like parts.

BRIEF DESCRIPTION OF THE DRAWINGS

FIG. 6 illustrates the new apparatus for sensing and characterizing particles by the Coulter principle;

FIGS. 8A and 8B illustrate front and longitudinal-section views of an alternative embodiment of volumeter assembly adapted to use in the apparatus of FIG. 6A;

DETAILED DESCRIPTION OF PREFERRED EMBODIMENTS

Figure 1:
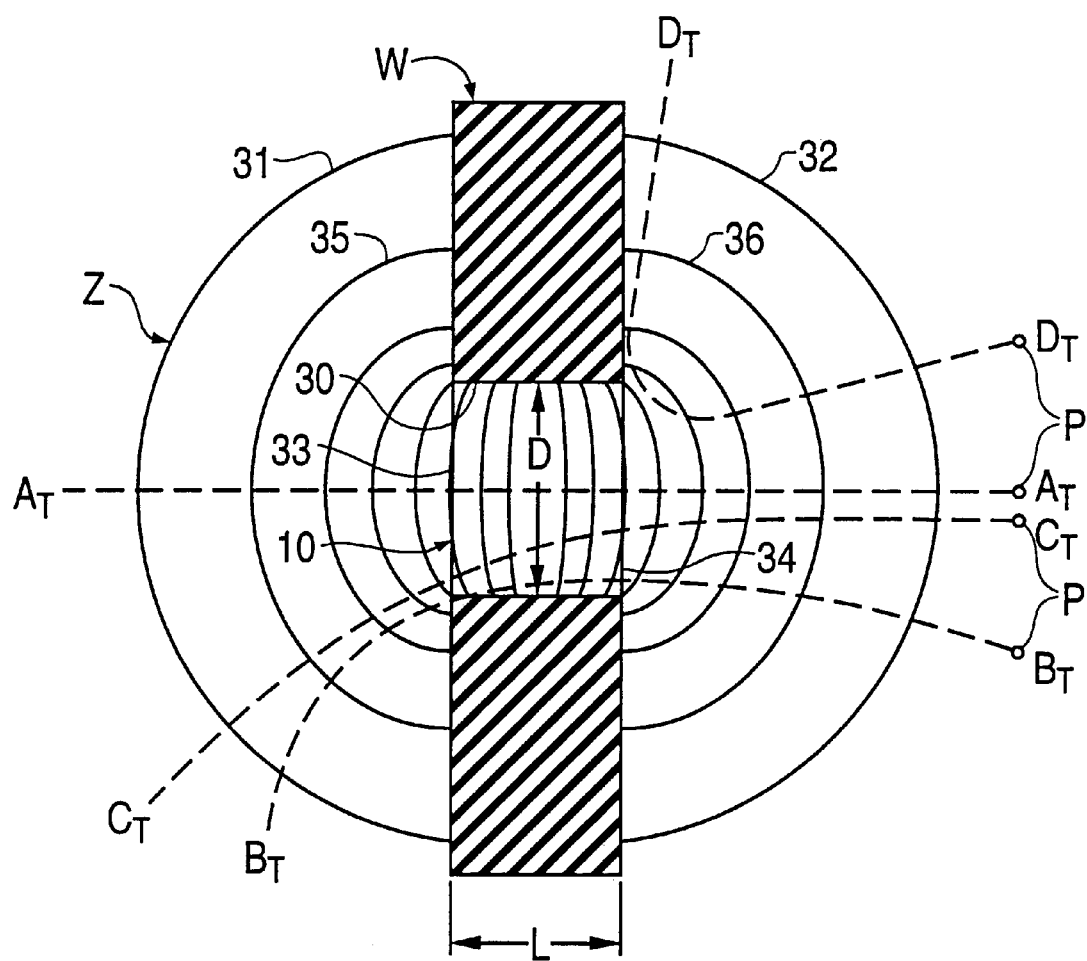
FIG. 1 illustrates a longitudinal section through the conduit and particle-sensitive zone of a Coulter two-terminal volumeter conduit wafer.
Figure 2:
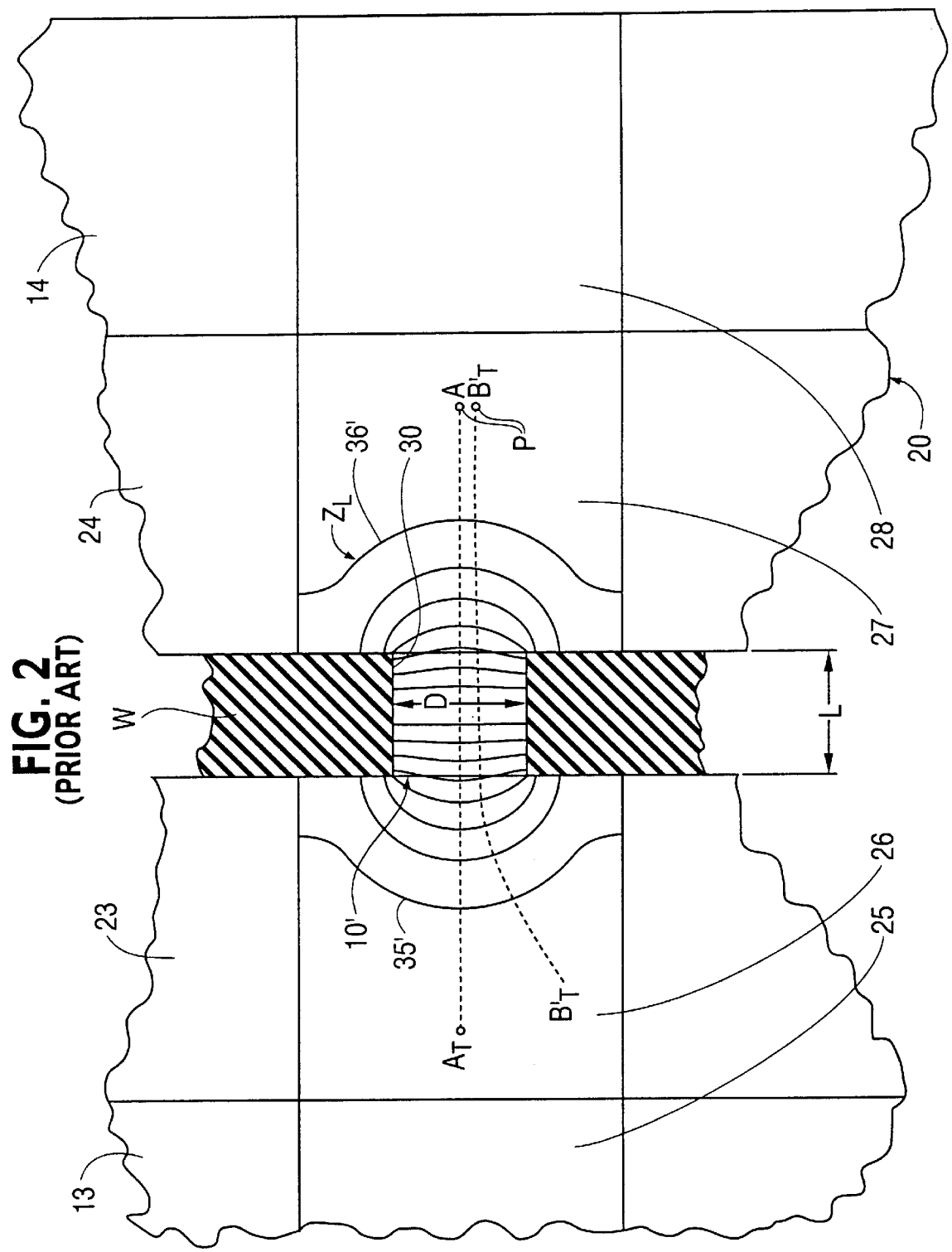
FIG. 2 illustrates a longitudinal section through the conduit and particle-sensitive zone of a potential-sensing, four-terminal Leif conduit structure.
Figure 3:
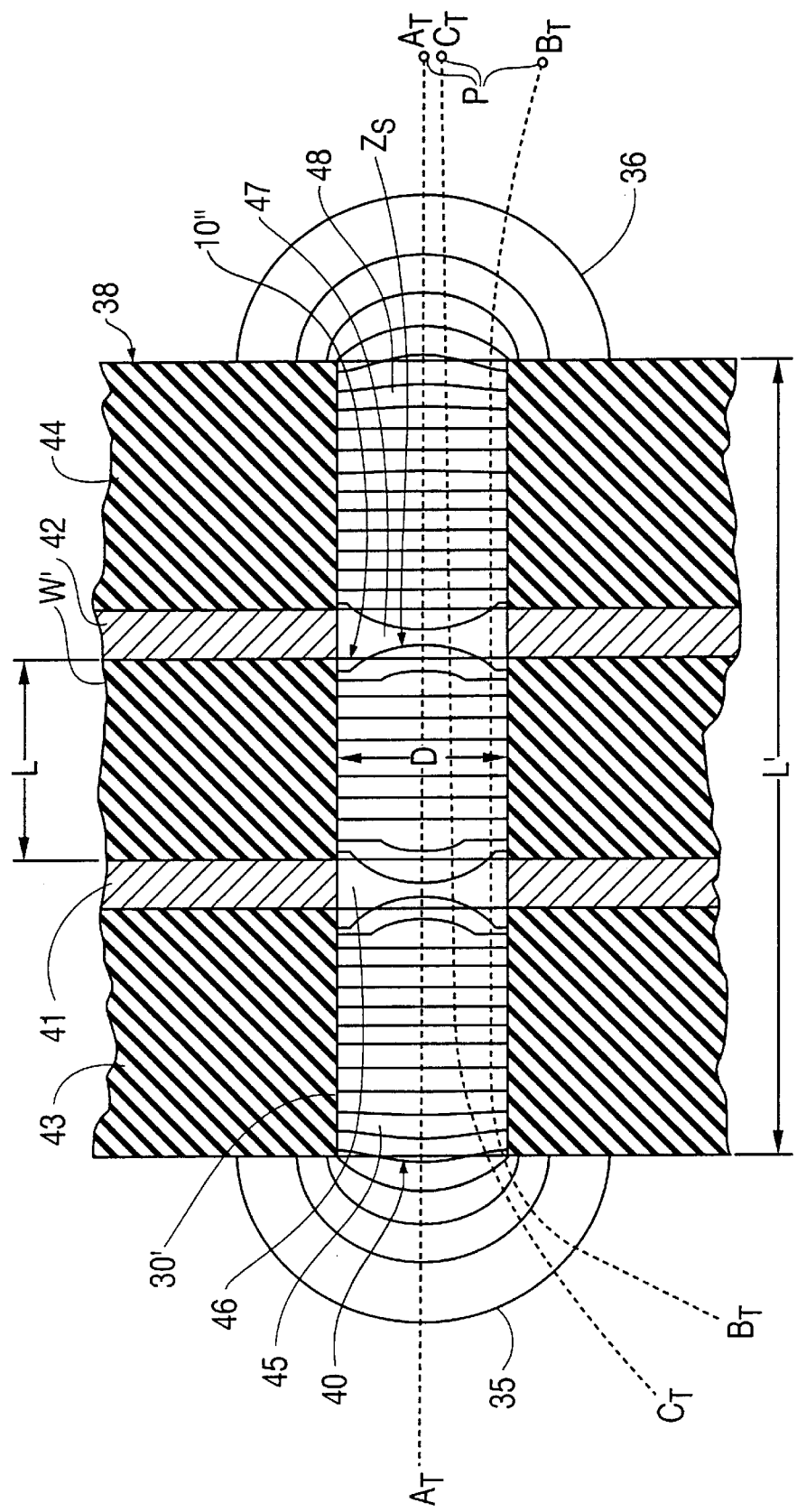
FIG. 3 illustrates a longitudinal section through the conduit and particle-sensitive zone of the potential-sensing, four-terminal Salzman conduit structure of U.S. Pat. No. 3,924,180.
Figure 4:
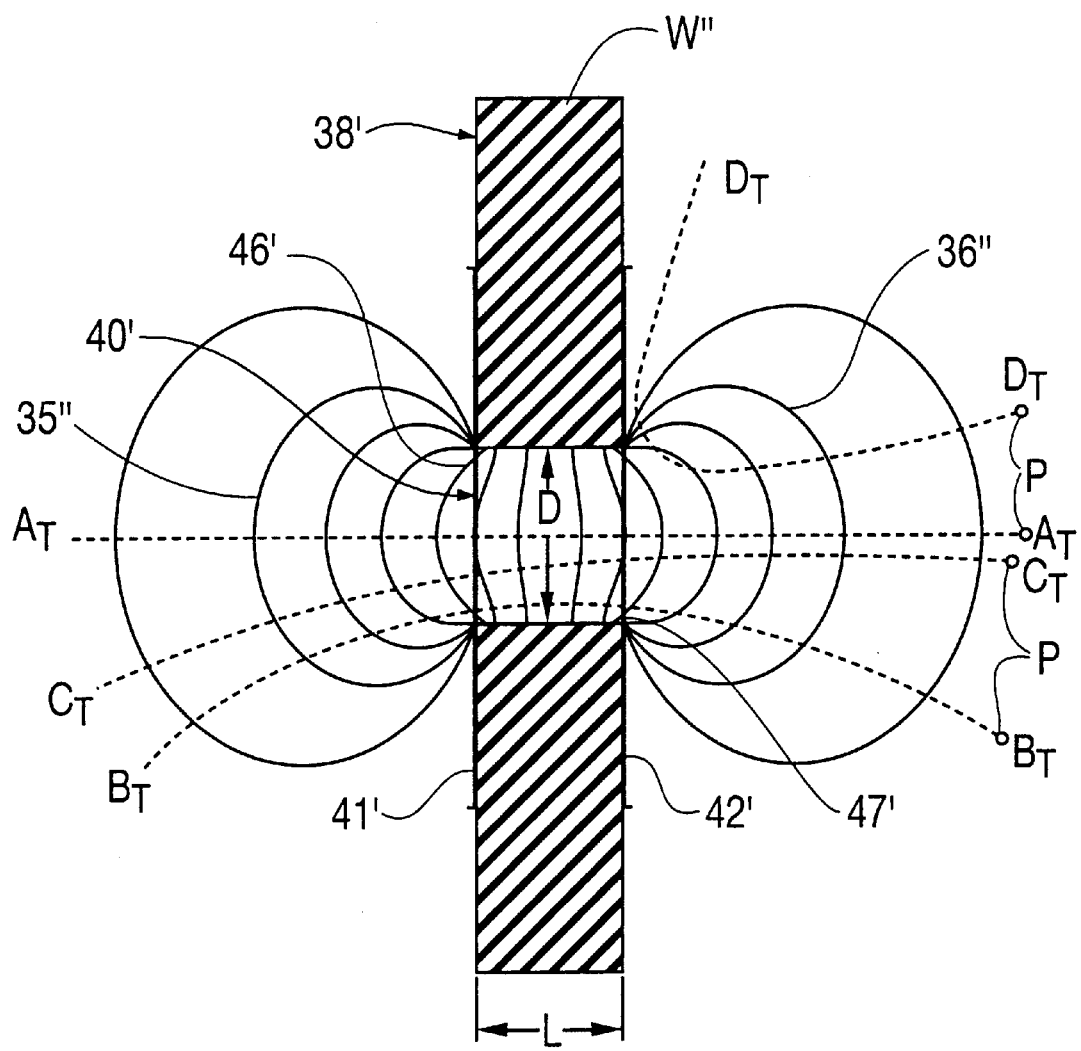
FIG. 4 illustrates a longitudinal section through the conduit and particle-sensitive zone of a variant four-terminal Salzman conduit structure.

An important object of this invention is to provide an improved apparatus for sensing and characterizing particles of the type which operates according to the aforementioned Coulter principle as adapted to sensing and characterization methods incorporating potential sensing, multiple sensitive zones, and active control of field intensities in one or more portions of the particle suspension passing through the volumeter conduit. In a general form this is accomplished by operatively connecting either sensing circuitry or effector current sources to at least one of the field-amending elements comprised in a field-amending volumeter conduit according to the related application, whereby said element may also function as an electrode suited to use in Coulter apparatus requiring more than two electrodes. Use of thin electrodes in similar structures has a varied prior art, as has been reviewed. With foreknowledge of field-amending conduits described in the related application, use of the field-amending elements comprised therein as electrodes is a simple concept. However, the complexity of the underlying interaction of a particle with the conduit fields, the scientific and commercial significance of the data inaccuracies resulting therefrom, and the rich and extensive prior art developed to ameliorate the problems associated with Coulter conduits all demonstrate that field-amending methods are non-obvious and therefore novel. The prior art includes neither field-amending methods nor apparatus whereby they may be implemented. These are described in detail for two-terminal Coulter methods and apparatus in the related application, incorporated herein in its entirety by reference. In the present application these are similarly described for forms of Coulter art requiring more than two electrodes. Because the methods of the invention directly mitigate a fundamental problem with Coulter conduits they are applicable to any form of apparatus incorporating Coulter conduits.

EMBODIMENT 1

In FIG. 6 is schematically illustrated, in accordance with a preferred embodiment of a first type of the invention, an improved apparatus for sensing and characterizing particles, one which provides improved functional characteristics in the hydrodynamic and electric fields associated with the volumeter conduit. Like prior-art Coulter apparatus, the apparatus of the invention preferably comprises a dual-compartment dielectric vessel 6 containing a wall 7 of dielectric material separating compartments 6A' and 6B', each of which is filled with a particle-suspending liquid medium M (e.g., isotonic saline solution) and each of which contains at least one respective discrete electrode 15 or 16.

Whereas the prior-art apparatus comprises a volumeter structure such as those shown in FIGS. 1 through 4, the FIG. 6 apparatus comprises a volumeter assembly 50' incorporating field-amending conduit C according to the related application. Although volumeter assembly 50' may be made to constitute wall 7, it is preferably provided as an independent structure, e.g., as a disc of appropriate dimensions. Volumeter assembly 50' is mounted over relatively large opening 7A in wall 7 and is substantially surrounded by and immersed in the particle-suspending medium M filling the compartments of vessel 6. A small through-hole transpiercing volumeter assembly 50' provides an improved volumeter conduit C which is caused to constitute the only operative electrical and fluidic connection between compartments 6A' and 6B'.

In operation, a conventional current source 17 operatively connected to discrete electrodes 15 and 16 establishes an appropriate nominal current flow through improved conduit C, while an appropriate vacuum applied to port 11 simultaneously establishes a flow of particle suspension (introduced into inlet port 8) from compartment 6A' through conduit C into compartment 6B'. Conduit C constricts both the electric and hydrodynamic fields so established in vessel 6, so that wall 30' of conduit C surrounds and defines the flows of particle suspension and electric current between compartments 6A' and 6B'. It is preferred that current source 17 be a constant-current source so that the current it supplies is substantially independent of changes in impedance between discrete electrodes 15 and 16 (e.g., due to substitution of conduits C having different diameters or lengths, temperature-induced changes in the resistivity of particle-suspending medium M, or substitution of suspending medium M having a different resistivity), but current source 17 may less preferably be a voltage source having a high internal impedance. A set 18 of conventional high-impedance circuitry 19, 20', and 21, operatively connected to field-amending elements 52' and 53' of volumeter assembly 50', functions to detect, sense, monitor, and process potential variations due to pulsations in conduit current as occasioned by the more or less individual passage of particles through conduit C, and conventional devices 22 operate to display or record particle count and characteristic data.

Figure 5:
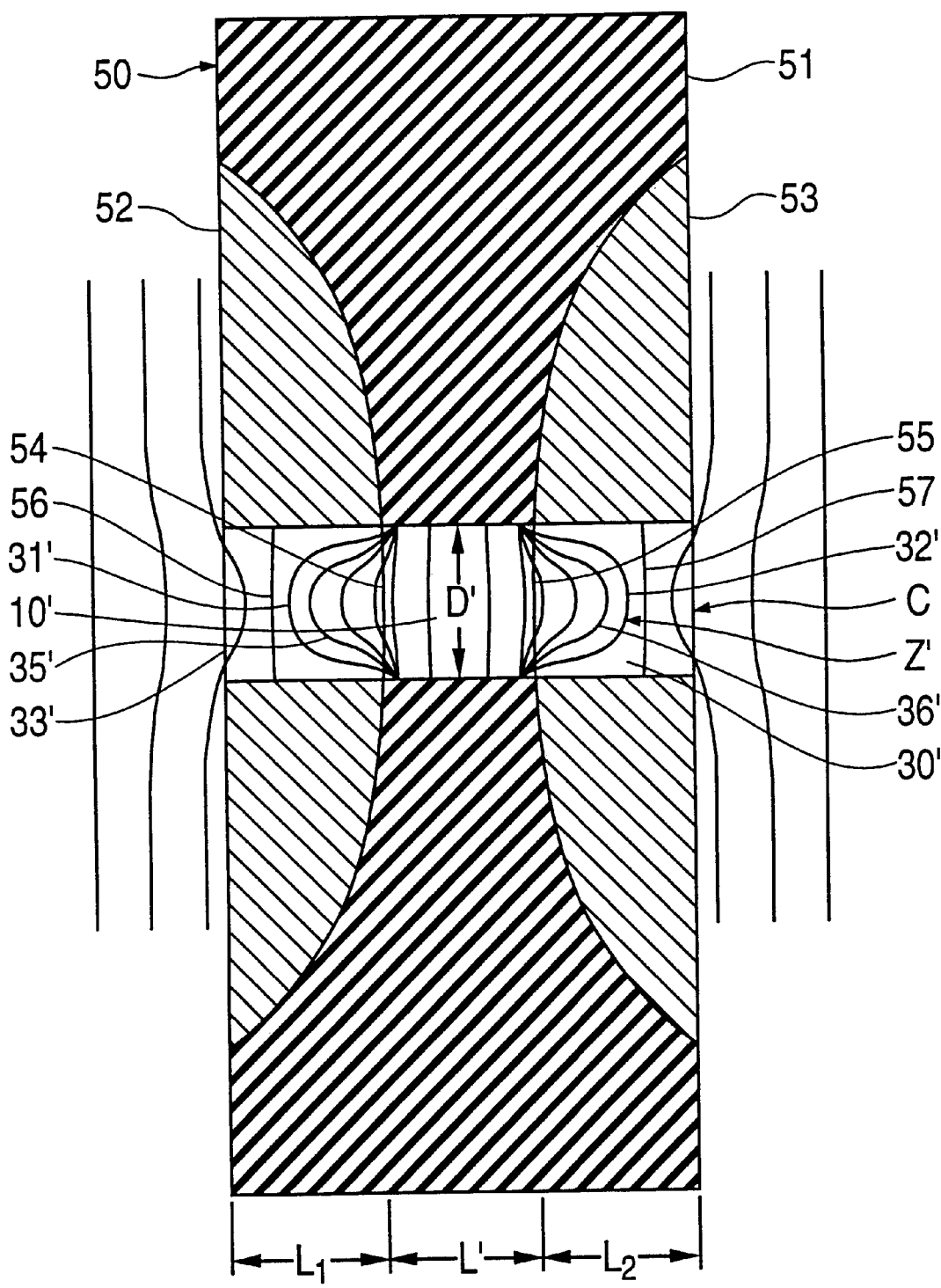
FIG. 5 illustrates a longitudinal section through the conduit and particle-sensitive zone of a two-terminal field-amending conduit structure of the related application.

As discussed in the "SUMMARY OF RELATED APPLICATION", the novel structure of volumeter assembly 50 in FIG. 5 is caused to provide conduit C with at least one delimited element 51 of high electrical resistivity which is smoothly contiguous on at least one of its axially opposing boundaries to an element 52 or 53 of substantially lesser resistivity. Element 51 serves as a functional Coulter wafer having functional conduit 10', and elements 52 and 53 have extents along the axis of conduit C at least substantially equal to the diameter of functional conduit 10'. Due to their axial extents, elements 52 and 53 serve to advantageously amend the electric and hydrodynamic fields in the vicinity of functional conduit 10'.

Field-amending elements 52 and 53 of volumeter assemblies described in the related application are not electrodes, but their field-amending function does not preclude their being used as electrodes in forms of the Coulter art requiring more than two electrodes. Provided the nominal electric field in conduit C (resulting from the nominal current from current source 17 therethrough) remains undisturbed during any period that particle characterization data is being acquired, incidental use of field-amending elements 52 and 53 as electrodes need not impair their field-amending function. This can be ensured by causing the quiescent state of any electrical circuitry operatively connected to said elements to produce no substantial effect on the nominal electric field in conduit C.

Figure 7:
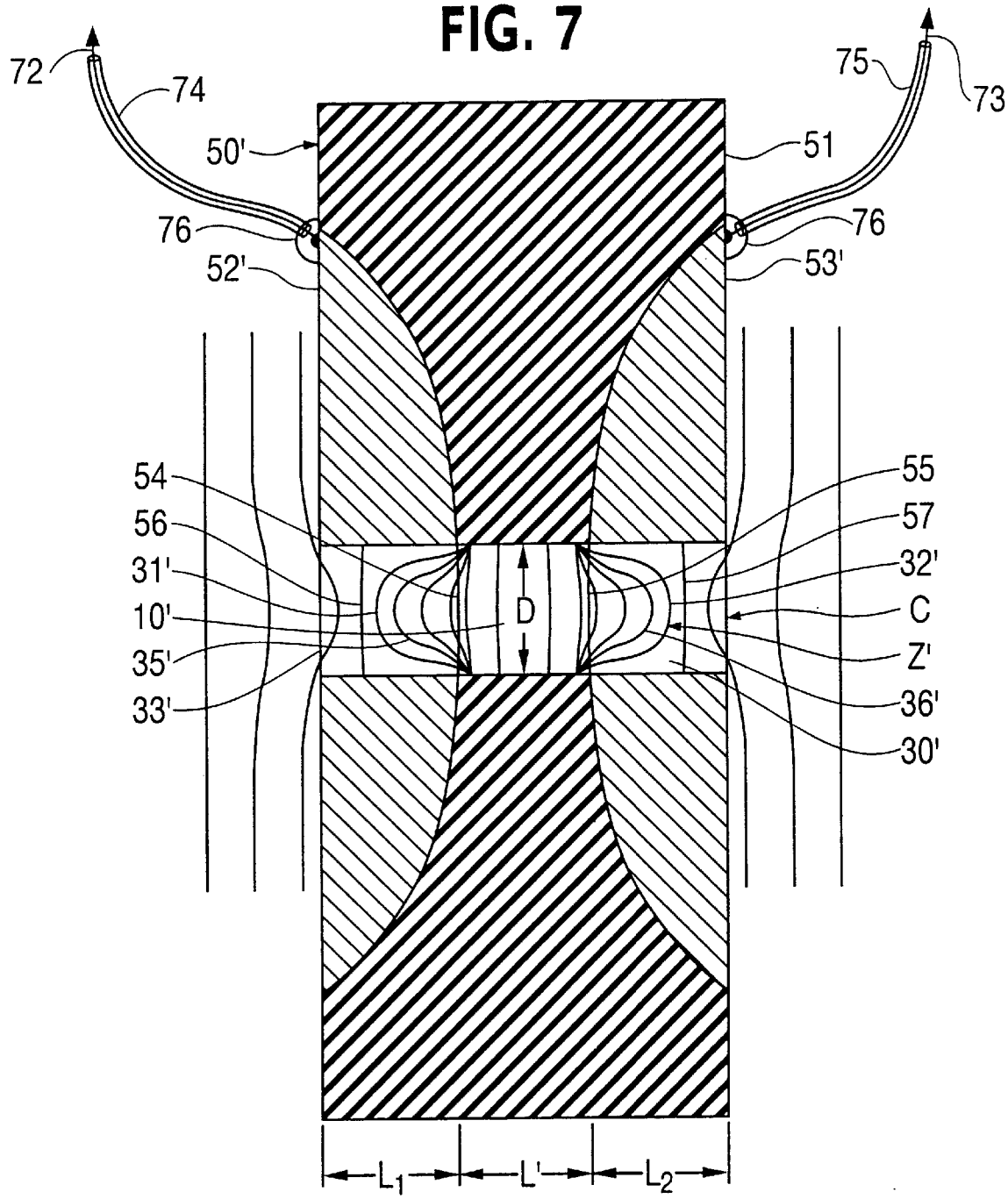
FIG. 7 illustrates a longitudinal section through the conduit and particle-sensitive zone of the FIG. 5 field-amending conduit structure adapted to use in the apparatus of FIG. 6A.

A preferred embodiment of volumeter assembly 50' is illustrated in FIG. 7 and described at length in Embodiment 2. The FIG. 7 volumeter assembly 50' comprises FIG. 5 volumeter assembly 50 and electrically conductive paths 72 and 73 operatively connected to respective field-amending elements 52 and 53 thereof, whereby sensing portion 19 of aforesaid high-impedance circuitry 18 may be operatively connected to said field-amending elements. One example of such electrically conductive paths comprises small-gauge insulated wire connected to elements 52' and 53' with conductive paint or low temperature solder and to the inputs $18_1$ and $18_2$ of aforesaid sensing circuitry by appropriate conventional methods. Field-amending elements 52' and 53' of the FIG. 7 embodiment thus combine the functionality of the FIG. 5 field-amending structure with that of prior-art integrated sensing electrodes.

Figure 6A:
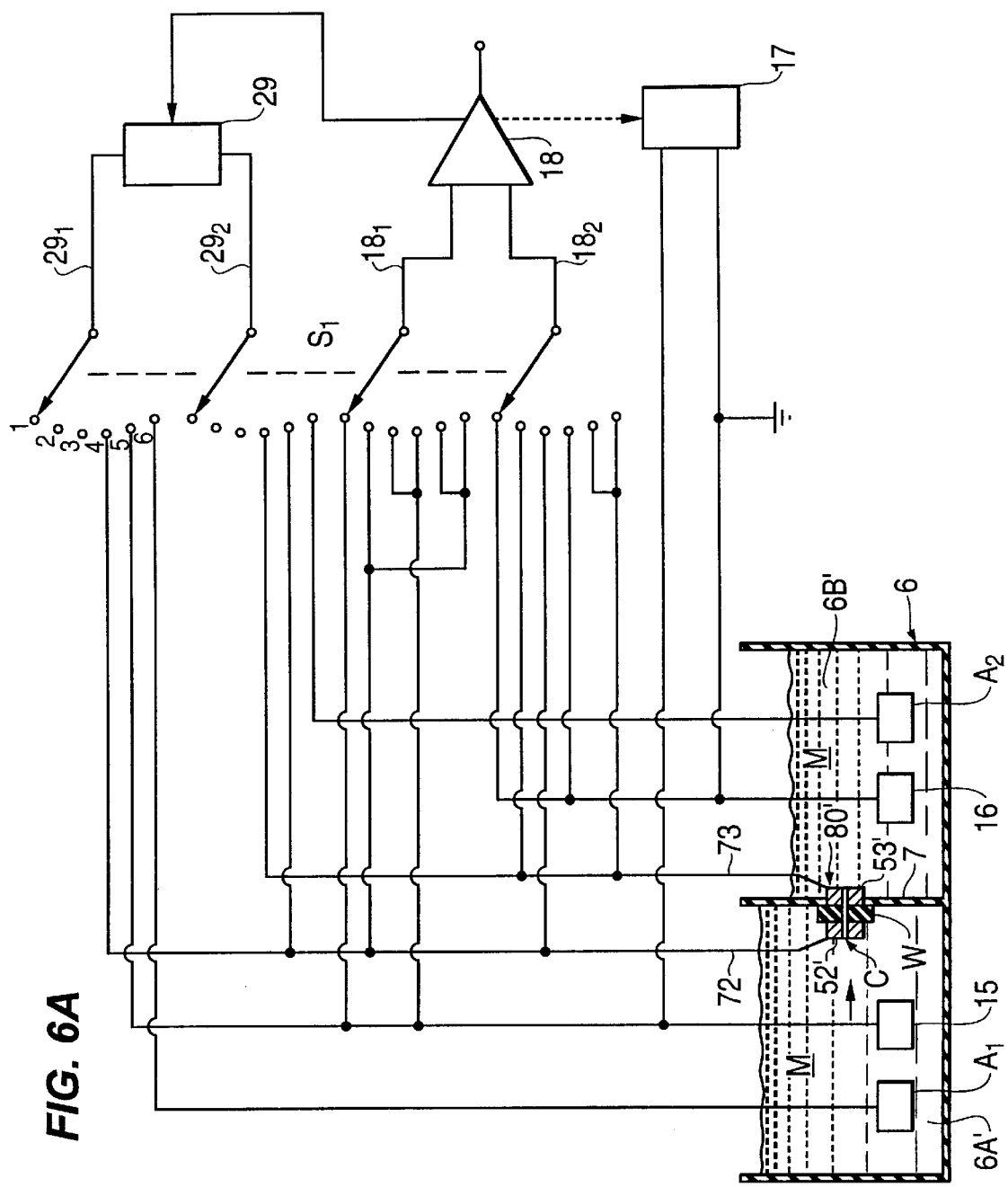
FIGS. 6A and 6B illustrate the FIG. 6 apparatus adapted to a respective first and second implementational type according to the invention.
Figure 6B:
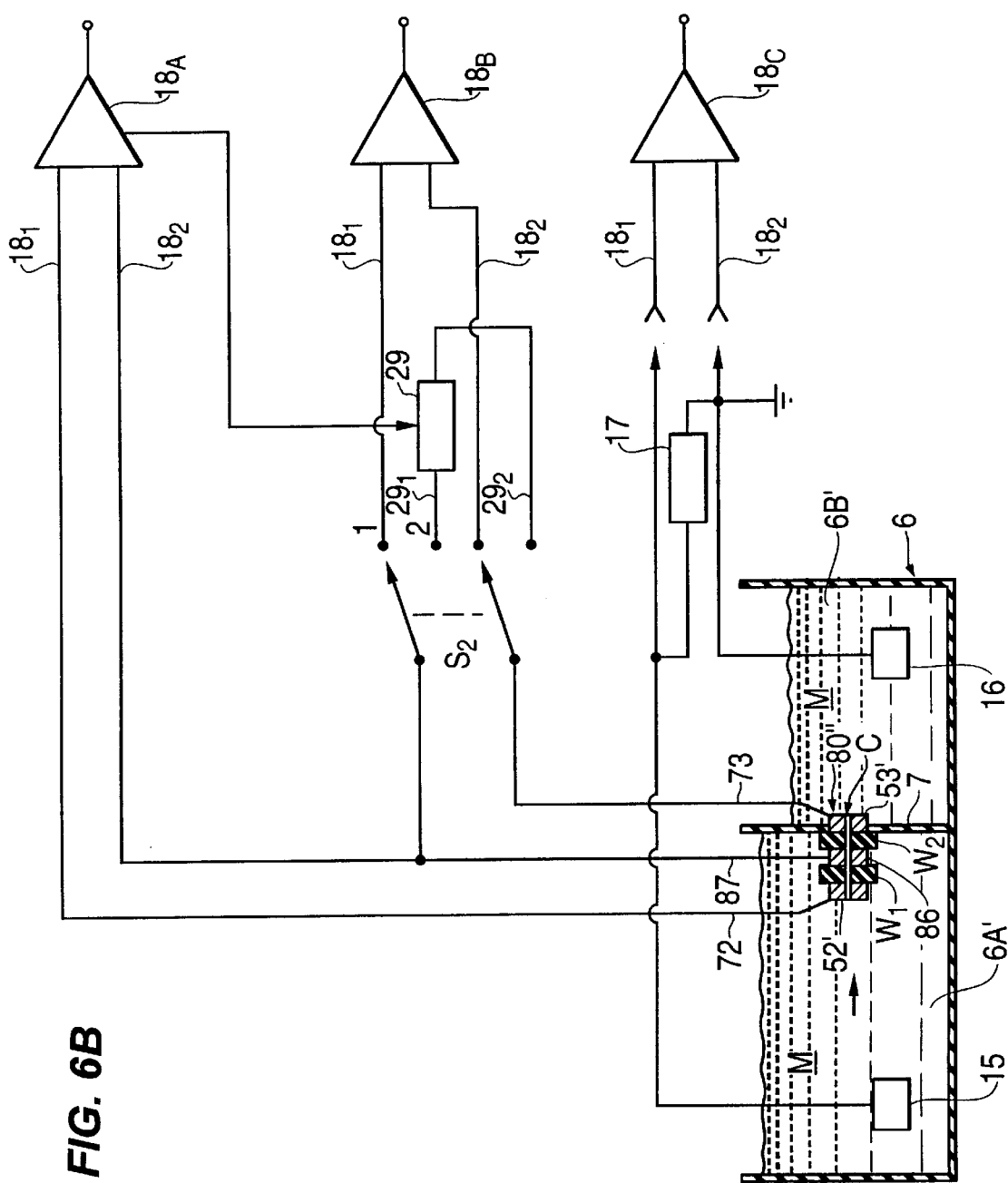

The novel functional properties of volumeter conduit C in FIGS. 6, 6A, and 6B originate in the aforementioned axial variation in axisymmetric resistivity through the material of which the volumeter assembly (e.g., 50' in FIG. 6) is constructed. Volumeter conduits incorporating field-amending characteristics may be embodied in numerous dissimilar constructions. Because the resistivity of elements 52' and 53' must be less than that of the particle-suspending medium M, because the wall 30' of conduit C must be substantially smooth in the hydrodynamic sense, and because volumeter assembly 50' is desired to be a simple device substantially substitutable for conduit wafer W of FIG. 1, it is preferred that FIG. 6 volumeter assembly 50' be constructed from solid material. The characterizing attribute of volumeter assembly 50' is the axial variation in the axisymmetric resistivity through the solid material about the axis of the intended transpiercing conduit C. The combination of axial variation in effective resistivity and hydrodynamic smoothness in wall 30' through the solid material composing volumeter assembly 50' is preferably achieved by appropriately inducing suitable resistivity gradients in the material, transpiercing the volumeter assembly at an appropriate site to form a through-hole, and then appropriately finishing the through-hole to generate the hydrodynamically smooth wall 30' defining conduit C. As will be apparent to those skilled in the appropriate arts, volumeter assemblies incorporating the inventive concepts may be embodied by a variety of techniques in a broad range of forms and materials. The aforementioned resistivity variation may be either made to occur through the solid material about the axis of the intended transpiercing conduit C, e.g., Embodiment 3, or made to occur by the appropriate selection of the individual solid elements 61, 52', and 53' prior to their assembly into volumeter assembly 50', e.g., Embodiments 2 and 4 though 8. In the latter case it is generally preferable that the elements be conjoined in the aforementioned manner prior to transpiercing, although it may be preferable in the case of large-diameter conduits for the elements to be individually transpierced to a smaller diameter, followed by finishing of the conduit in the conjoined elements to the desired conduit diameter.

Regardless of the implementation, it is most important that the conduit C be fluidically continuous and hydrodynamically smooth throughout its length. Due to the need for hydrodynamic smoothness, less preferable are construction methods which rely on either assembly of individual elements prefinished to the final conduit dimensions or use of various mechanical methods for locating and maintaining the elements in their working positions. Although a volumeter assembly 50' may be made to constitute wall 7 in FIG. 6 (e.g., see Embodiment 8), for constructional reasons conduit C is preferably provided in a volumeter assembly 50' of more convenient dimension and form. Similarly, a discord or cylindrical form is generally preferable, and it is also preferable that the axis of conduit C be substantially co-axial with that of volumeter assembly 50'. For ease of manufacture, it is preferred that all transverse surfaces of elements 51, 52', and 53' be planar, but other design considerations may require that individual elements be made to have other substantially axisymmetric surface geometries, to which any contiguous surfaces are made complementary, e.g., as indicated in FIG. 7. Individual elements 51, 52', and 53' can be given a wide variety of geometries, some of which can secondarily augment the field-amending properties of the conduit assembled therefrom. Within broad limits the external geometry of elements 52' and 53' is not critical to their primary functions and may be adapted to provide specific characteristics of the new volunteer assembly, e.g., flow matching through a trumpet shape for entry element 52' as in Embodiment 6 or causing element 52' or 53' to constitute part of a containment vessel. In addition, the lateral extent of elements 52' and 53' enables yet other design freedom which will be discussed in connection with Embodiments 4 and 5.

The material used to form elements 51, 52', and 53' is not critical to their primary functions in volumeter assembly 50' and so may be chosen to provide volunteer characteristics required by a particular application. Numerous implementations of the new volumeter are thus possible, of which some will be better suited for use in certain analyses or with particular particle/liquid systems. Element 51 is required to have an electrical resistivity substantially greater than that of the particle-suspending medium M and is preferably made from a dielectric such as ruby, sapphire, alumina, beryllia, synthetic quartz, or other material suited to a given application. However, as discussed in Embodiment 7, element 51 may also be made from a lossy dielectric such as a conductive glass, a conductive ceramic, or a type of conductive polymer or plastic, the resistivity of which is effectively greater than that of the suspending medium M but less than that of the aforementioned dielectrics. Elements 52' and 53' are required to have resistivities substantially less than that of the suspending medium M and are preferably metals or alloys from the platinum group or conductive ceramics such as certain titanium, tungsten, or silicon carbides. Some applications may benefit from use of metals such as gold, silver, titanium tantalum, tungsten, or their various alloys. Still other applications may benefit from use of nickel, copper, or their alloys, either as a metal or as a cement comprising one of these metals infiltrated into the microstructure of a ceramic such as alumina. Yet other applications may benefit from use of glassy carbon. Elements 52' and 53' need not be of the same material, and some applications of the new volumeter assembly may benefit from a judicious mismatch in one or more material properties. Generally, the materials are preferably homogeneous, but inhomogeneous materials may be preferable in specific applications. As discussed in Embodiment 5, elements 52' or 53' may be formed from one material and coated or plated with another material in order to provide combinations of material properties unobtainable with the individual materials. Some of the above advantages are achieved through the use of more-resistive materials, as for example ones whose resistivity is less than, but approximates, that of the liquid medium M in which the particles are suspended.

Electrically conductive paths 72 and 73 may be formed by a variety of methods known in the arts and are preferred to be insulated. It is not required that both field-amending elements 52' and 53' be provided a respective conductive path 72 or 73, nor is it required that both said field-amending elements be present, in a given embodiment of volumeter assemblies 50' according to the invention. It is important that the area around the junction of conductive path 72 or 73 to respective field-amending element 52' or 53' be thoroughly protected from any potential adverse effects of suspending medium M, particularly corrosion. Preferably, the complete volumeter assembly 50' is caused to have a protective envelope, e.g. by potting in an insulating epoxy so that conduit C is unaffected. A more substantial protective envelope may be provided as is known in the electronic art, e.g., masking the area of elements 52' and 53' surrounding the openings of conduit C it is desired to be uninsulated, sputter-coating the assembly with an appropriate thickness of dielectric material such as silicon dioxide, and removing the material over the areas of the field-amending elements to be left uninsulated.

The novelty of the present invention substantially originates, both directly and indirectly, in the unique field-amending volumeter conduit C common to each of the embodiments which will be described. The volumeter assemblies of the present invention incorporate field-amending conduit C of the related application, but are distinguished therefrom through the further use of thick field-amending elements as electrodes. As was elaborated in "SUMMARY OF RELATED APPLICATION", Conduit C differs from prior-art volumeter containing electrodes in several important distinctions. Firstly, prior-art conduit structures incorporating similarly located thin metallic electrodes are distinguished against in discussion related to FIGS. 3 and 4, on the basis of their disadvantageous electric-field distributions; specifically, with conduit C of volumeter assemblies 50', the electric field in the medium M adjacent to the entry and exit of such conduits can be made substantially homogeneous (e.g., see FIG. 7). Secondly, the axial extents of field-amending elements 52' and 53' are minimally those establishing a desired level of isolation between the external electric fields in the suspending liquid and the internal ambit fields of the conduit sensitive zone(s); these elements preferably have axial extents at minimum equal to those of the effective ambit electric fields of the functional Coulter conduit, further distinguishing against prior-art conduit structures incorporating similarly located conductive electrodes or elements intentionally made thin in order to minimize their effect on the electric field. Thirdly, in field-amending conduit C the axial extent of the entry field-amending element 52' may be selectively increased above the minimal value to enable development of quasi-laminar flow, thereby permitting independent optimization of the effects of the electric and hydrodynamic fields on particle pulses; such effects are not recognized in the prior conduit art. Therefore, field-amending elements 52' and 53' are clearly distinguished from similarly located thin electrodes of whatever form in the prior art, despite the fact that in the present invention said elements are also used as electrodes. Novel properties of conduit C provide the apparatus of FIGS. 6, 6A, and 6B with many of the advantages of the related application. The aforementioned, and other, advantages substantially accrue to apparatus comprising appropriate adaptations of any volumeter assembly discussed in the above referenced application.

In accordance with the present invention, implementations of a first type of the FIG. 6 apparatus are characterized by volumeter assemblies 50' derived from those of the related application by making operative electrical connection to at least one element of lesser resistivity, e.g., respective FIG. 5 element 52 or 53, whereby such element may also function as an electrode. Thus, in one form volumeter assembly 50' in FIG. 6 is substantially identical to field-amending volumeter assembly 50 in FIG. 5, but as shown in FIG. 7, it is distinguished from the FIG. 5 volumeter assembly 50 by electrically conductive paths 72 or 73 provided to at least one of its field-amending elements 52' or 53'. When appropriately provided with such conductive paths, derivations of any of the field-amending volumeter embodiments of the related application may be adapted to use as volumeter assembly 50' in FIG. 6, and FIGS. 7 through 12 illustrate a variety of such adaptations, discussed in Embodiments 2 through 9. In each of said figures, the corresponding construction of the related application (incorporated herein in entirety by reference) is appropriately provided with electrically conductive paths to at least one of the field-amending elements to form a volumeter assembly 50'. Although the construction, geometry, or materials each (or all) may differ among the several resulting volumeter assemblies 50', all provide substantially the same novel properties in electric and hydrodynamic fields in the vicinity of conduit C. According to the invention, all said volumeter assemblies 50' are adapted to apparatus operating according to the Coulter principle and requiring more than two functional terminals for practical implementation. Examples include such apparatus adapted to characterization methods incorporating potential sensing and active control of field intensities in one or more portions of the particle suspension passing through volumeter conduit C. Apparatus examples comprising such volumeter assemblies are illustrated in FIG. 6A and discussed in Embodiments 10 through 17 and 25. To indicate the substantial functional equivalence of the several volumeter embodiments, volumeter assembly 50' of FIG. 6 has been replaced in FIG. 6A by volumeter assembly 80' having a single sensitive zone.

Also in accordance with the present invention, implementations of a second type of the FIG. 6 apparatus are characterized by volumeter assemblies derived from those of the related application in the aforementioned manner and further made to have multiple sensitive zones. To illustrate, the FIG. 7 volumeter assembly 50' may be appropriately augmented by at least one pair of further FIG. 7 elements 52' and 51 or 51 and 53', each added field-amending element being provided an operative electrical connection whereby it may also function as an electrode. As discussed in Embodiments 18 through 20, such integrated tandem-conduit forms of volumeter assembly 50' thus comprise at least two sensitive zones, each preferably similar to Z' in FIG. 7, and are adapted to apparatus providing time-sequential characterizations or operations on particles passing through conduit C thereof. Apparatus examples comprising such volunteer assemblies are illustrated in FIG. 6B and discussed in Embodiments 21 through 25. To indicate the functional similarity of the different volumeter embodiments, volumeter assembly 50' of FIG. 6 has been replaced in FIG. 6B by volumeter assembly 80'' having a double sensitive zone.

EMBODIMENT 2

Volumeter assembly 50' in FIG. 7 may be implemented through mechanical assembly and joining of discrete components into a composite solid assembly composed of individual elements having appropriate unequal but substantially uniform individual resistivities. In an embodiment of particular applicability for volumeter assemblies comprising large conduits (e.g., D ≧0.400 mm, approximately), element 51 may be a convenient disc perform of highly resistive ceramic powder which is proportional in axial thickness to the desired conduit length according to the intended manufacturing technique. The axial length L of element 51 is most preferably 0.50 to 2.5 times D. Elements 52' and 53' are inset into complementary concavities in element 51, to conveniently provide the desired axial conduit length L in a structure of acceptable mechanical strength. Preferably, high-resistivity element 51 is formed of alumina of appropriate grain size and purity, and elements 52' and 53' are made of an appropriate cement (e.g., alumina infiltrated with nickel or other metal appropriate to the intended application) or one of the conductive ceramics (e.g., titanium carbide). Elements 52' and 53' may be shaped as the spherical segments shown in FIG. 7, or they may be flat discs or other axisymmetric geometries to which the form of the highly resistive central element 51 is adapted. Axial lengths $L_1$ and $L_2$ of elements 52' and 53' are most preferably a minimum of four times the intended diameter D of conduit C, and the diameter of these elements at the surface of element 51 preferably is approximately five times the conduit diameter D. Complementary elements 51, 52', and 53' may be molded (e.g., by injection processes), sintered, finished to form if necessary, and joined (e.g., by appropriate brazing methods or through use of appropriate metalfilled adhesives) prior to transpiercing and finishing volumeter assembly 50' to the desired conduit diameter D and lengths $L_1$ and $L_2$ as known in the ceramics-processing or conduit-wafer arts. Preferably, field-amending conduit C will have a constant circular cross-section and be co-axial with volumeter assembly 50'. The outer circumferential surface of volumeter assembly 50' may be finished as appropriate. Some combinations of materials may permit unfired preforms to be assembled and sintered to form volunteer assembly 50'.

Elements 52' and 53' of volumeter assembly 50' in FIG. 7 may also be either preformed of one of the metallic conductors and appropriately affixed into concavities in element 51 or formed in place therein, e.g., through use of an appropriate metallic-filled adhesive or paint. For example, discs of 1.0 mm thickness may be prepared from a convenient rod of 99.5% purity alumina having grain size in the 0.003 to 0.005 mm range, and centered spherical concavities approximately 0.40 mm deep by 1.0 mm in segment diameter at the surface of the disc are prepared on each side of the discs as is known in the ceramics arts. Each concavity in such resultant element 51 may be either filled with gold-filled adhesive and cured, or given repeated coats of a platinum-filled paint such as used in forming electrodes on glass and fired, according to the appropriate protocol to form a slightly protruding conductive deposit in each concavity. Each disc may then be lapped flat on each surface to form elements 52' and 53', transpierced through the center of the disc, and the through-holes finished to form hydrodynamically smooth circular conduit C having, e.g., D=0.200 mm, $L=L_2\tilde{=}0.200$ mm, and $L_1$=0.400 mm. Care is required to achieve the desired thickness in elements 52' and 53' without creating voids in the conductive deposits or causing the deposits to break away from element 51 during processing.

An example was given in Embodiment 1 of electrically conductive paths forming the operative connection between sensing portion 19 of aforesaid high-impedance circuitry 18 and field-amending elements 52' and 53' of volumeter assembly 50'. Preferably, the junctions of conductive paths 72 and 73 to respective FIG. 7 elements 52' and 53' are appropriately protected from any degrading influence of suspending medium M, e.g., by covering with insulating epoxy 76, and electrically conductive paths 72 and 73 are insulated by an appropriate respective insulating material 74 and 75. For greater durability, other methods known in the integrated-circuit art may be used to facilitate electrical connections to field-amending elements 52 and 53, e.g., metalization of connective lands from said elements across the respective surfaces of element 51 to connective aids formed therein.

It is important that field-amending conduit C be finished (if not formed) after volumeter assembly is formed, so that wall 30' defining the conduit is hydrodynamically smooth. In some applications, volumeter conduits resulting from such implementations may benefit from making element 51 from a lossy ceramic as discussed in Embodiment 7, from providing element 52' a shaped inlet as discussed in Embodiment 6, or from coating or plating the conductive preforms for elements 52' and 53' to provide a combination of material properties not available with the base material as discussed in Embodiment 5.

EMBODIMENT 3

In another embodiment according to FIG. 7, a volumeter assembly 50' of particular applicability for small conduits (e.g., preferably circular, with D≦0.010 mm, approximately) may be constructed virtually, from a single material, by using suitable doping methods to induce an appropriate resistivity profile. At the site intended for forming the through-hole defining field-amending conduit C, the electrical resistivity of an appropriate solid substrate may be made to effectively vary through the thickness thereof, e.g., to define a central delimited region of high electrical resistivity (approximately equal in thickness to the intended conduit diameter) which is contiguously bounded by distal regions of substantially lesser electrical resistivity (approximately equal in thickness to one to three times the intended conduit diameter). For example, suitable impurity doping methods as known in the semiconductor art may be used to create regions 52' and 53' of substantially lesser resistivity which intersect the surfaces on opposite sides of an intrinsic semiconductor (e.g., silicon) substrate 51 to form exposed regions of diameter approximately five times the conduit diameter. The individual volumeter assemblies 50' may be prepared therefrom and provided with an individual hydrodynamically smooth conduit C as is known in the relevant arts. Delimiting boundaries 54 and 55 in this embodiment are virtual and may be diffuse, rather than discrete as indicated in FIG. 7, but may be made substantially distinct as is known in the integrated-circuit art. The exposed surfaces of regions 52' and 53' must be electrically uninsulated, and all exposed surfaces of volumeter assembly 50' made to be compatible with the liquid medium used to suspend the particles. This embodiment offers advantages for forming and protecting not only electrically conductive paths 72 and 73 but their junctions to elements 52' and 53'.

EMBODIMENT 4

In above embodiments the lesser-resistivity elements or regions of volumeter assembly 50' are incorporated within the volume envelope of high-resistivity element 51. For mid-range conduit diameters, volumeter assembly 50' may include a pair of electrically conductive collars, each comprising a disc of electrically conductive material having a central opening therein, attached to a dielectric disc of convenient diameter having a central through-hole of suitable dimension. With reference now to FIGS. 8A and 8B, the high-resistivity region of volumeter assembly 50' is preferably a traditional Coulter conduit wafer W, i.e., a ruby or sapphire wafer containing a central circular conduit 10' as described in aforementioned U.S. Pat. Nos. 2,985,830 or 3,771,058. Dimensions of the Coulter conduit wafer W and its geometric conduit 10' may be selected according to the intended application, e.g., appropriate dimensions for leukocyte characterization include a conduit diameter D=0.100 mm in a ruby wafer 4.0 mm in outer diameter and L=0.075 mm in thickness. The uninsulated lesser-resistivity elements of the field-amending conduit 50' may preferably be circular collars 52' and 53' made of a platinum alloy or a conductive ceramic such as titanium carbide. Each collar 52' or 53' has a respective central opening 58 or 59 which is dimensioned and shaped to precisely conform to the conduit orifices 33 and 34 of the selected Coulter conduit wafer W. Collar openings 58 and 59 are congruently arranged with respect to the orifices 33 or 34 of the Coulter conduit, and the collars 52' and 53' are so joined to conduit wafer W that the conduit formed by the collar openings 58 and 59 and the Coulter conduit 10' reliably functions hydrodynamically as one smoothly continuous conduit C. Elements 52' and 53' may be joined to conduit wafer W by, e.g., vacuum brazing, commercial epoxy or metal-filled adhesives, use of appropriate glass frits, etc., according to the application. Electrically conductive paths 72 and 73 may comprise runs of such metal-filled epoxy or enamel extended a convenient distance onto the lateral surfaces of wafer W. Depending on the assembly method and sequence chosen, smallgauge wires insulated with appropriate insulation may be fixtured in place and connected to collars 52' and/or 53' or such conductive extensions during the curing or firing process. Some advantages of the invention may be obtained if only a single conductive path is provided, e.g., preferably 72 to field-amending collar 52'. The complete volumeter assembly is preferably treated to protect the electrical junctions and conductive paths from harsh environments.

Preferably, field-amending conduit C is formed in situ, and the respective length $L_1$ or $L_2$ of each collar 52' or 53' along the conduit C should at least approximate the diameter D of the traditional Coulter conduit; most preferably, said lengths may be one to three times the diameter of conduit 10' in Coulter conduit wafer W. whereby the electric and hydrodynamic fields of the traditional volumeter conduit are advantageously amended in the aforementioned manner.

The outer diameter of the collar discs may preferably be at least approximately five times the diameter D of the traditional Coulter conduit 10', in which case the electric field in the vicinity of field-amending conduit C is substantially like that for Embodiment 2, shown in FIG. 7. However, this dimension is not critical to the primary functions of the collars and may be chosen to satisfy secondary functions, as will be discussed. Although shown as planar, the configuration of the outer face of collars 52' or 53' in FIG. 8B may be any configuration suited to the application of the particular volumeter assembly. Although the collars are shown as of constant cross-section, the internal longitudinal section of either collar 52' or 53' may be chosen to provide a secondary function as discussed in Embodiment 6 or either of the collars 52' or 53' may form part of a mounting device or of a liquid containment vessel. Some advantages of the invention may be obtained through the less preferable use of only a single collar arranged at either the entry orifice or exit orifice 34 of the traditional Coulter conduit 10' in conduit wafer W, as discussed in Embodiment 9.

Although description of specific detailed sequences for making a prototypic integrated structure now follows, many other such sequences will suggest themselves to one skilled in the appropriate arts. In general, any mounting, fixing, and assembly method known in the conduit art may be appropriately adapted, including any of those described in other embodiments herein. Thus, the discussion to follow is intended to be illustrative only, and not in any sense limiting.

A prototypic embodiment consists of discs of platinum 2.5 mm in outer diameter, one 0.20 mm thick (52' in FIGS. 8A and 8B) and one 0.10 mm thick (53' in FIG. 8B), centered one per side on a ruby disc (W in FIGS. 8A and 8B) 4.0 mm in outer diameter and 0.122 mm in thickness. The platinum discs are attached to the ruby disc with two-part epoxy adhesive according to the manufacturer's instructions. The cured assembly was perforated and finished to form a circular volumeter conduit having a functional Coulter conduit of diameter D=0.100 mm and L/D=1.22, as is known in the art of making Coulter wafers. A wire approximately 0.095 mm in diameter was placed through conduit C to keep it clear, and electrically conductive paths 72 and 73 comprised 28-gauge insulated wire about 12 inches long attached to field-amending collars 52' and 53' with platinum-filled commercial epoxy. The completed volumeter assembly is mounted with a two-part epoxy adhesive onto an aperture tube according to aforementioned U.S. Pat. No. 2,985,830 from which the conventional Coulter wafer (W in FIG. 1) has been removed. The 0.20 mm platinum collar 52' forms the entry side of conduit C. Care was taken to ensure that the epoxy both sealed the opening in the aperture tube and insulated the junction of electrically conductive paths 72 and 73 to collars 52' and 53'. The wires comprised in conductive paths 72 and 73 were trimmed to length and connected to a miniature connector attached to the upper part of the aperture tube with epoxy. Additional epoxy was used to attach the two wires to the outside of the lower body of the aperture tube. The protective wire was then removed from conduit C, which was checked under a microscope prior to test. Except for the axial extent of thick field-amending collars 52' and 53' (and the absence of insulative elements 43 and 44 in FIG. 3), the completed tube thus resembles similar tubes illustrated in aforementioned U.S. Pat. Nos. 3,924,180 and 4,019,134.

Other examples consist of discs of titanium carbide 3.2 mm in outer diameter, either 0.10 mm thick or 0.20 mm thick and Coulter wafers of different thicknesses. The component elements were finished to desired thickness, individually perforated to form an unfinished conduit approximately 0.090 mm in diameter, assembled as will be disclosed, and then conduit C of the integrated conduit structure was finished to a diameter D=0.100 mm. In these examples, a titanium carbide element 0.20 mm thick (52') and one 0.10 mm thick (53') were centered on and affixed to each side of ruby wafers W 4.0 mm in outer diameter and of various thicknesses 0.005 mm≦L=0.200 mm. In these steps a steel wire 0.088 (±0.001) mm was used to align the unfinished conduits and keep them clear of the commercial two-part epoxy used to conjoin the three said components. Once the epoxy had cured, conduits C of the complete volumeter assemblies 50' were then finished to a diameter of 0.100 mm as is known in the Coulter conduit art, and conductive paths 72 and 73 were provided by attaching small-gauge insulated wire to elements 52' and 53', respectively, with conductive paint. The electrical resistance between conductive paths 72 and 73 was checked, to detect inadvertent electrical cross-connections; a brass wire approximately 0.100 mm in diameter was placed through conduit C; and volumeter assembly 50' was mounted with two-part commercial epoxy adhesive onto an aperture tube in the aforementioned manner. (By these methods aperture tubes having conduit L/D=0.05 have been made; below L/D≈0.03, signal-to-noise ratios and assembly fragility become prohibitively unfavorable, plus little further practical decrease in coincidence volume can be achieved.)

Volumeter conduits including such collars may benefit from making element 51 from a lossy ceramic as discussed in Embodiment 7, from providing element 52' a shaped inlet as discussed in Embodiment 6, or from coating or plating the conductive preforms for elements 52' and 53' to provide a combination of material properties not available with the base material as discussed in Embodiment 5.

Figure 9:
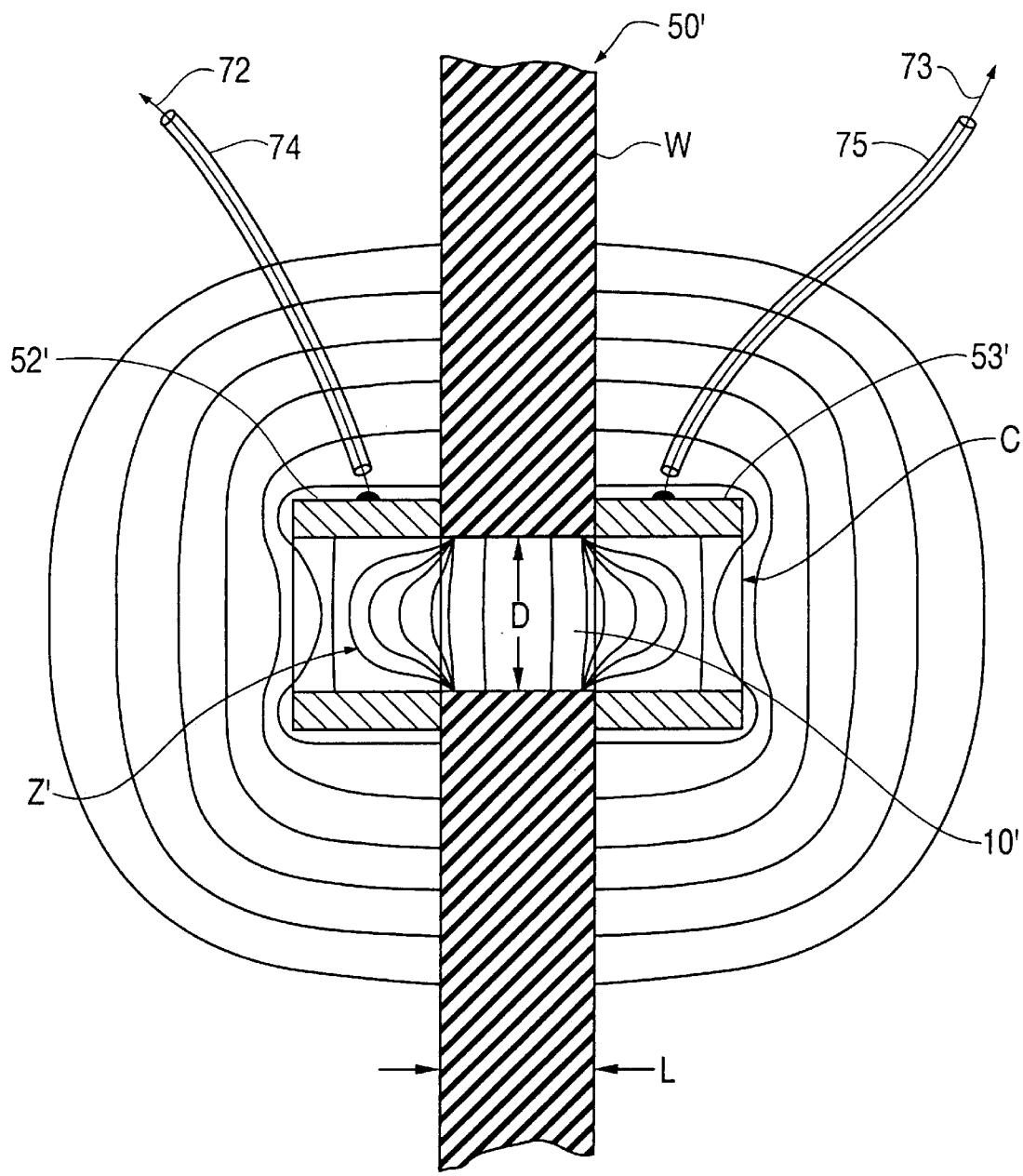
FIGS. 9–12 illustrate longitudinal sections of alternative embodiments of volumeter assembly adapted to use in the apparatus of FIG. 6A.

In FIG. 9 is illustrated a volumeter assembly 50' similar to that of FIGS. 8A and 8B, except that conductive collars 52' and 53' have outer diameters only slightly larger (e.g., =1.5D) than diameter D of functional conduit 10' in conduit wafer W. Such tubular collars provide the internal particle-sensitive zone Z' and the primary hydrodynamic advantages of the large-diameter elements 52' and 53' in FIGS. 7, 8A, and 8B, but a different distribution of the electric field and less favorable secondary fluidic properties external to field-amending conduit C. Consequently, for use in the apparatus of FIG. 6A, the outer collar diameters may be selected to provide electrical characteristics not available with traditional Coulter conduits. For example, the outer diameters of collars 52' and 53' may be chosen to passively control electric field uniformity and current density in the particle-suspending liquid near the entry to conduit C, in which case it is preferred that the outer diameter of the collars should be at least several times greater than the conduit diameter D, as in FIGS. 7, 8A, and 8B.

Alternatively, impedances for DC and AC excitation currents may be decoupled, since the former depends only on the physical dimensions of functional conduit 10' and the properties of the particle-suspending liquid M, whereas the latter also depends on the lateral dimensions of collars 52' and 53' and the dielectric properties of the conduit wafer W used to form conduit C. Thus, the DC impedance for volumeter assembly 50' in FIGS. 8A and 8B is not significantly different from that of volumeter assembly 50' in FIG. 9, but the AC impedances of the two volumeter assemblies differ substantially, due to the different cross-sectional area of respective collar-pair 52' and 53' contacting conduit wafer W. For use in the apparatus of FIG. 6B, embodiments comprising tubular collar are less preferable due to the additional constructional complexity arising therefrom.

EMBODIMENT 5

Figure 10:
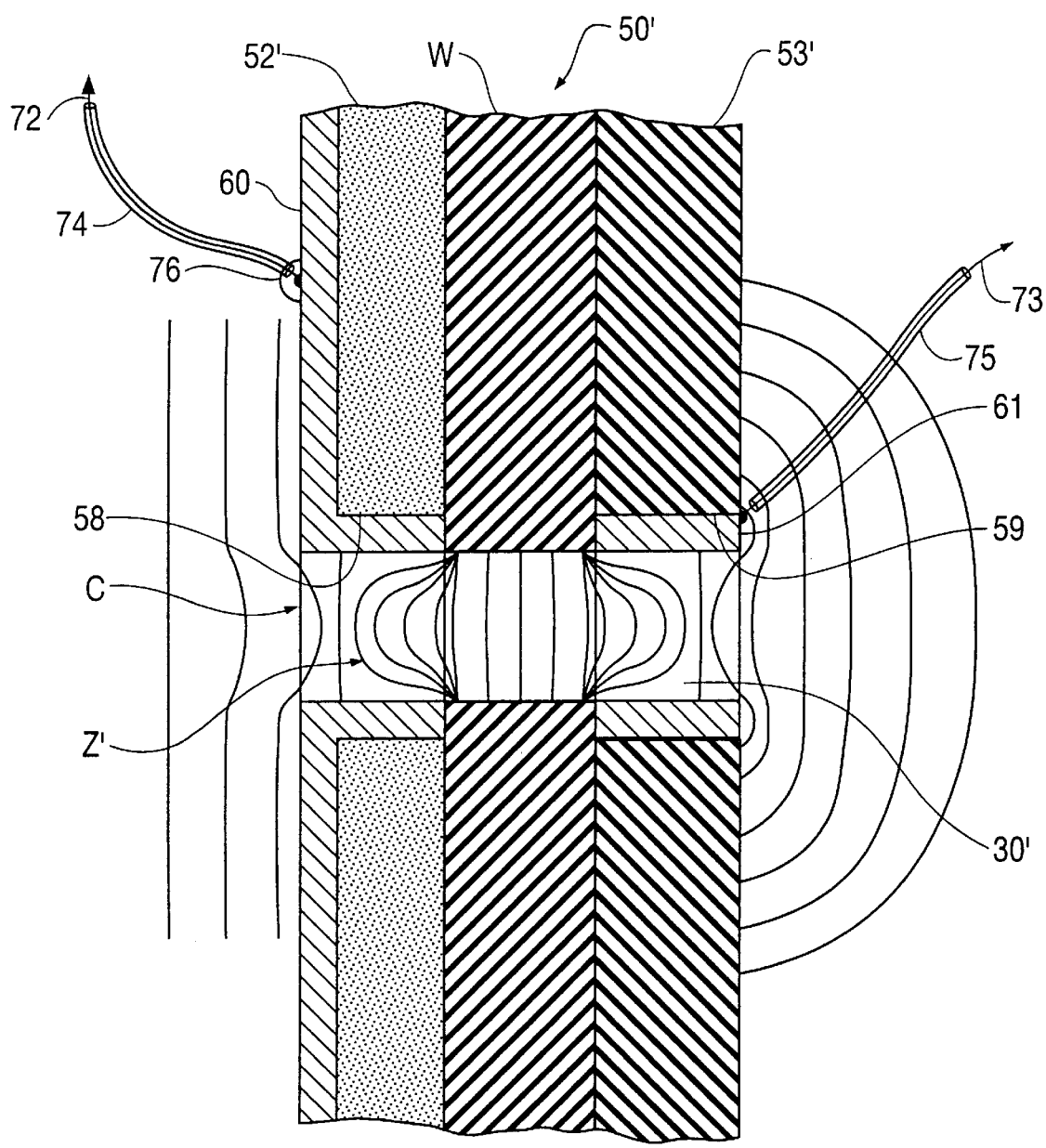

Although the above embodiments comprise low-resistivity elements made of homogeneous conductive materials, in general these elements (e.g., 52' or 53' in FIGS. 7, 8B, and 9) may be formed from one material and coated or plated with another material in order to provide combinations of material properties unobtainable with the individual materials. In FIG. 10 is illustrated a volumeter assembly 50' which incorporates two such collars 52' and 53' attached to Coulter conduit wafer W so as to form hydrodynamically smooth conduit C. Conductive coating or plating 60 over the outer face and through opening 58 of collar 52' permits it to establish the electric field distribution seen with homogeneous conducting elements 52' or 53' in FIGS. 7 or 8B. Conductive coating or plating 61 through opening 59 of dielectric collar 53' permits it to establish the electric field distribution seen with the tubular homogeneous conducting collars 52' or 53' in FIG. 9, but without the unfavorable secondary hydrodynamic properties. Such coatings or platings 60 and 61 preferably produce an effective resistivity in those portions of wall 30' surrounded by elements 52' and 53' which is less than that of the suspending medium M. Some applications may benefit from metalization (e.g., platinization) of elements 52' and 53', while others may benefit from similar use of a conductive oxide (e.g., of tin or indium). The resulting sensitive zone Z' within field-amending conduit C is substantially identical to those in FIGS. 7 and 9, irrespective of the direction of suspension flow through conduit C in FIG. 10 or of whether both collars are identically the form of either collar 52' or 53' in FIG. 10. However, the external electric field distributions in the particle-suspending liquid M between the collar faces and excitation electrodes will depend on the area of conductor exposed to the suspending medium.

The AC impedance of conduit C in FIG. 10 will depend on the electrical properties of the material used to make the collars, particularly so for collars (e.g., collar 52') coated or plated on a lateral surface. In principle, the field characteristics required in the field-amending conduit C may be provided by such collars made of either a dielectric or a conductive material, i.e., either a conductive or an insulative ceramic plated to form metallic coating 60 in order to provide a particular combination of electrical conductivity and chemical stability. However, the AC impedance of volumeter assembly 50' comprising a pair of collars of the form of collar 52' in FIG. 10 will vary significantly, depending on whether such collars are made from a conductive or insulative material. If the collars are made from a dielectric material, then the AC impedance of conduit C will also depend on the dielectric properties of the material unless a conductive material is used to join the collars to conduit wafer W, i.e., brazing or use of a metal-filled adhesive will yield an impedance similar to that given by a homogeneous conductive collar of similar dimensions. In general, such collars may be formed of any material providing the desired combination of electrical and physical properties. Other surfaces of such collars may be selectively coated or plated to provide a selection of electrical characteristics, if at least the wall of collar openings 58 and 59 is made conductive with a suitable coating or plating. The latter structure, in which both collars 52' and 53' are coated or plated only through their respective openings 58 and 59, is the minimal embodiment of the field-amending concept and may in principle be realized by appropriately coating or plating portions of conduit 10' in conduit wafer W having L/D≧3. Advantage may be taken of coatings in the form of 60, by appropriate extension to provide an attachment for electrically conductive path 72 and to facilitate protecting its junction to element 52', e.g., with epoxy 76. Coatings in the form of 61 are less preferable, e.g., due to the inconvenience of providing conductive path 73 and protecting its junction thereto. However, in embodiments of the invention not requiring operative electrical connection to exit field-amending element 53', such coatings may be practical.

In some applications, volumeter conduits resulting from such implementations may benefit from making element 51 from a lossy ceramic as discussed in Embodiment 7 or from providing element 52' a shaped inlet as discussed in Embodiment 6.

EMBODIMENT 6

The axial distribution of conduit cross-sections of the collars may be designed to provide desired electric or hydrodynamic distributions in the conduit ambits. For example, the total length $L_1$ of element 52' in FIGS. 7, 8B or 10 required to attain a given modal particle trajectory may be shortened without loss of hydrodynamic benefits if a radiussed or trumpet-shaped entry region is provided on its entry edge. Such a shaped entry is known in the art to provide improved flow properties through the conduit (U.S. Pat. No. 3,739,258), but in Coulter volumeter conduits shaped entries degrade pulse characteristics and are difficult to repeatably produce in the usual dielectric materials. However, in the field-amending conduit pulse characteristics may be made independent of the shaped entry, since the particle-sensitive zone is decoupled from the hydrodynamic length of conduit C. Thus, if a straight conduit section of minimum length $L_7$=D is interposed between conduit wafer W and the shaped entry 62 in conductive element 52' as shown in volumeter assembly 50' of FIG. 11, the hydrodynamic benefits of the shaped entry may be gained without degrading pulse characteristics. Preferably, shaped entry 62 is made to have a longitudinal profile of exponential shape, but it may be given a toroidal form with radius approximately D/2 or greater. Such shaped entries are comparatively simple to form in many of the conductive materials useful in making elements 52' or 53', and due to averaging in the developing laminar flow, imperfections in such shaped entries 62 are less significant than with shaped entries in prior-art conduits formed in dielectric materials. In some applications, volumeter conduits resulting from such implementations may benefit from making element 51 from a lossy ceramic as discussed in Embodiment 7 or from coating or plating the preforms for elements 52' and 53' to provide a combination of material properties not available with the base material as discussed in Embodiment 5.

Figure 11:
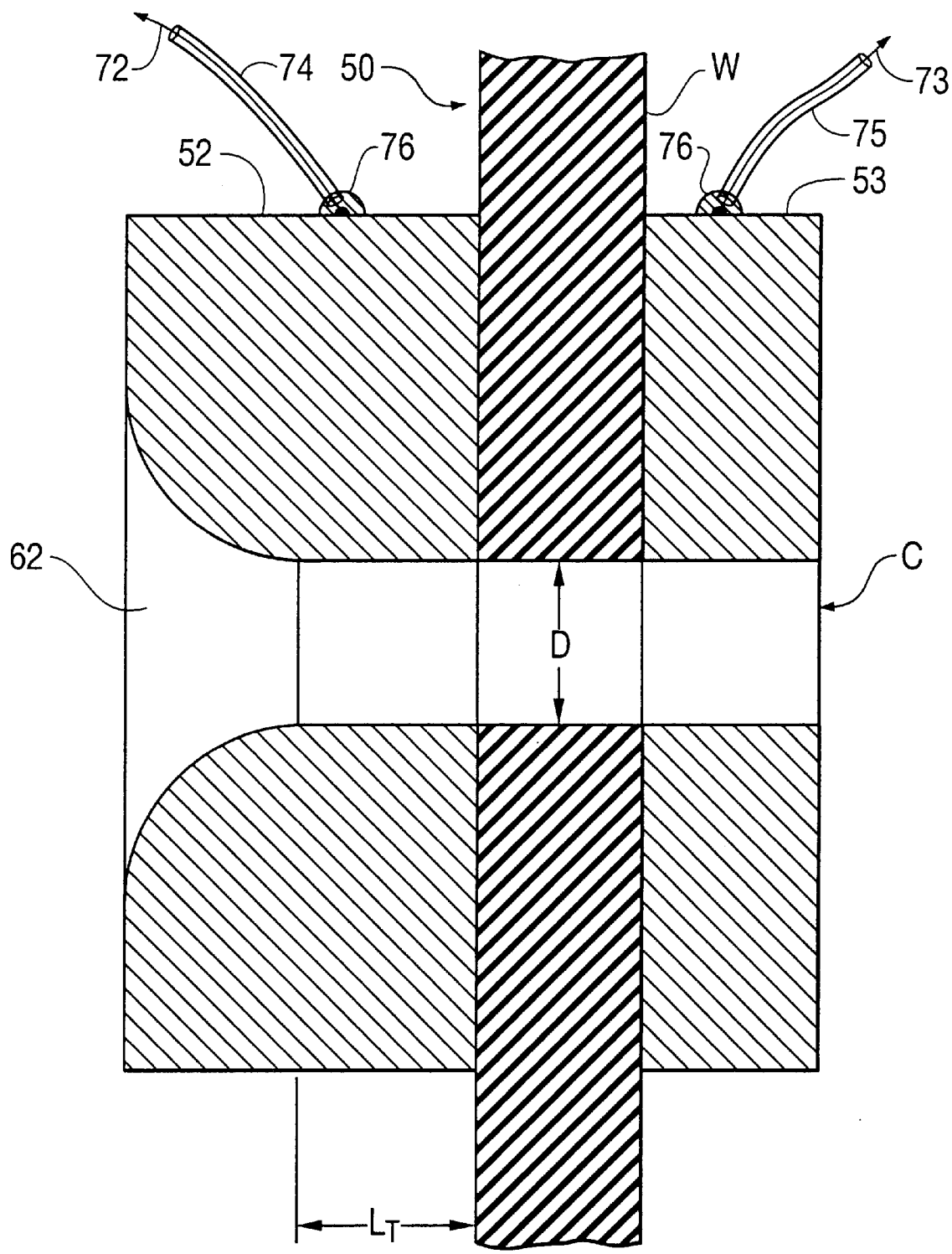

In FIG. 11, a preferred form of electrically conductive paths 72 and 73 to respective elements 52' and 53' is illustrated, wherein insulated wire is joined to the field-amending collars (e.g., with a platinum-filled epoxy) and the ends of respective insulating materials 74 and 75 are captured in a bead 76 of insulating epoxy compatible with said insulating materials.

EMBODIMENT 7

Although the above embodiments comprise a high-resistivity element (e.g., 51 in FIG. 7 or W in FIGS. 8B, 9, 10, and 11) made of an excellent dielectric material, in general the high-resistivity element in any of the preceding embodiments may be made of a lossy dielectric such as a conductive glass, a conductive ceramic, a type of conductive polymer or plastic, or other such material. The resistivity of such lossy dielectric is preferably substantially greater than that of the particle-suspending medium M but less than that of, e.g., ruby, alumina, or quartz. An appropriate choice of such material may be useful in further shaping the electric field within the functional Coulter conduit, e.g., 10' in the FIG. 7 volumeter assembly 50', to improve field homogeneity. Use of lossy dielectrics as the high-resistivity element may be particularly beneficial in conduits C for which L≦D, whereby the poor pulse-amplitude development of such conduits may be improved. Assembly and joining methods must be compatible with the specific lossy dielectric selected for the high-resistivity element. Benefits of lossy dielectrics may also be provided by depositing a thin metallic layer, e.g., gold or nickel, of controlled resistivity through the conduit of a traditional Coulter conduit wafer and incorporating said wafer as wafer W in e.g., FIGS. 8B, 10 or 11.

EMBODIMENT 8

Figure 12:
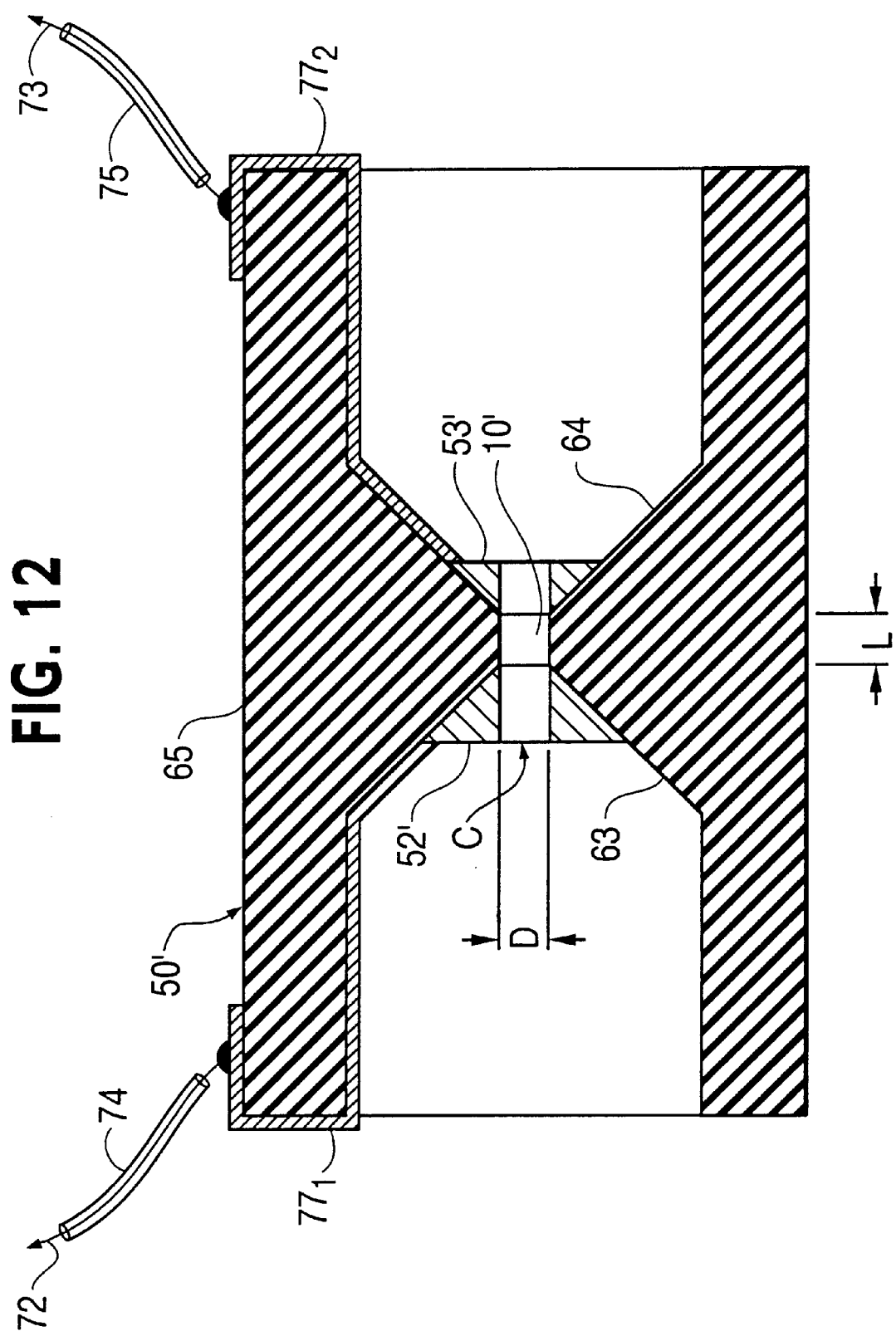

According to the alternative embodiment illustrated in FIG. 12, the volumeter assembly 50' is constructed as a flow cell of the type described in U.S. Pat. Nos. 3,628,140 or 4,515,274. The high-resistivity element in such structures is typically an integral part of flow cell 65. Such flow cells are usually made from an optically transparent material such as fused quartz, synthetic silica, sapphire or beryllia and are typically used in apparatus combining the Coulter principle with optical sensing modalities. Examples include the apparatus of U.S. Pat. No. 4,791,355 to Wallace H. Coulter and C. M. Rodriguez; U.S. Pat. No. 5,125,737 to C. M. Rodriguez and W Wallace H. Coulter; U.S. Pat. No. 5,616,501 to C. M. Rodriguez and S. L. Ledis. Such apparatus most commonly includes fluidic subsystems providing hydrodynamically focused flow. Typical volumeter conduits C are of constant circular cross-section, of a diameter D in the 0.030 mm to 0.200 mm range. Suitable collars 52' and 53' of minimal thickness at least approximating the conduit diameter D are adapted into conical cups 63 and 64 in the dielectric flow cell 65 as may be consistent with other design considerations. The thicknesses of collars 52' and 53' combine with the length L of functional conduit 10' to form hydrodynamically smooth conduit C. The distribution of the electric field is substantially similar to that in FIG. 7, with the particle-sensitive zone internal to field-amending conduit C. Collars 52' and 53' may be made of a platinum alloy or other appropriate material; if desired, collars 52' and 53' may also be inset into flow cell 65 so that the outer collar surfaces are smoothly continuous with the conical cups 63 or 64. Joining of elements 52' and 53' to flow cell 65 may be by any appropriate method, e.g., use of metal-loaded epoxies or frits, extensions 77, and $77_2$ of which may be comprised in electrically conductive paths 72 or 73 to respective collars 52' or 53'. In other implementations, holes formed through element 65 (and located as be out of any desired optical path) may be used to provide access for electrically conductive path 72 or 73 to respective field-amending collars 52' or 53'; a compatible conductive epoxy may then be used to both establish and protect the electrical junction.

Advantages of the invention may be provided volumeter assemblies comprising conduits of prismatic cross section, for example as discussed in U.S. Pat. No. 4,348,107, by incorporating appropriate collars of minimal thickness at least approximating the diagonal of the particular conduit cross section and providing operative electrical connections thereto.

Hydrodynamically focused flow may be used with field-amending volumeter conduits, e.g., to stabilize suspension flow through the sensitive zone. If hydrodynamically focused flow is used with, e.g., the field-amending flow cell of FIG. 12, element or collar 53' may not be needed since the sheath flow can be made to substantially prevent extraneous pulses from particles on recirculation trajectories. However, in many applications the length L, and entry shape of element or collar 52' may be selected (as discussed in Embodiment 6) so that acceptable performance can be achieved without use of hydrodynamically focused flow, in which case it is preferred that element or collar 53' be included in volumeter assembly 50'.

EMBODIMENT 9

Regardless of the particular embodiment, it is preferred that volumeter assembly 50' comprise both field-amending elements 52' and 53', and this is necessary if particle-sensitive zone Z' of conduit C is to be substantially symmetric about its axial midpoint. However, some advantages of the present invention may be obtained through use of only a single element 52' or 53' arranged at, respectively, the entry or exit of conduit C of volumeter assembly 50'. Thus, if the concern is reduction of histogram skewness due to particles transiting the sensitive zone near the conduit wall, element 53' could be omitted. The asymmetric ambit fields of sensitive zone Z' then resemble 31' in FIG. 7 on the entry side and 32 in FIG. 1 on the exit side; element 52' will reduce occurrence of anomalous pulses, but recirculating particles near the exit of the dual nt volumeter assembly will produce extraneous pulses and an artifactual low-volume distribution. Conversely, if the concern is elimination of the artifactual low-volume distribution due to recirculating particles, element 52' could be omitted. Then, the asymmetric ambit fields of sensitive zone Z' will resemble 31 in FIG. 1 on the entry side and 32' in FIG. 7 on the exit side; element 53' will reduce occurrence of recirculation pulses, but particles transiting the conduit of the dual-element volumeter assembly near its wall will produce histogram skewness due to anomalous pulses. These less-preferred forms represent the minimal volumeter assembly 50', wherein the volumeter structure comprises (e.g., in FIGS. 8A and 8B) the pair of elements W and 52' or the pair of elements W and 53' and the appropriate electrically conductive path 72 or 73 thereto.

It is believed that the concepts of novel volumeter assemblies 50' are now sufficiently described that, with the aid of preferred apparatus embodiments to follow, those skilled in the relevant arts will be able to fabricate apparatus suited to many novel applications of the Coulter principle. Volumeter assemblies 50' may be adapted to many known forms of apparatus incorporating the Coulter principle, including forms incorporating other sensing modalities, particle sorting, or auxiliary subsystems intended to facilitate secondary operational requirements (e.g., DC-compensation of current source 17 or portions of sensing circuitry 18 for changes in resistivity in suspending medium M). Volumeter assemblies 50' may be adapted by prior-art methods to enable simultaneous passage of a suitable suspension of particles to be characterized and an electrical excitation current through the field-amending conduit. Although excitation may be provided by voltage sources, e.g., as in aforementioned U.S. Pat. No. 2,656,508, it is preferable to use constant-current sources for current source 17, such as taught in aforementioned U.S. Pat. No. 3,259,842; the sources may be direct current, alternating current, or a combination thereof. To detect, sense, and characterize particles nearing and transiting conduit C, all Coulter apparatus requires in addition to current source 17 a set 18 of sensing circuitry such as that comprising 19, 20', and 21 in FIG. 6. Volumeter assemblies 50' may be adapted by prior-art methods to provide operative electrical connections between the field-amending elements therein and such sensing circuitry. For particle-sensing functions, it is preferable that AC-coupled sensing circuitry be used, due to the comparatively large potential shifts which may occur normally in the vicinity of volumeter assemblies.

It will be obvious to those skilled in the art of particle analysis that, due to the functional characteristics of conduit C in volumeter assemblies according to the invention, the apparatus of FIGS. 6, 6A, and 6B provides operational characteristics both more preferable and more extensive than those of similar prior-art apparatus. However, beyond the functional advantages of conduit C therein, volumeter assemblies 50' indirectly contribute further novelty to the apparatus of FIGS. 6, 6A, and 6B. One such novel aspect originates in, but is not limited to, the reduction of facilitating art required to provide acceptable accuracy in particle characterization apparatus which requires more than two terminals to develop particle-characterization data. Yet another novel aspect is the resulting flexibility and versatility afforded apparatus design, which promises to expand the particle-characterizing art, by enabling cost-effective approaches to particle characterization methods not practicable with prior art volumeter conduits.

In preceding discussion it has been indicated that there are two types of apparatus according to the invention. Volumeter assemblies 50' having a single sensitive zone are used in the first type of apparatus, and the structures in FIGS. 8A and 8B, 11, or 12 are most preferred. Operational characteristics of the first implementational type (FIG. 6A) depend upon use made of discrete electrodes, the type of electrical circuitry connected to each conductive path to field-amending elements of volumeter assembly 50', and whether electrical circuitry is connected to more than one such conductive path. Operational characteristics of a second implementational type (FIG. 6B) depend not only upon the aforementioned factors, but also upon the number of additional sensitive zones integrated into volumeter assembly 50'. As will be apparent to those skilled in the art, numerous configurations of novel apparatus incorporating the Coulter principle are thus possible according to the invention. To illustrate the range of apparatus to which volumeter assemblies of the present invention may be adapted, volumeter assembly 80 will represent any volumeter assembly incorporating the use of field-amending elements as electrodes. In view of the foregoing discussion and to facilitate clarity, with reference then to FIGS. 6, 6A, and 6B, henceforth the four following conventions are stipulated:

1. Any electrode located more than one conduit diameter D from the nearest functional Coulter conduit in volumeter assembly 80 is a discrete electrode. Such electrodes may be variously disposed within 6A' and 6B' of FIGS. 6, 6A, or 6B or connected thereto by liquid columns, including locations within or on volumeter assembly 80 greater than conduit diameter D from the nearest functional Coulter conduit therein. Such electrodes include, but are not limited to, any used to supply excitation current to volumeter conduit C (e.g., 15 and 16 in FIGS. 6, 6A, and 6B) which are preferred to be located at appreciable distance from the conduit C. Such electrodes may be auxiliary ones (i.e., $A_1$ and $A_2$ in FIGS. 6A) used to obtain signals or supply current related to aspects of apparatus function secondary to sensing and characterization of particles by the Coulter principle (e.g., U.S. Pat. No. 3,944,917).

2. The novelty of the present invention does not originate substantially in the specific types of electrical circuitry which may be operatively connected to any field-amending element associated with a particular volumeter assembly 80. Thus, in FIGS. 6A and 6B, sensing circuitry 18 comprises such appropriate forms and combinations of FIG. 6 prior-art circuitry 19, 20', and 21 and prior-art devices 22 as one skilled in the Coulter art would use to efficiently achieve the intent of a specified connection via inputs $18_1$ and $18_2$. The set 18 of conventional circuitry 19, 20', and 21 operating to detect, sense, monitor, and record particle count and characteristic data may be required in a specific electrode connection, whereas in other electrode connections display/recording devices 22 or sizing circuitry 21 may not be required. It is preferred that AC-coupled sensing circuit 19 have low input impedance compared to the conduit impedance when connected to excitation electrodes 15 and 16, but high input impedance when connected between any other pair of electrodes; in the latter case it may also be preferable that sensing circuitry 19 be a differential-input circuit. In some instances, it may be preferable that processing circuitry 20' comprise specialized pulse-processing algorithms or techniques known in the prior art.

3. Some forms of the invention in FIG. 6A require multiples of said sensing circuitry 18 and/or prior-art floating source 29 of effector current, as will be apparent to one skilled in the Coulter art. For illustrative clarity, it is stipulated that the single element of sensing circuitry 18 or source 29 shown in FIG. 6A indicates the multiplicity of such elements needed to achieve the intent of any stated connection or combination of connections. As appropriate, DC-coupled sensing circuitry or effector current sources are denoted as sensing circuitry 18' or current source 29', respectively.

4. FIGS. 6A and 6B differ from FIG. 6 in two details: a) Respective volumeter assemblies 80' and 80" in FIGS. 6A or 6B are shown as sealing an opening corresponding to opening 7A of FIG. 6, so that conduit C forms the only operative electrical and fluidic connection between compartments 6A' and 6B' of vessel 6, without the opening being specifically indicated in said figures; and b) Hydrostatic pressure, indicated by the difference in levels of liquid M in compartments 6A' and 6B' in FIGS. 6A and 6B, is used to move particle suspension through conduit C of respective volumeter assembly 80' or 80", rather than the vacuum applied to port 11 in FIG. 6. It is stipulated that said differences, introduced for illustrative clarity, do not detract from the operability of the embodiments schematized in FIGS. 6A and 6B.

Therefore, with reference now to FIG. 6A and with the aforesaid stipulations in mind, in implementations of the first type of apparatus according to the invention, either at least one input $18_1$ or $18_2$ of one sensing circuitry 18 or at least one output $29_1$ or $29_2$ of one effector current source 29 is operatively connected to at least one field-amending element 52' or 53' via an electrically conductive path (e.g., 72 or 73) provided to said field-amending elements in volumeter assembly 80' having a single sensitive zone. The other said input of a sensing circuitry 18 or output of an effector current source 29 may be operatively connected to either the other field-amending element 53' or 52' of volunteer assembly 80' via the other electrically conductive path (e.g., 73 or 72) thereto or to a discrete electrode (e.g., $A_1$ or 15; or 16 or $A_2$, respectively). The possible connection modes for said inputs of one sensing circuitry or outputs of one effector current source are summarized in Table 1, together with resulting operational characteristics for both AC-coupled (18 and 29) and DC-coupled (18' and 29') circuitry. As indicated in the first through sixth rows of Table 1, a sensing circuitry 18 may in principle to connected between any aforementioned pair of electrodes, of which connections those of Modes A through C are less preferable.

In some implementations of the first type, at least one source 29 of effector current can, by operative connection of outputs $29_1$ and $29_2$ to various pairs of electrodes, function to actively modify in at least a part of the particle suspension, the local intensity of the nominal electric field established between discrete electrodes 15 and 16 by current source 17. The portion of particle suspension affected depends upon the electrode pair chosen for connection of current source 29. As indicated in the seventh through twelfth rows of Table 1, a current source 29 may in principle also be connected between any aforementioned pair of electrodes, of which connections those of Modes D through F are less preferable. It is important that any source 29 not introduce noise into the apparatus of FIG. 6. It is preferable that any source 29 have a high inactive impedance, to minimize disturbing effects on the nominal electric field within conduit C. In general, connections of current source 29 to field-amending elements 52' or 53' (via conductive paths 72 or 73) create a potential for electrochemical artifacts (e.g., bubble generation), the effects of which must be considered when planning characterization methods based on such connections. Source 29 may be operatively connected to a sensing circuitry 18 and activated in response to a signal developed thereby in response to the passage of a particular particle through conduit C; sensing circuitry 18 used in such implementations must be designed to disregard or accommodate any significant

TABLE 1

Examples of connections between electrical connections 72 and 73 to volumeter assembly 80 and a sensing circuitry having inputs $18_1$ and $18_2$ or a current source having outputs $29_1$ and $29_2$.
The first column indicates a mode of connection; numbered modes correspond to positions of $S_1$ in FIG. 6A, whereas lettered modes are less preferred. The second and third columns indicate the connections to inputs of the sensing circuitry, and the fourth and fifth columns indicate those to the outputs of the effector source. The sixth and seventh columns indicate the operational characteristics of apparatus in which the sensing circuitry and effector source are AC- or DC- coupled, respectively.
The first through sixth rows indicate the possible connections for a single sensing circuitry connected to electrical connections 72 and 73, with no effector source present. The seventh through twelfth rows indicate the possible connections for a single effector source; illustrative connections for a single sensing circuitry are indicated for the preferred connections.
The last two rows illustrate connections for two sensing circuitry, one connected according to Mode 2 and the other according to Mode 1 or Mode 3, respectively. Other useful connections will occur to those skilled in the Coulter art.

| | Sensing Circuitry | | Effector Source | | Comments on Function | |
|---|---|---|---|---|---|---|
| Mode | $18_1$ | $18_2$ | $29_1$ | $29_2$ | AC | DC |
| 1 | 15 | 16 | None | None | Two-terminal particle sensing. | Resistance of liquid path. |
| 2 | 72 | 73 | " | " | Potential-sensing particle sizing. | Resistance of conduit C. |
| 3 | 15 | 72 | " | " | Detection of particle entry. | Potential of 72/15. |

TABLE 1-continued

Examples of connections between electrical connections 72 and 73 to volumeter assembly 80 and a sensing circuitry having inputs $18_1$ and $18_2$ or a current source having outputs $29_1$ and $29_2$.
The first column indicates a mode of connection; numbered modes correspond to positions of $S_1$ in FIG. 6A, whereas lettered modes are less preferred. The second and third columns indicate the connections to inputs of the sensing circuitry, and the fourth and fifth columns indicate those to the outputs of the effector source. The sixth and seventh columns indicate the operational characteristics of apparatus in which the sensing circuitry and effector source are AC- or DC- coupled, respectively.
The first through sixth rows indicate the possible connections for a single sensing circuitry connected to electrical connections 72 and 73, with no effector source present. The seventh through twelfth rows indicate the possible connections for a single effector source; illustrative connections for a single sensing circuitry are indicated for the preferred connections.
The last two rows illustrate connections for two sensing circuitry, one connected according to Mode 2 and the other according to Mode 1 or Mode 3, respectively. Other useful connections will occur to those skilled in the Coulter art.

| | Sensing Circuitry | | Effector Source | | Comments on Function | |
|---|---|---|---|---|---|---|
| Mode | $18_1$ | $18_2$ | $29_1$ | $29_2$ | AC | DC |
| A | 73 | 16 (or $A_2$) | " | " | Rate of particle departure. | Potential of 73/(16 or $A_2$). |
| B | 72 | 16 (or $A_2$) | " | " | Composite pulse/departure rate. | |
| C | 15 (or $A_1$) | 73 | " | " | Composite pulse/arrival rate. | |
| 4 | 15 | 16 | 72 | 73 | Pulsed field in conduit C: poration. | Compensated field in conduit C. |
| 5 | 72 | 73 | 15 | 72 | Low-insult cleaning connection. | Control of conduit potential. |
| 6 | 72 | 73 | $A_1$ | $A_2$ | Pulsed field in conduit C: poration. | Control of conduit potentials. |
| D | | | 73 | 16 | | Control of potential of 73/16. |
| E | | | 72 | 16 (or $A_2$) | | |
| F | | | 15 (or $A_1$) | 73 | | |
| 21 | 72; 15 | 73; 16 | Per need. | Per need. | Simultaneous particle-pulse streams. | |
| 23 | 72; 15 | 73; 72 | " | " | Particle sizing, with entry detection. | | artifacts introduced by subsequent operation of current source 29. Current source 29 may also be activated independently of particle presence or characteristics e.g., as may be required in a manual cleaning application.

Generally, connection modes requiring sensing (or passage of current from current source 29) between a discrete electrode and either field-amending element 52' or 53' through conduit C are least preferable (e.g., Modes B and C or E and F in Table 1).

Multiple sensing circuitry a8 or 18' (or effector current sources 29 or 29') may also be used, to provide multiple simultaneous connections to various combinations of discrete electrodes (e.g., 15, 16, $A_1$, or $A_2$) and electrically conductive paths (e.g., 72 and/or 73) to field-amending elements of volumeter assembly 80', according to desired operational characteristics.

In FIG. 6A, a six-position, four-pole selector switch $S_1$ is used to provide the six numbered connective modes of Table 1 in an illustrative apparatus according to the invention. Although it may be advantageous to provide two or more such connections in practical apparatus, the intent of FIG. 6A is not to suggest that such combinations are necessary in demonstrating inventive novelty. Rather, the intent of FIG. 6A is to illustrate the flexibility of configuration and versatility o f application possible with apparatus according to the invention. Several preferred connection modes are discussed in Embodiments 10 through 17, the first four of which do not require an effector current source 29.

EMBODIMENT 10

To demonstrate the concept of Table 1 and FIG. 6A, the preferred embodiment shown in FIG. 6 is included as Mode 2 in Table 1 and as the operational mode indicated by Position 2 of switch $S_1$ in FIG. 6A. In said switch position, inputs $18_1$ and $18_2$ of sensing circuitry 18 are operatively connected (via respective conductive paths 72 and 73) to field-amending elements 52' and 53' in volumeter assembly 80'. First current source 17 operatively connected to discrete electrodes 15 and 16 provides a nominal current through conduit C of volumeter assembly 80'. Current source 29 and auxiliary electrodes $A_1$ and $A_2$ are inactive. Potential pulsations occasioned as particles transit conduit C are sensed and recorded by sensing circuitry 18 as discussed in Embodiment 1.

Preferably, volumeter assembly 80' is one discussed in Embodiment 4 (viz., FIGS. 8A–8B). In contrast to prior-art conduit structures (e.g., those of aforementioned U.S. Pat. Nos. 3,924,180; 4,019,134; 4,224,567; or 4,484,134) which require two insulating elements (e.g., 43 and 44 in FIG. 3), the FIGS. 8A–8B volumeter structure requires none and so may be more readily fabricated. Elimination of such insulating elements also eliminates the voltage-dividing action of liquid columns in the through-holes therein, thereby improving the signal-to-noise ratio of pulse streams generated by particles transiting conduit C of the FIG. 6A apparatus. Moreover, conduit C does not produce the disadvantageous ambit electric fields produced by the variant Salzman structure of FIG. 4.

The novel four-terminal potential-sensing apparatus of FIG. 6 or this embodiment is similar in configuration to that described by Salzman et al. (aforementioned U.S. Pat. No. 5 3,924,180) and comprising the conduit structure of FIG. 3. However, no prior-art apparatus comprises volumeter assembly 80' including field-amending elements 52' and 53' or field-amending conduit C therein. Consequently, no prior-art apparatus affords the aforementioned functional or commercial advantages deriving therefrom.

EMBODIMENT 11

In some forms of the invention it is preferred that sensing circuitry 18 be AC-coupled, have low input impedance compared to the conduit impedance, and have inputs $18_1$ and $18_2$ operatively connected to discrete electrodes 15 and 16 as in the prior two-terminal art. In another preferred embodiment (not illustrated), each field-amending element 52' or 53' of volumeter assembly 80' in FIG. 6A is operatively connected (via electrically conductive path 72 or 73) only to respective discrete electrodes 15 or 16 with a high-quality capacitor of appropriate value. By this novel method discrete electrodes 15 and 16 may be physically located away from conduit C as preferred to avoid electrochemical effects of DC excitation, but be functionally close to conduit C through action of said capacitors and field-amending elements 52' and 53'. The signal-to-noise ratio of particle pulse-streams resulting from particles transiting conduit C may be thereby improved, due to the short-circuiting effect of the low-impedance path thus provided for electrical noise coupled into suspending medium M in compartments 6A' or 6B', respectively. This provides a novel apparatus which, while two-terminal with respect to sensing circuitry 18 and current source 17, is effectively four-terminal with respect to pulse signal-to-noise characteristics. Insofar as AC pulse-response is concerned, the operative connection is via electrically conductive paths 72 and 73 to the field-amending elements in volumeter assembly 80'; however, with respect to DC current, this embodiment corresponds to Mode 1 in Table 1. If appropriate, only one capacitor may be so connected or said capacitors may be replaced by low-noise filter circuitry, as is known in the electronic art.

If in this embodiment no operative pulse connection is provided between said field-amending elements 52' or 53' and respective discrete electrodes 15 or 16, Mode 1 as illustrated by Position 1 of switch $S_1$ in FIG. 6A obtains in fact. This is functionally the apparatus of the related application, but with the disadvantage that non-functioning conductive paths 72 and 73 to field-amending elements 52' and 53' must be appropriately isolated to prevent their introducing electrical noise into conduit C of volumeter assembly 80'. If no operative connection is made via either said electrically conductive path to field-amending elements 52' or 53' in volumeter 80', the resulting apparatus is not according to the present invention.

EMBODIMENT 12

However, if either one input $18_1$ or $18_2$ of a first sensing circuitry 18 or one output $29_1$ or $29_2$ of an effector source 29 is operatively connected to at least one of field-amending elements 52' or 53' in volumeter assembly 80', inputs $18_1$ and $18_2$ of a second sensing circuitry 18 may be operatively connected to discrete electrodes 15 and 16 according to the invention. Thus, in a not her preferred sensing embodiment corresponding to Mode 21 in Table 1, inputs $18_1$ and $18_2$ of a first sensing circuitry 18 are connected via electrically conductive path s 72 and 73 to field-amending elements 52' and 53' in volumeter assembly 80', and inputs $18_1$ and $18_2$ of a second sensing circuitry 18 are connected to pairs of discrete electrodes such as 15 and 16, $A_1$ and $A_2$, 15 and $A_2$, or $A_1$ and 16. The two sensing circuitry operate simultaneously, and particles transiting conduit C produce a pulse stream via each sensing circuitry 18. Each of the two particle plus streams represent one of the aforementioned forms of improved Coulter apparatus, whereby comparative measurements on the same particles may be made by the two methods. There is no requirement that each sensing circuitry 18 be responsive in a given frequency band, i.e., one may respond to a DC component and the other to a radio-frequency component of the excitation current provided by current source 17.

Although similar apparatus configurations are described in the aforementioned publications concerning the Leif and Salzman structures, the prior-art apparatus did not comprise field-amending volumeter assembly 80' of the present invention. Consequently, it could not afford the aforementioned functional or commercial advantages deriving therefrom,

EMBODIMENT 13

In a detection embodiment, inputs $18_1$ and $18_2$ of a sensing circuitry 18 in FIG. 6A are operatively connected (via electrically conductive path 72) to field-amending element 52' of volumeter assembly 80' and to discrete electrode 15. This embodiment corresponds to Mode 3 in Table 1 and Position 3 of switch $S_1$ in FIG. 6A. For said connection, particles approaching conduit C generate a signal which permits detection of particle entry into conduit C; while such signal does not permit characterization of the particle, it can facilitate analytic processes applied to a pulse stream, e.g., by providing an anticipatory timing signal. Thus, in Mode 23 in Table 1, a first sensing circuitry 18 connected in the aforementioned manner may trigger a sampling circuit so as to optimally sample the pulse sensed by a second sensing circuitry 18, inputs $18_1$ and $18_2$ of which are operatively connected as described in Embodiment 10.

Such anticipatory signals are known in the art, and the novel apparatus of this embodiment is similar in configuration to one described by Feier (aforementioned U.S. Pat. No. 43161,690). However, the Feier apparatus comprises a conduit structure which is difficult to duplicate and which affords no field-amending properties. Consequently, for typical conduit dimensions the coincidence volume of the functional conduit in the prior-art structure is substantially the same as for the FIG. 1 Coulter conduit 10, or about three times that of conduit C of the invention. Further, because there is no field-amending element in the prior-art structure, hydrodynamic flow through its conduit is quasi-uniform, compared to quasi-laminar in conduit C, with attendant skewness in the volumetric distribution. Finally, recirculating particles may further degrade volumetric accuracy, since they have access to the exit ambit field. Consequently, t he prior-art apparatus does not afford the aforementioned functional or commercial advantages deriving from the present invention.

Some benefits of the invention may be obtained if field-amending element 53' and electrically conductive path 73 are omitted from volumeter assembly 80', but with the limitations discussed in connection with Embodiment 9. However, these modes provide improved constructional simplicity and data accuracy, compared to the Feier apparatus.

The analogous reverse connection, Mode A in Table 1, may be useful in indicating the exiting rate of a particle or the potential of field-amending element 53' relative to a discrete electrode (e.g., that of 72 relative to 16 or $A_2$), but is less preferable than Modes 1 through 3. Because of the composite nature of signals given by connective Modes B and C, the latter are least preferable of the six possible connections of a sensing circuitry 18.

In some forms of the invention it is preferred that a current source 29 be operatively connected to one of various pairs of electrodes disposed in compartments 6A' and 6B' of vessel 6 in FIG. 6, including excitation discrete electrodes in and 16, auxiliary discrete electrodes $A_1$ and $A_2$, and those formed by field-amending elements 52' and 53'. It may be preferred that second current source 29 be operatively connected to a portion of sensing circuitry 18 to be responsive to a particular aspect of particle characteristics or apparatus operation.

EMBODIMENT 14

In a preferred active embodiment, particles passing through conduit C of integrated volumeter assembly 80' in FIG, 6A are sensed by sensing circuitry 18 connected as described in Embodiment 10, and characteristics of the signal thereby provided are used to activate effector source 29 via an operative connection thereto. The outputs $29_1$ and $29_2$ of source 29 are operatively connected to auxiliary discrete electrodes $A_1$ and $A_2$ immersed in medium M, whereby the nominal electric field in functional conduit 10' is modified or controlled in a desired manner. The resulting embodiment corresponds to Mode 6 in Table 1 and Position 6 of switch $S_1$ in FIG. 6A. Particles transiting conduit C of volumeter assembly 50' can be sensed with the aforementioned benefits and advantages.

In an AC-coupled form of the embodiment, current source 29 and auxiliary discrete electrodes $A_1$ and $A_2$ may be optimized to the specific application. The connection of a pulse current source 29 to discrete electrodes $A_1$ and $A_2$ permits improved dynamic response in the field-modification loop, independently of the characteristics of excitation current source 17 and excitation electrodes 15 and 16. Further improvement is facilitated by two functional aspects of volumeter assembly 80', permitting more flexibility in operational protocols. Firstly, the small size of field-amending elements 52' and 53' reduce the input capacity seen by sensing circuitry 18, thereby improving dynamic response in the sensed particle characteristic. Secondly, the improved resolution and accuracy in particle characterization provided through the function of the field-amending elements permits more precise definition of the criteria by which current source 29 is activated. Among other uses, this embodiment may be adapted to porate biological cells, determine cell membrane breakdown, or estimate cell fragility as is known in the two-terminal art (e.g., U.S. Pat. No. 4,220,916), but without the dynamic limitations demonstrated in the prior-art apparatus.

In an alternative form of the embodiment, DC-coupled sensing circuitry 18' may be connected in the aforementioned manner, whereby the electrical resistance of conduit C may be monitored, and current source 17 is made operatively responsive to a control signal from sensing circuitry 18', as indicated by the dashed connective line in FIG. 6A. Thus, according to Mode 4 in Table 1, the nominal excitation current between discrete electrodes 15 and 16 may be controlled in a desired manner. If the operative connection constitutes a linear feedback circuit, such forms of the new apparatus can accommodate changes in resistivity of the suspending medium M or substitution of conduit C of another geometry (e.g., aforementioned U.S. Pat. Nos. 4,019,134 or 4,224,567). In contrast to prior-art implementations of such compensation methods, volumetric characterizations of particles of improved accuracy can be provided, due to the field-amending elements and conduit C of volumeter assembly 80'.

EMBODIMENT 15

Some applications of the cell poration and breakdown art many benefit from the fixed relationship between the field-amending elements in said volunteer assembly 80', which can provide more precise control over the electric field to which the selected cells are subjected. In this embodiment, inputs $18_1$ and $18_2$ of a sensing circuitry 18 in FIG. 6A are operatively connected between discrete electrodes 15 and 16, and outputs $29_1$ and $29_2$ of pulse source 29 are operatively connected to field-amending elements 52' and 53' in volumeter assembly 80' via electrically conductive paths 72 and 73. This embodiment demonstrates one use of Mode 4 in Table 1, as illustrated by Position 4 of switch $S_1$ in FIG. 6A.

The characteristics of particles transiting conduit C are sensed and processed by sensing circuitry 18, and current source 29 is operatively connected to sensing circuitry 18. Current source 29 is responsive to a portion of the processing capability therein, e.g., a discriminate function or algorithm, and is activated according to one or more selected cell characteristics as determined by processing elements of sensing circuitry 18. In one example, the particles are biological cells suspended in medium M containing a fluorescent dye; cells having a selected characteristic as determined by sensing circuitry 18 and porated by response of source 29 can be loaded with sufficient dye to enable their subsequent optical detection by known methods. As known in the art, appropriate pulse voltages can leave the cells viable. In addition to the improved volumetric accuracy provided in the characterization data, the larger surface of field-amending elements 52' and 53' (in comparison to thin electrodes in prior-art integrated conduit structures) may enable greater poration currents before onset of electrochemical artifacts. How ever, surface area of the field-amending elements is sufficiently smaller than that of excitation electrodes 15 and 16 that transient response of effector-current waveforms can be significantly faster. If repeatability of the poration or breakdown condition is critical, hydrodynamically focused flow may further confine suspension flow through conduit C.

If pulse voltage is appropriately increased, this embodiment can be used to cause cell disruption by dielectric breakdown, rather than comparatively benign poration.

EMBODIMENT 16

In a preferred cleaning embodiment, corresponding to Mode 5 in Table 1 and Position 5 of switch $S_1$ in FIG. 6A, outputs $29_1$ and $29_2$ of a source 29 are operatively connected to a discrete electrode, e.g., discrete electrode 16, and (via electrically conductive path 72) to field-amending element 52' in volumeter assembly 80'. Activata on of current source 29 may be in response to faulty pulse data from sensing circuitry 18, provided via an operative connection therebetween, or by manual means. For example, in U.S. Pat. No. 4,412,175 to F. D. Maynarez; U.S. Pat. No. 4,450,435 to B. D. James; and U.S. Pat. No. 4,775,833 to E. Roos and Wallace H. Coulter, methods are shown of deriving an alarm signal responsive to a dirty or clogged conduit, where by a pulse generator forming source 29 may be activated (i.e., U.S. Pat. No. 3,963,984 to Wallace H. Coulter). In thi s embodiment, cleaning current is directed to the surface most likely to accumulate debris, so cleaning action occurs at the site of greatest potential debris accumulation, without passage of a cleaning current through conduit C. This contrasts to prior-art cleaning methods, wherein a high-density electrical current passes through the conduit, with a significant potential for damaging the conduit structure without fully cleaning the conduit.

Some benefits of the invention may be obtained if field-amending element 53' and electrically conductive path 73 are omitted from volumeter assembly 80', but with the limitations discussed in connection with Embodiment 9.

EMBODIMENT 17

In FIG. 6A, a DC-coupled source 29' operatively connected between a discrete electrode 15 and (via electrically conductive path 72) to field-amending element 52' of volumeter assembly 80' (Mode 5 in Table 1), or between discrete electrode 16 and (via electrically conductive path 73) field-amending element 53' (Mode D in Table 1), may be used in active field-control methods, wherein a field potential gradient in the vicinity of volumeter assembly 80' is driven to some desired value in response to a field measurement made by a sensing circuitry 18'. Other operative connections of a source 29' (e.g., that of aforementioned U.S. Pat. No. 4,972,137) will occur to those skilled in the art, as will different combinations of operative connections for a sensing circuitry 18' and a source 29'. In general, Modes E and F in Table 1 are the least preferable of the six connections possible for effector current sources 29 or 29'.

EMBODIMENT 18

In some forms of the invention it is preferred that volumeter assembly comprise additional sensitive zones. In a general form of Embodiments 2 through 9 comprising sensitive zones, volumeter assembly 80 preferably comprises high-resistivity elements ($W_1 \ldots, W_i \ldots, W_n$) and lesser-resistivity elements (52'; $86_1, \ldots, 86_{(n-1)}$; 53') contiguously arranged in alternating sequence and each said element being provided a through-hole, the individual through-holes being made to form a fluidically continuous and hydrodynamically smooth conduit C through volumeter assembly 80.

High-resistivity elements are designated $W_i$ ($1 \leq i \leq n$), irrespective of their geometry, to indicate their functional analogy to conventional Coulter wafers W, and have an electrical resistivity substantially greater than that of the medium M in which the particles to be characterized are suspended. It is preferred that all high-resistivity elements $W_i$ have axial extents in the range 0.3 and 2.5 times the diameter D of conduit C. It is not required that all high-resistivity elements $W_i$ have identical axial extents, and some preferred embodiments comprise elements $W_i$ having unequal axial extents.

Each lesser-resistivity element (52'; $86_1 \ldots, 86_{(n-1)}$; 53') has an electrical resistivity substantially less than that of the medium M in which the particles to be characterized are suspended, and each said element is provided a respective electrically conductive path, e.g., a small insulated wire, (72; $87_1, \ldots, 87_{(n-1)}$; 73) thereto. Lesser-resistivity elements 52' and 53' are at least substantially equal to the diameter of conduit C in their axial extent along conduit C, and provide the aforementioned field-amending function. It is not required that said axial extents be equal, nor is it required that any of respective elements (52'; $86_1 \ldots, 86_{(n-1)}$; 53') have an axial extent identical to that of any other element. Internal lesser resistivity elements ($86_1 \ldots, 86_{(n-1)}$) of volumeter assembly 80 may function either as additional field amending elements if greater in axial extent than diameter D of conduit C or as prior-art electrodes if said extent is substantially less than D.

Except for the axial extent of field-amending elements 52' and 53', integrated tandem-conduit volumeter assembly 80 may thus resemble in configuration ones described by W. R. Hogg in aforementioned U.S. Pat. No. 4,438,390, assigned to the assignee of the present application. Substantial novelty of the present invention originates in the function of novel field-amending elements 52' and 53', whereby the distribution of both the fluidic and electric fields in the vicinity of and through conduit C is advantageously improved, as described in the related application. However, further novelty accrues through the design flexibility provided by judicious choice of internal elements $86_j$ having various axial extents. Some applications of volumeter assemblies according to the invention may benefit from use of internal field-amending elements $86_j$ having axial extents in the range between one to ten times diameter D of conduit C, while others may more advantageously employ internal thin electrodes $86_i$. When all elements 52', 53', and ($86_1 \ldots, 86_{(n-1)}$) have substantially identical axial extents, the electrical properties of the plural sensitive zones of volumeter assembly 80 can be made substantially identical, whereby the characteristics of particles as consecutively determined in the sequential sensitive zones may be compared. The greater similarity in pulses provided by volumeter assemblies having multiple sensitive zones according to the latter embodiment would greatly simplify the associated processing required to implement the pulse-averaging methods described in the '390 patent.

In contrast to sequential-conduit art (e.g., aforementioned U.S. Pat. Nos. 3,793,587 and 4,525,666), internal elements ($86_1 \ldots, 86_{(n-1)}$) between high-resisfivity elements ($W_1 \ldots, W_n$) enables continuous fluidic flow in volumeter assembly 80, so that such volumeter assemblies comprising multiple sensitive zones do not introduce fluidic gaps with their attendant jetting flow. Indeed, used as field-amending elements said elements enable selection of a particular fluidic regime of the continuously developing laminarity throughout conduit C of such volumeter assemblies, by modal methods taught in the related application. As one consequence, there is no need for the complex fluidic subsystems and structures required in prior-art apparatus; as another, novel methods seem possible for study of particle properties inaccessible with present methods. In further contrast to sequential-conduit art, aforementioned differences in electric-field distributions (e.g., when FIG. 1 is compared with FIG. 7) result in substantially smaller coincidence volumes in each of the multiple sensitive zones. In addition, the known locational geometry of elements comprised in volumeter assembly 80 greatly simplifies methods for correlating activities within the individual sensitive zones.

In general, any of the volumeter assemblies described in preceding embodiments may be fluidically aligned with another volumeter assembly, so that the composite conduit therethrough is hydrodynamically continuous and smooth, to form such an integrated tandem-conduit structure. The various said elements may be composed of any material appropriate to individual function and the intended application of volumeter assembly 80. When appropriate insulated electrically conductive paths to $87_j$ are also provided to each internal element $86_j$ in said integrated tandem-conduit structures, novel volumeter assemblies 80 having multiple tandem sensitive zones are formed. Specific examples are discussed in Embodiments 19 and 20, wherein volumeter assembly 50' of either FIG. 11 or FIG. 12 is so adapted to comprise two or three such sensitive zones, respectively. As a convention, these will be indicated by 80" or 80''', respectively, whereas volumeter assemblies having one sensitive zone are indicated by 80'. In these examples, element $86_j$ serves in its field-amending role and is so designated.

Integrity of the various electrical junctions to elements within volumeter assembly 80 is critical, and appropriate methods as known in the art must be used to guarantee that these are both electrically insulated and protected from degrading influences of suspending medium M. The complete volumeter assembly 80 is preferably sealed against action of medium M, with only the desired portions of the several field-amending elements left exposed to electrical contact.

Less preferably, either of the external field-amending elements 52' or 53' may be omitted, with the limitations discussed in connection with Embodiment 9.

EMBODIMENT 19

Figure 13:
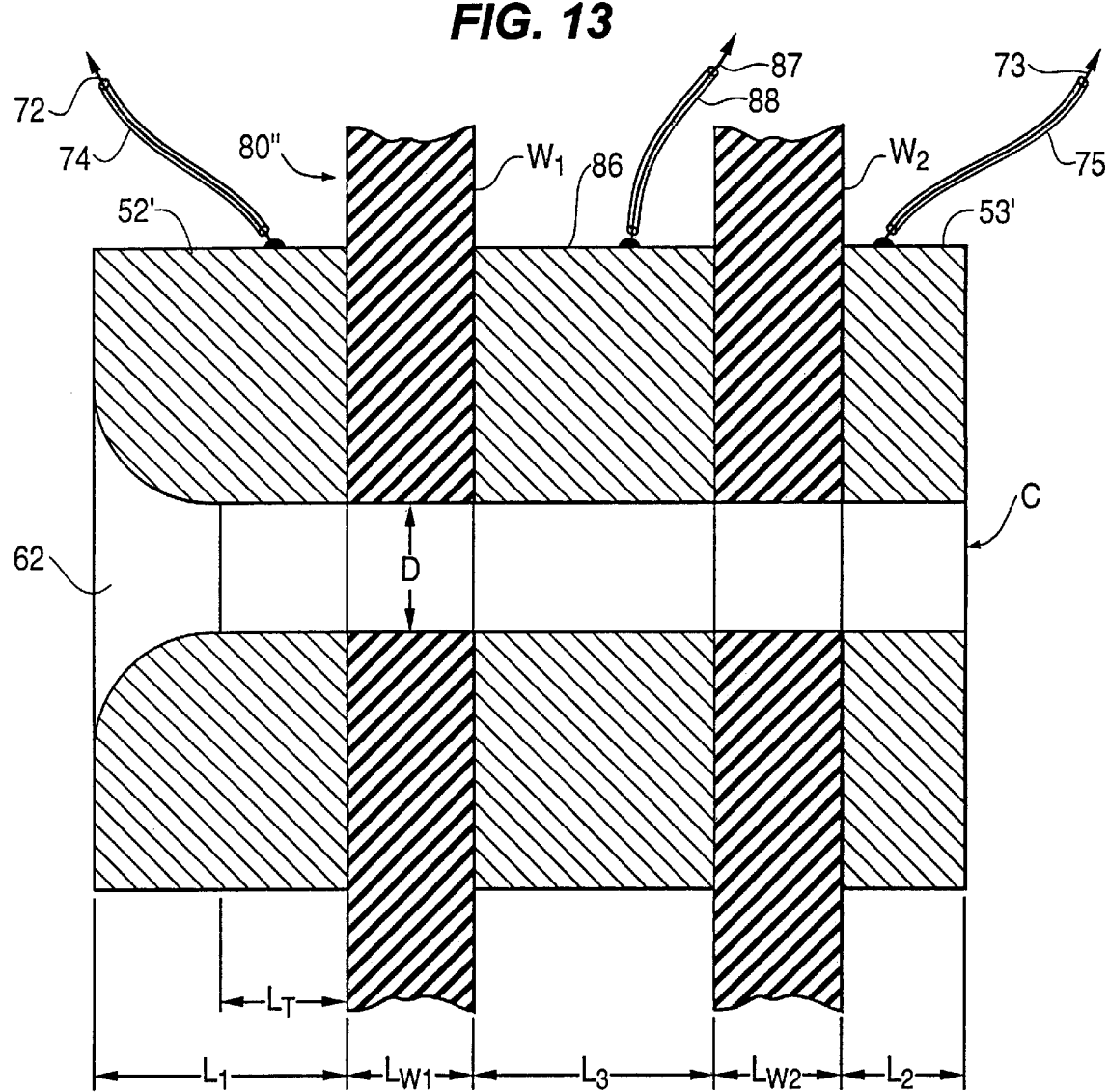
FIG. 13 illustrates a longitudinal section of a field-amending conduit structure, adapted from the FIG. 11 structure to use in the apparatus of FIG. 6B.

In FIG. 13 is illustrated a volumeter assembly 80" in which Embodiment 6 is appropriately extended by the addition of a suitable pair of elements consisting of a second Coulter wafer $W_2$ and field-amending collar 86, to which insulated (88) electrically conductive path 87 is provided. Volumeter assembly 80" thus comprises two Coulter wafers $W_1$ and $W_2$ to each of which is fixed a respective field-amending collar 52' or 53' and the two of which are separated by field-amending element 86 of a suitable conductive material. Materials of the individual elements may be any appropriate to the application. It is generally preferable that the several field-amending collars 52', 86, and 53' be of the same conductive material.

The respective axial extents $L_{w1}$ and $L_{w2}$ of the two Coulter wafers $W_1$ and $W_2$ are not required to be equal, but are preferred to be between 0.3 and 2.5 times the diameter D of conduit C. The axial extents $L_1$ and $L_2$ of respective collars 52' and 53' are selected as for preceding embodiments and are preferred to be between one and four times the diameter D of conduit C. The axial extent $L_3$ of collar 86 is preferred to be one to two times the diameter D of conduit C, but timing or other considerations may require $L_3$ to be several times the conduit diameter D.

Shaped conduit entry 62 may be beneficial in demanding applications and may take any of the variations discussed in Embodiment 6; in general, $L_T \geq D$. The needs of many applications, however, can be met by flat collars (i.e., collars of the form of 53' or 86 may be substituted for shaped-entry collar 52'), and this form is preferred for ease of manufacture.

Volumeter assembly 80" may be assembled by joining two subassemblies, one made according to Embodiment 4 (e.g., field-amending collar 52'; Coulter wafer W., and collar 86) and the other made according to Embodiment 9 (e.g., Coulter wafer $W_2$ and field-amending collar 53'). Many practical difficulties in fabrication can be avoided through the use of undersize conduits in the two subassemblies and an appropriate wire to align the two conduits during assembly, with finishing of conduit C in the complete volumeter assembly to its final diameter D as described in Embodiment 4. Electrically conductive paths 72, 87, and 73 to the respective field-amending collars 52', 86, or 53' may be provided by small insulated wires connected (e.g., with conductive paint or epoxy) to the outer diameters of said collars, as shown in FIG. 13; the electrical junctions may be insulated and protected by beading in the angle between each Coulter wafer $W_2$ or $W_2$ and said collars with an appropriate insulative epoxy (not shown).

It is also possible to assemble in the aforementioned manner two subassemblies made according to Embodiment 9 (e.g., Coulter wafer $W_1$ and field-amending collar 86; Coulter wafer $W_2$ and field-amending collar 53'), so that a less-preferred volumeter assembly 80''' comprises equal numbers of field-amending elements and Coulter wafers, but with the limitations discussed in connection with the latter embodiment.

EMBODIMENT 20

According to another embodiment, a flow cell of the type described in Embodiment 8 is provided additional sensitive zones as described in Embodiment 10. Thus, in FIG. 12 an appropriate subassembly according to Embodiment 9 (Coulter wafer $W_1$ and field-amending collar 52' or similar pair $W_2$ and 53') is positioned with the aid of an alignment wire over both openings of conduit C (i.e., the entry opening of collar 52' and the exit opening of collar 53' of flow cell 65), with the Coulter wafer $W_1$ or $W_2$ of each respective subassembly against field-amending collar 52' or 53' of volumeter assembly 50'.

Figure 14:
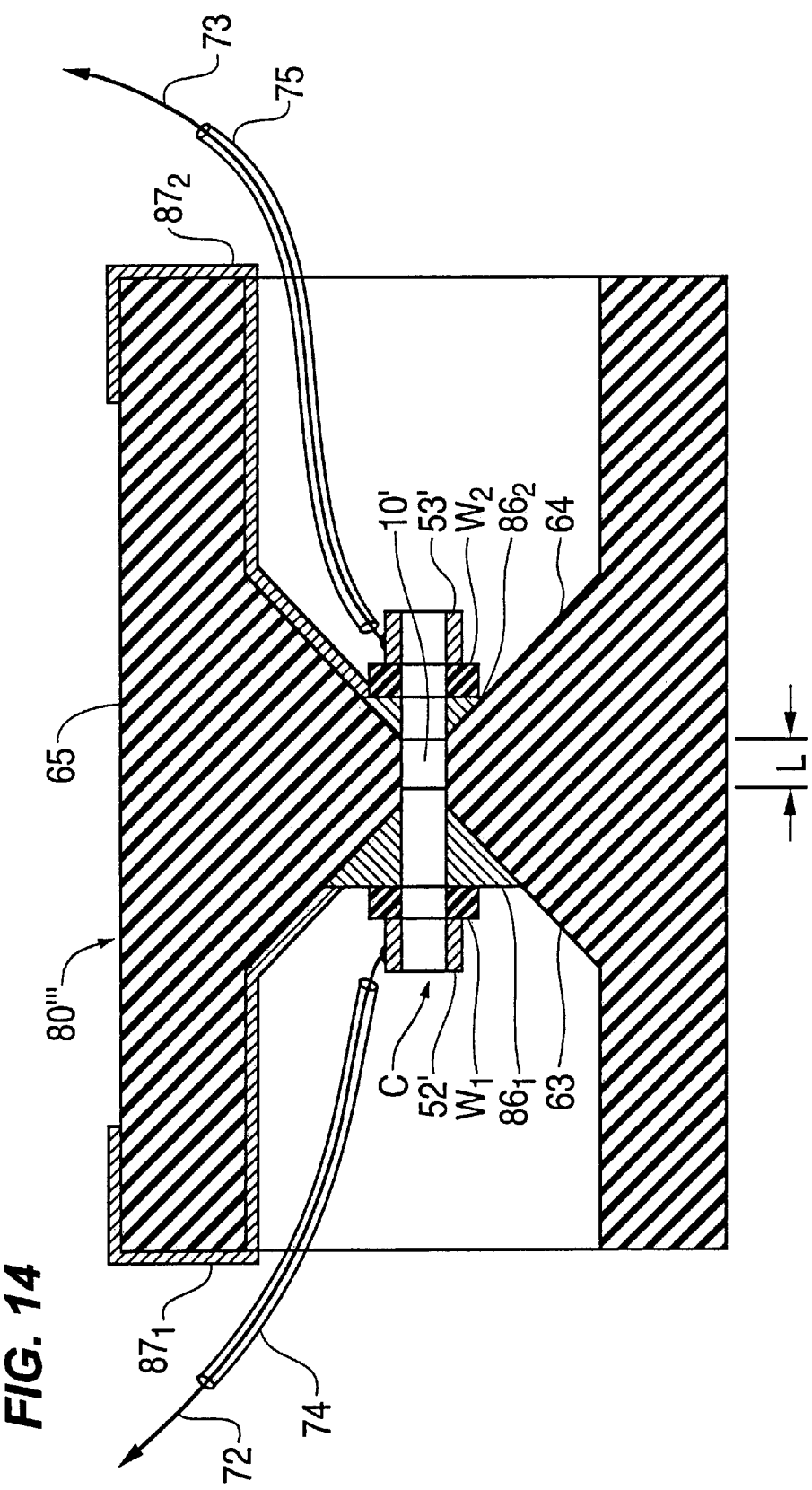
FIG. 14 illustrates a longitudinal section of a field-amending conduit structure, adapted from the FIG. 12 structure to use in the apparatus of FIG. 6B.

Thus, external field-amending collars of the FIG. 12 structure are converted into internal ones in the resulting FIG. 14 structure, wherein field-amending collars $86_1$ and $86_2$ (with respective electrically conductive paths $87_1$ and $87_2$ thereto) correspond to FIG. 12 field-amending collars 52' and 53' (with respective electrically conductive paths 72 and 73 thereto). The axial extents of field-amending collars $86_1$ and $86_2$ may be chosen according to the needs of the application, but are preferred to be in the range between one and four times the diameter D of conduit C.

It is preferred that said subassemblies ($W_1$ and 52' or $W_2$ and 53') comprise electrically conductive paths 72 and 73 to respective field-amending elements 52' or 53'. Conductive paths 72 and 73 may comprise small insulated wires, as shown in FIG. 14, but may more preferably be metallic lands deposited on the surface of the dielectric elements shown in the figure, i.e., similar to conductive paths $87_1$ and $87_2$. Preferably each said subassembly is sealed into position with insulative epoxy (not shown in FIG. 14). Care should be taken to insulate appropriate portions of respective electrically conductive path 72 or 73 and field-amending collars 52' and 53', as well as to fill in regions around the subassemblies likely to cause zones of stagnant flow. Electrically conductive paths 72 and 73 and insulation thereof should be arranged with regard to any fluidic or optical interference. Once the epoxy has cured, the alignment wire is removed and composite conduit C polished, to ensure hydrodynamic smoothness within the conduit and proper electrical contact of the field-amending collars with suspending medium M. In this form volumeter assembly 80''' is provided two additional sensitive zones, one on either side of the original one between field-amending collars $86_1$ and $86_2$. It is not required than Coulter wafer(s) W have the same axial extent L as the conduit 10' through flow cell 65.

In other forms, the volumeter assembly is provided only a second sensitive zone, formed either between either field-amending collar $86_1$ or $86_2$ in FIG. 14 and field-amending collar 52' or 53' of the added subassembly.

With reference now to FIGS. 6B, 13, and 14 and with the aforesaid stipulations in mind, in implementations of the second type of apparatus according to the invention, via the respective electrically conductive path (72; $87_1$ ..., or $87_{(n-1)}$; 73) provided to field-amending elements (52'; $86_1$ ..., or $86_{(n-1)}$; 53'), either at least one input $18_1$ or $18_2$ of one sensing circuitry 18 or at least one output $29_1$ or $29_2$ of one effector current source 29 is operatively connected to at least one field-amending element in volumeter assembly 80 having more than one sensitive zone. The other said input of sensing circuitry 18 or output of effector current source 29 may be operatively connected in a corresponding manner to any other such field-amending element of volumeter assembly 80 or to a discrete electrode (e.g., 15 or 16; auxiliary discrete electrodes such as $A_1$ or $A_2$ of FIG. 6A may also be used, but are not shown in FIG. 6B). These general comments illustrate the further variety of apparatus possible according to the invention. Possible connection modes for said inputs of one sensing circuitry 18 or outputs of one effector current source 29 are summarized in Table 1 for a single sensitive zone according to the invention; in implementations of the second type, any of the six possible connections for a sensing circuitry (18 or 18') or a current source (29 or 29') may be independently made in the aforesaid manner to any of the plural sensitive zones in volumeter assembly 80. As with volumeter assemblies comprising a single sensitive zone, some such connections to volumeter assemblies 80 comprising multiple sensitive zones are preferable to others. Generally, those connection modes are less preferable which require either sensing or passage of effector current between any electrode pair including more than one sensitive zone. Multiple sensing circuitry 18 or 18' (or effector current sources 29 or 29') may also be used, to provide multiple simultaneous connections to various combinations of electrodes according to desired operational properties.

In the second illustrative apparatus shown in FIG. 6B, volumeter assembly 80" is one of the volumeter assemblies having double sensitive zones in Embodiments 19 or 20, and inputs 18$_1$ and 18$_2$ of a first sensing circuitry 18$_A$ are operatively connected (via electrically conductive paths 72 and 87) to field-amending elements 52' and 86 thereof. By means of two-position, two pole switch S$_2$, field-amending elements 86 and 53' of volumeter assembly 80" may be operatively connected (via electrically conductive paths 87 and 73) to either inputs 18$_1$ and 18$_2$ of a second sensing circuitry 18$_B$ or outputs 29$_1$ and 29$_2$ of effector source 29. Some preferred configurations based on this illustrative apparatus are discussed in Embodiments 21 through 24.

EMBODIMENT 21

In one example, in FIG. 6B switch S$_2$ is in Position 1, whereby field-amending elements 86 and 53' of volumeter assembly 80" are operatively connected (via electrically conductive paths 87 and 73) to inputs 18$_1$ and 18$_2$ of a second sensing circuitry 18$_B$. Effector current source 29 is not required. Volumeter assembly 80" comprises Coulter wafers W$_1$ and W$_2$ having the same thickness and conduit diameter (D=0.100 mm and L$_1$/D=L$_2$/D=1.2), and pulse characteristics from sensing circuitry 18$_A$ and 18$_B$ for identical particles are substantially identical. For well-constructed volumeter assemblies 80", the differences in volumetric distributions for particles small relative to diameter D of conduit C indicate the degree to which laminarity has developed in the two tandem sensitive zones. Such volumeter assemblies 80" provide improved volumetric capability from both sensitive zones and avoid need for the fluidic complexity associated with prior-art sequential discrete conduits (e.g., aforementioned U.S. Pat. Nos. 3,793, 587 or 4,525,666). In addition, correlation of pulses in the two pulse streams to a given particle is possible with simpler methods and greater confidence than for prior-art apparatus (viz., aforementioned U.S. Pat. No. 4,184,766). The scientific study of differences in volumetric distributions due to particle mass or density, as a function of the length of field-amending element 86, promises to be a fruitful application of apparatus according to this embodiment.

With apparatus of this configuration, it is useful to know whether a given signal from sensing circuitry 18$_A$ and 18$_B$ is actual or artifactual, i.e., whether electrically conductive path 87 to volumeter assembly 80" has been damaged. A third sensing circuitry 18$_C$ incorporating a differentiator circuit appropriate to pulse characteristics can be helpful in this regard, if it is operatively connected (as indicated by the narrowed connective in FIG. 6B) to discrete electrodes 16 and 17. Specifically, due to electric-field gradients within field-amending element 86, an appropriate differentiator circuit (or a high-pass filter with appropriate time constant) operating on he pulse signal sensed between either of the said electrode pairs can separate the composite signal originating in the combined tandem conduit C into the portion s originating in the first and second sensitive zones thereof. The connection of sensing circuitry 18C to discrete electrodes 15 and 16 is functionally equivalent to the apparatus of the related application in which a tandem volumeter conduit 80", according to Embodiment 10 but lacking electrically conductive paths (i.e., 72, 87, and 73), is substituted for volumeter assembly 50 of FIG. 5. A similar result can be achieved by similarly processing the composite pulse provided via electrically conductive paths 72 and 73 to field-amending elements 52' band 53'.

EMBODIMENT 22

In a second example of the same operative mode, the FIG. 68 apparatus is of the same configuration as in Embodiment 21, but in volumeter assembly 80" Coulter wafer W$_2$ surrounding the second sensitive zone is thinner than W$_1$, say, L$_1$/D=1.2 and L$_2$/D=0.3. As would be expected from the poor electric-field development in such a short conduit, pulse amplitudes are reduced. If, however, the gain of second sensing circuitry 18$_B$ is appropriately adjusted to compensate for the reduced signal amplitude, so that comparable pulse amplitudes are provided by sensing circuitry 18$_A$ and 18$_B$, the second sensitive zone of conduit C is somewhat more responsive to the spatial distribution of particle mass, viz., the pulse characteristics become more responsive to either length or cross-sectional area of the particles. Thus, taken together, two time-sequential pulse signals from the same particle can provide more than purely volumetric information, by which useful insight on particle shape may be obtained.

Such approaches are likely to provide new methods of particle characterization, valuable in both the scientific and commercial senses. Some forms of such approaches are taught for sequential discrete conduits in aforementioned U.S. Pat. No. 3,793,587, but the fluidic and correlational complexity required to implement such apparatus has prevented practical development Further, the prior-art approaches are based on making the diameter of the second discrete conduit different, preferably smaller, than that of the first conduit, with the disadvantageous effect of requiring different flow volumes through the two conduits and considerable complexity in the flow subsystems. The integrated tandem-conduit of the present invention solves many of the aforementioned implementational problems which have heretofore prevented the development and application of the desired apparatus and methods. Voluameter assemblies 80" made according to Embodiment 19 can be designed in a wide variety of practical length-to-diameter ratios L/D for each functional Coulter conduit in conduit C and made by improved techniques known to those skilled in the art of making Coulter wafers.

EMBODIMENT 23

In a second operative mode based on Embodiment 21, volumeter assembly 80" comprises Coulter wafers W$_1$ and W$_2$ having the same geometry, and switch S$_2$ in FIG. 6B is in Position 2, whereby effector current source 29 replaces sensing circuitry 18$_B$ in the operative connection to field-amending elements 86 and 53'. Current source 29 is operatively connected to an appropriate portion of sensing circuitry 18$_A$ as indicated in FIG. 6B, e.g., via a correlation or timing circuit. Thus, a particle generating a pulse during its passage through the sensitive zone defined by the geometric conduit in W$_1$ may be exposed to a particular field intensity in the sensitive zone defined by the geometric conduit in W$_2$. The activation signal from sensing circuitry 18$_A$ can be made contingent on a desired particle characteristic, for instance volume or opacity, as known in the art. The current waveform from effector source 29 may be, e.g., a pulse temporally short compared to the transit time of the particle through the W$_2$ portion of conduit C. In this configuration of the FIG. 6B apparatus, it may be beneficial to make electrically conductive path 87 a ground reference, whether by a direct connection, a virtual connection, or other operative connection. An example of the latter is a high-grade capacitor of large value connected between electrically conductive path 87 and a reference ground.

In an alternative form of the present embodiment, current source 29 is made responsive to such activation signal, whereby the current through conduit C between field-amending elements 86 and 53' is increased above the nominal excitation current in a desired manner, e.g., either in a step mode or in a continuous ramping mode. In this configuration of the FIG. 6B apparatus, it may be beneficial to make either or both field-amending element 86 and $W_2$ axially longer than the preferred minimum, to provide a time delay, e.g., to permit transients to decay or to allow effector source 29 sufficient time to modify the field within the second sensitive zone.

Such forms of the new apparatus may be used to determine membrane breakdown or cell fragility as known in the biological-cell art. These approaches are important in many scientific areas related to biological problems of clinical interest, and some are discussed in aforementioned U.S. Pat. No. 4,525,666. However, the aforementioned fluidic and correlational complexity required to implement the sequential discrete conduits in the prior-art apparatus has prevented practical development. The integrated tandem-conduit of the present invention solves many of the implementational problems which have heretofore prevented the development and application of the desired apparatus and methods.

EMBODIMENT 24

Through use of volumeter structures similar to those discussed in Embodiments 8 and 20, apparatus incorporating combined Coulter and optical sensing methods may benefit in a straightforward manner from many of the apparatus configurations suggested by respective Embodiments 10 through 17 and 21 through 23. In Embodiments 21 through 23, the two sensitive zones were sequentially adjacent in volumeter assembly 80''', i.e., shared a common field-amending element 86, but this is not necessary. A novel embodiment comprising a volumeter assembly 80 according to Embodiment 20 will provide an example. This embodiment is not illustrated in FIGS. 6, 6A, or 6B, but is an elaborated functional analogy of the FIG. 6B configuration described in Embodiment 21, wherein sensing circuitry $18_A$ and $18_B$ share no common connection (i.e., conductive path 87). In the following, general reference is made to FIG. 6B (in which for present purposes switch $S_2$ should be ignored), for input designations of sensing circuitry $18_A$, $18_B$, and $18_C$ and output designations of current source 29; similar reference is made to FIG. 14 for designations of field-amending elements of volumeter assembly 80''' and conductive paths thereto.

Let volumeter assembly 80''' of FIG. 14 be substituted for corresponding assembly 80'' in FIG. 6B. Let inputs $18_1$ and $18_2$ of sensing circuitry $18_A$ of FIG. 6B then be operatively connected to field-amending elements 52' and $86_1$, respectively, of FIG. 14 volumeter assembly 80'''; and let inputs $18_1$ and $18_2$ of sensing circuitry $18_B$ of FIG. 6B then be operatively connected to field-amending elements $86_2$ and 53', respectively, of said volumeter assembly 80'''. Then let a suitable pulsed-laser source be operatively connected via appropriate timing or correlation means to sensing circuitry $18_A$ in lieu of current source 29 shown in FIG. 14 so that said laser source may be activated in response to a particle characteristic processed thereby. With this configuration, a particle transiting conduit C of volumeter assembly 80''' generates a pulse on passing through the portions of the conduit surrounded by both Coulter wafers $W_1$ and $W_2$. Thus, a comparison of pulses generated by the same particle in the two non-adjacent sensitive zones may be used to determine whether a significant change in particle volumetric characteristics occurred in conduit section 10' comprised in the original sensitive zone of the FIG. 12 volumeter assembly 80', viz., whether a laser pulse coupled through the transparent wall of flow cell 65 had caused disruption of a biological cell in response to cell characteristics sensed in the sensitive zone defined by Coulter wafer $W_1$. The forms of volumeter assembly 80 described in Embodiment 20 enable a form of Coulter apparatus wherein the intensity of the electric field in a second sensitive zone may be drastically increased by photonic means without introduction of appreciable artifact in the volumetric data produced in an adjacent sensitive zone.

A similar end result might be obtained if a pulse source 29 of FIG. 6B, operatively connected to both sensing circuitry $86_A$ as has been described and FIG. 14 field-amending elements $86_1$ and $86_2$ via conductive paths $87_1$ and $87_2$ thereto, were activated to disrupt the cell in analogy to Embodiment 15. In applications such as these the diameter D of conduit C would typically be in the range between 0.050 and 0.100 mm, with L/D≈1, so that the time intervals between the first (evaluation) pulse from the first sensitive zone and the second (confirmation) pulse from the second one is of the order of 10 microseconds. Laser pulses can readily be delivered in this time interval, and pulsed-laser sources have the double advantage of substantially avoiding disturbances in the nominal electric field in the conduit and of being unlimited by the transient response of electrodes immersed in suspending medium M. It is much more difficult to effectively pulse the nominal electric field so quickly, recovery times are longer, and required conduit lengths may become excessive. Laser sources are more costly and complex than electronic pulse sources, but in some Coulter apparatus also incorporating optical sensing modalities, an appropriate laser may already be present for other purposes. In critical applications the cost and complexity of adding a laser to implement such cell-by-cell disruption may be a cost-efficient solution.

In another configuration, inputs $18_1$ and $18_2$ of sensing circuitry $18_C$ might be connected to excitation discrete electrodes 15 and 16, as indicated by the narrowed connectives in FIG. 6B, and provided a differentiator circuit appropriate to pulse characteristics as described in Embodiment 21. Due to electric-field gradients within field-amending element 86, an appropriate differentiator circuit operating on the pulse signal sensed between the said electrodes can separate the composite pulse originating in tandem conduit C into the portions originating in each of the treble sensitive zones thereof. The derivative signals may be used to activate gating circuitry according to a desired portion of the composite pulse or as a monitor of, e.g., conduit cleanliness.

Alternatively, inputs $18_1$ and $18_2$ of sensing circuitry $18_C$ might be connected to field-amending elements $86_1$ and $86_2$ via conductive paths $87_1$ and $87_2$ thereto, whereby a third individual particle pulse could be provided.

The axial extents of the various elements of the FIG. 14 volumeter assembly 80''' may be optimized as is known in the art according to the particular implementation being considered. In any embodiment according to the invention, field-amending elements incorporated in the structure comprising conduit C provide the advantages of the related application.

EMBODIMENT 25

Due to its greater length conduit C of volumeter assembly 50' in FIG. 6 or 80" in FIGS. 6A and 6B may be more prone to clogging than is traditional Coulter conduit 10 of FIG. 1. However, the smaller coincidence volume afforded by the field-amending elements allows use of larger diameters (for comparable coincidence rates and axial extents of the sensitive zones) than with the prior-art volumeter conduit. Although this favors reduced clogging rates, clogging may pose a problem, particularly with samples of biological origin. For this reason, the cleaning method of Embodiment 16 is important, since sensing circuitry 18 can be designed to activate an appropriate source 29 to remove debris buildup, often before complete clogging of conduit C occurs. However, other methods have proven beneficial for Coulter apparatus comprising the traditional Coulter conduit.

Duplication of the '508 apparatus incorporating Coulter conduit 10 of FIG. 1 into a compound multi-channel apparatus has been discussed in connection with considerations originating in sample characteristics, and while similar four-terminal apparatus is unknown, the volumeter conduits of FIGS. 7 through 13 may be similarly adapted in straight-forward manner to parallel-conduit use. For example, such systems would comprise a single entry compartment containing a first discrete electrode, but provide each volumeter assembly 80 with an electrically isolated exit compartment containing an individual second discrete electrode connected to an individual current source 17, with all conduits C being simultaneously transited by particle streams split from the sample suspension in the entry compartment. Through appropriate electrical connections to its field-amending elements and sensing circuitry 18 connected thereto, each conduit C would independently generate pulse data for the particles in its portion of the split sample. As taught in aforementioned U.S. Pat. Nos. 3,444,463 and 3,603,875 to Wallace H. Coulter and W. R. Hogg, the several parallel conduits could be of either identical geometry or dissimilar geometry. In the first case voting logic would eliminate from the redundant data streams any data originating in a clogged conduit, while for polydisperse samples, pulse-analytic circuitry in the second would combine the dissimilar data streams into a composite volumetric distribution. The complexity of such four-terminal parallel systems makes them less desirable than in the two-terminal case, but critical applications may justify their use.

Many other forms of apparatus comprising prior-art volumeter conduits are known. Numerous other combinations of sensing circuitry 18, sources 29, and electrical connections to field-amending elements within volumeter assemblies 80 adapted from those described in the related application will occur to those skilled in the Coulter art of sensing and characterizing particles. However, it is believed that the concepts of the invention are sufficiently defined, and their range of applicability sufficiently indicated, that their potential, versatility, and advantages to practical apparatus may be appreciated. Moreover, it is believed that the embodiments herein described will enable one skilled in the Coulter arts to design practicable apparatus incorporating the concepts of the invention.

None of the aforesaid prior-art apparatus comprise field-amending volumeter assembly 50' and conduit C therein. Consequently, regardless of configurational similarity to prior-art apparatus, apparatus of the invention offers numerous significant functional and commercial advantages, as described in the related application. Although volumeter assembly 50' may resemble ones described in U.S. Pat. Nos. 3,924,180 and 4,438,390, it is distinguished from such prior art due to the unique functional characteristics provided by conduit C. Similarly, although in configuration the apparatus of FIGS. 6, 6A, and 6B may variously resemble apparatus described in certain prior art, in comprising volumeter assembly 50' it is distinguished from such prior art. Regardless of the particular configuration of any given prior-art apparatus, none offers the particular, significant, and broad advantages taught in the related application.

Uses of the numerous embodiments, and methods whereby they may be implemented, are only indicated in outline form, for two reasons. Firstly, one skilled in the art of using present Coulter apparatus will be able to apply the apparatus of the invention with minimal experimentation. Secondly, it is believed that some of the uses and methods to which apparatus of the invention may be adapted have yet to be realized, being for one or another reason beyond the capabilities of present apparatus.

In the above description, the advance which the invention represents will become apparent to those skilled in this art, and while theories are expressed as an aid to explanation, these are not intended to be limiting, irrespective of their degree of correctness.

What is claimed is:

1. Apparatus for sensing and characterizing particles by the Coulter principle, said apparatus comprising:

(a) a volumeter conduit through which a liquid suspension of particles to be sensed and characterized can be made to pass, said volunteer conduit being hydrodynamically smooth and formed in a solid member having an electrical resistivity which effectively varies along the conduit length to define a conduit having at least one delimited region of high electrical resistivity, each said delimited region being smoothly contiguous on at least one of its opposing boundaries to an uninsulated region of substantially lesser electrical resistivity;

(b) a liquid handling-system for causing said liquid suspension of particles to pass through said volumeter conduit;

(c) a first electrical circuit for producing a first nominal electrical current through said volumeter conduit, said first nominal electrical current being effective to establish in the vicinity of said volumeter conduit an electric field having at least one particle-sensitive zone in which changes in said first nominal electrical current as produced by particles passing through said volumeter conduit simultaneously with said first nominal current are measurable, said uninsulated region having a length measured along the longitudinal axis of said conduit which is sufficient to independently (i) shape said electric field in the vicinity of said uninsulated region so as to substantially confine a substantial portion of said particle-sensitive zone within the physical boundaries of the conduit; and (ii) either enable development of quasi-laminar flow through said particle-sensitive zone so as to increase the proportion of particles per second transiting substantially homogeneous areas of said particle-sensitive zone, or prevent particles that have already passed through said conduit and are on recirculating trajectories from re-entering said particle-sensitive zone; and (d) at least one second electrical circuit operatively connected to at least one said uninsulated region of said volumeter conduit, said second electrical circuit functioning to monitor the characteristics of said electrical current to or through at least a portion of said volumeter conduit to detect the presence or sense the characteristics of particles passing through said conduit.

2. The apparatus as defined by claim 1 wherein at least one of said second electrical circuits is connected between a pair of said uninsulated regions of said volumeter conduit.

3. The apparatus as defined by claim 1 wherein said solid member is a multiple-element structure composed of at least one layer of material having high electrical resistivity disposed adjacent to, and contiguous with, at least one layer of material of lesser resistivity, and wherein said conduit is formed by through-holes respectively formed in each of said layers, said through-holes being of the same size and shape and being fluidically aligned to form a hydrodynamically continuous and smooth conduit passing through said three-element structure.

4. The apparatus as defined by claim 1 wherein said solid member comprises at least one intrinsic semiconductor wafer which is suitably doped with an electrically active impurity to provide each said delimited region of high electrical resistivity, each said delimited region being smoothly contiguous on at least one of its opposing boundaries to an uninsulated region of substantially lesser electrical resistivity.

5. The apparatus as defined by claim 1 wherein said solid member comprises a unitary assembly comprising at least one set of two complementary and contiguous ceramic elements, one ceramic element of each set being substantially pure and the other ceramic element of each set being either a conductive ceramic or a ceramic infiltrated with a metallic material to enhance the conductivity thereof, and wherein said conduit is formed by through-holes respectively formed in each of said ceramic elements, said through-holes being of the same size and shape and being fluidically aligned to form said hydrodynamically smooth conduit.

6. The apparatus as defined by claim 1 wherein said solid member comprises a unitary assembly comprising at least one set of two complementary and contiguous elements, one element being made of a substantially pure ceramic and the other element being made of a metallic material, and wherein said conduit is formed by through-holes respectively formed in each of said elements, said through-holes being of the same size and shape and being fluidically aligned to form said hydrodynamically smooth conduit.

7. The apparatus as defined by claim 1 wherein said volumeter assembly comprises a flow cell having a wall of dielectric material which defines one said delimited region of said conduit and at least one conductive collar the uninsulated through-hole of which defines said region of lesser resistivity.

8. The apparatus as defined by claim 1 wherein a through-hole formed in one of said uninsulated regions gradually increases in diameter to provide a trumpet-shaped or radiussed opening through which a particle suspension can readily enter said conduit.

9. The apparatus as defined by claim 1 wherein said volumeter conduit has a circular cross-section.

10. The apparatus as defined by claim 1 wherein said volumeter conduit has a rectangular cross-section.

11. The apparatus as defined by claim 1 wherein said volumeter conduit is defined by (a) a through-hole formed in at least one wafer of dielectric material, and (b) a central opening formed in at least one electrically-conductive collar, said central openings and said through-hole being of identical size and shape, said collar being disposed on one side of said wafer so that the said opening and said through-hole collectively form a hydrodynamically smooth conduit.

12. The apparatus as defined by claim 11 wherein said volumeter conduit has a circular cross-section, and wherein each of said collars is circular in shape and has a thickness approximately 1 to 10 times the thickness of said wafer.

13. The apparatus as defined by claim 11 wherein each of said collars comprises a material selected from the group consisting of metals of the platinum group, gold, nickel, tungsten, titanium, alloys of said metals, silicon carbide, titanium carbide, and tungsten carbide.

14. The apparatus as defined by claim 11 wherein at least the central openings of said collars are plated with a metallic material selected from the group consisting of metals of the platinum group, gold, nickel, tungsten, titanium, alloys of said metals, silicon carbide, titanium carbide, and tungsten carbide.

15. The apparatus as defined by claim 11 wherein each of said collars comprise a material selected from the group consisting of sapphire, ruby, alumina, quartz, glass, beryllia, silicon carbide, titanium carbide, and tungsten carbide, and wherein at least the central openings of said collars are plated with a metallic material selected from the group consisting of metals of the platinum group, gold, titanium, and alloys of such metals.

16. The apparatus as defined by claim 11 wherein the material of one said collar differs from that of any other said collar.

17. The apparatus as defined by claim 11 wherein at least one said collar constitutes a structural component of said liquid-handling system.

18. The apparatus as defined by claim 11 wherein said collars have substantially the same thickness.

19. The apparatus as defined by claim 11 wherein the thickness of one said collar differs from that of any other said collar.

20. The apparatus as defined by claim 11 wherein each of said wafers comprises a material selected from the group consisting of sapphire, ruby, alumina, quartz, glass, beryllia, and lossy dielectrics.

21. Apparatus for sensing and characterizing particles by the Coulter principle, said apparatus comprising:

(a) a volumeter conduit through which a liquid suspension of particles to be sensed and characterized can be made to pass, said volumeter conduit being hydrodynamically smooth and formed in a solid member having an electrical resistivity which effectively varies along the conduit length to define a conduit having at least one delimited region of high electrical resistivity, each said delimited region being smoothly contiguous on at least one of its opposing boundaries to an uninsulated region of substantially lesser electrical resistivity;

(b) a liquid handling-system for causing said liquid suspension of particles to pass through said volumeter conduit;

(c) a first electrical circuit for producing a first nominal electrical current through said volumeter conduit, said first nominal electrical current being effective to establish in the vicinity of said volumeter conduit an electric field having at least one particle-sensitive zone in which changes in said first nominal electrical current as produced by particles passing through said volumeter conduit simultaneously with said first nominal current are measurable, said uninsulated region having a length measured along the longitudinal axis of said conduit which is sufficient to independently (i) shape said electric field in the vicinity of said uninsulated region so as to substantially confine a substantial portion of said particle-sensitive zone within the physical boundaries of the conduit; and (ii) either enable development of quasi-laminar flow through said particle-sensitive zone so as to increase the proportion of particles per second transiting substantially homogeneous areas of said particle-sensitive zone, or prevent particles that have already passed through said conduit and are on recirculating trajectories from re-entering said particle-sensitive zone;

(d) at least one second electrical circuit functioning to monitor the characteristics of said electrical current to or through at least a portion of said volumeter conduit to detect the presence or sense the characteristics of particles passing through said conduit; and (e) a third electrical circuit for producing a nominal electrical effector current through at least a portion of said volumeter conduit, each effector current being effective to establish in the vicinity of each said portion an electric field having a field intensity different from that established in each said particle-sensitive zone by said first electrical circuit, said third electrical circuit being operatively connected to at least one of said uninsulated regions of said volumeter conduit.

22. The apparatus as defined by claim 21 wherein said effector current is responsive to an aspect of said particle characteristic sensed by said second electrical circuit.

23. The apparatus as defined by claim 21 wherein at least one said second electrical circuit is connected between a pair of discrete electrodes by which said first electrical circuit produces a first nominal electrical current through said volumeter conduit.

24. The apparatus as defined by claim 21 wherein at least one said second electrical circuit is connected between an uninsulated region of said volumeter conduit and either (a) one of a pair of discrete electrodes by which said first electrical circuit produces a first nominal electrical current through said volumeter conduit, or (b) an auxiliary electrode immersed in said suspension.

25. The apparatus as defined by claim 21 wherein said second electrical circuit is connected between a pair of said uninsulated regions of said volumeter conduit.

26. The apparatus as defined by claim 21 wherein said solid member is a multiple-element structure composed of at least one layer of material having high electrical resistivity disposed adjacent to, and contiguous with, at least one layer of material of lesser resistivity, and wherein said conduit is formed by through-holes respectively formed in each of said layers, said through-holes being of the same size and shape and being fluidically aligned to form a hydrodynamically continuous and smooth conduit passing through said three-element structure.

27. The apparatus as defined by claim 21 wherein said solid member comprises at least one intrinsic semiconductor wafer which is suitably doped with an electrically active impurity to provide each said delimited region of high electrical resistivity, each said delimited region being smoothly contiguous on at least one of its opposing boundaries to an uninsulated region of substantially lesser electrical resistivity.

28. The apparatus as defined by claim 21 wherein said solid member comprises a unitary assembly comprising at least one set of two complementary and contiguous ceramic elements, one ceramic element of each set being substantially pure and the other ceramic element of each set being either a conductive ceramic or a ceramic infiltrated with a metallic material to enhance the conductivity thereof, and wherein said conduit is formed by through-holes respectively formed in each of said ceramic elements, said through-holes being of the same size and shape and being fluidically aligned to form said hydrodynamically smooth conduit.

29. The apparatus as defined by claim 21 wherein said solid member comprises a unitary assembly comprising at least one set of two complementary and contiguous elements, one element being made of a substantially pure ceramic and the other element being made of a metallic material, and wherein said conduit is formed by through-holes respectively formed in each of said elements, said through-holes being of the same size and shape and being fluidically aligned to form said hydrodynamically smooth conduit.

30. The apparatus as defined by claim 21 wherein said volumeter assembly comprises a flow cell having a wall of dielectric material which defines one said delimited region of said conduit and at least one conductive collar the uninsulated through-hole of which defines said region of lesser resistivity.

31. The apparatus as defined by claim 21 wherein a through-hole formed in one of said uninsulated regions gradually increases in diameter to provide a trumpet-shaped or radiussed opening through which a particle suspension can readily enter said conduit.

32. The apparatus as defined by claim 21 wherein said volumeter conduit has a circular cross-section.

33. The apparatus as defined by said 21 wherein said volumeter conduit has a rectangular cross-section.

34. The apparatus as defined by claim 21 wherein said volumeter conduit is defined by (a) a through-hole formed in at least one wafer of dielectric material, and (b) a central opening formed in at least one electrically-conductive collar, said central openings and said through-hole being of identical size and shape, said collar being disposed on one side of said wafer so that the said opening and said through-hole collectively form a hydrodynamically smooth conduit.

35. The apparatus as defined by claim 34 wherein said volumeter conduit has a circular cross-section, and wherein each of said collars is circular in shape and has a thickness approximately 1 to 10 times the thickness of said wafer.

36. The apparatus as defined by claim 34 wherein each of said collars comprises a material selected from the group consisting of metals of the platinum group, gold, nickel, tungsten, titanium, alloys of said metals, silicon carbide, titanium carbide, and tungsten carbide.

37. The apparatus as defined by claim 34 wherein at least the central openings of said collars are plated with a metallic material selected from the group consisting of metals of the platinum group, gold, titanium, and alloys of such metals.

38. The apparatus as defined by claim 34 wherein each of said collars comprise a material selected from the group consisting of sapphire, ruby, alumina, quartz, glass, beryllia, silicon carbide, titanium carbide, and tungsten carbide, and wherein at least the central openings of said collars are plated with a metallic material selected from the group consisting of metals of the platinum group, gold, titanium, and alloys of such metals.

39. The apparatus as defined by claim 34 wherein the material of one said collar differs from that of any other said collar.

40. The apparatus as defined by claim 34 wherein at least one said collar constitutes a structural component of said liquid-handling system.

41. The apparatus as defined by claim 34 wherein said collars have substantially the same thickness.

42. The apparatus as defined by claim 34 wherein the thickness of one said collar differs from that of any other said collar.

43. The apparatus as defined by claim 34 wherein each of said wafers comprises a material selected from the group consisting of sapphire, ruby, alumina, quartz, glass, beryllia, and lossy dielectrics.

44. A method for sensing and characterizing particles by the Coulter principle, said method comprising:

(a) passing a liquid suspension of particles to be sensed and characterized through a volumeter conduit formed in a solid material having an electrical resistivity which effectively varies along the conduit length to define a conduit having at least one delimited region of high electrical resistivity which is smoothly contiguous on at least one of its opposing boundaries to an uninsulated region of substantially lesser electrical resistivity;

(b) producing a nominal electrical excitation current through said volumeter conduit and an electric field in the vicinity of said conduit, said electric field having a particle-sensitive zone in which changes in said nominal electrical excitation current as produced by particles passing through said volumeter conduit simultaneously with said nominal current are measurable, said uninsulated region independently functioning (i) to shape said electric field so as to substantially confine said sensitive zone within the physical boundaries of the conduit; and (ii) to enable development of quasi-laminar flow through said sensitive zone so as to increase the proportion of particles per second transiting substantially homogeneous areas of the sensitive zone; and (c) monitoring the amplitude of the electrical current through said volumeter conduit to sense the approach of particles to, the presence and characteristics of particles passing through, or the departure of particles from, said conduit, said monitoring step comprising the step of producing an effector electrical current through at least a portion of said liquid suspension of particles in response to said sensing of the approach of particles to, the presence or characteristics of particles passing through, or departure of particles from, said conduit; said effector electrical current functioning to modify at least a portion of said electric field in the vicinity of said conduit.

* * * * *

UNITED STATES PATENT AND TRADEMARK OFFICE
CERTIFICATE OF CORRECTION

PATENT NO.    : 6,175,227 B1
DATED         : January 16, 2001
INVENTOR(S)   : Graham, et al.

Page 1 of 4

It is certified that error appears in the above-identified patent and that said Letters Patent is hereby corrected as shown below:

Column 3,
Line 8, change "UD" to -- L/D --.
Line 20, change "parcel" to -- particle --.
Line 23, change "3,444,483" to -- 3,444,463 --.
Line 51, change "parcel" to -- particle --.
Line 65, change "feeds" to -- fields --.

Column 4,
Line 5, change "UD" to -- L/D --.
Line 50, change "Wallce" to -- Wallace --.

Column 5,
Line 47, insert a period after "conduit".

Column 6,
Line 5, insert a period after "conduit".
Line 52, change "Wallce" to -- Wallace --.

Column 10,
Line 12, change "19741" to -- 1974 --.
Line 12, change "12" to -- 12 --.
Line 24, change "27128" to -- 27/28 --.
Line 35, change "volunteer" to -- volumeter --.
Line 37, change "flow" to -- field --.

Column 12,
Line 6, change "W" to -- W' --.

Column 13,
Lines 59, 60, and 62, change "W" to -- W" --.

Column 14,
Line 2, change the second occurrence of "AT" to -- BT --.
Line 54, change "=508" to -- '508 --.

Column 18,
Line 8, change "i n" to -- in --.

Column 20,
Line 57, change "concept" to -- corncern --.

UNITED STATES PATENT AND TRADEMARK OFFICE
CERTIFICATE OF CORRECTION

PATENT NO.   : 6,175,227 B1
DATED        : January 16, 2001
INVENTOR(S)  : Graham, et al.

It is certified that error appears in the above-identified patent and that said Letters Patent is hereby corrected as shown below:

Column 22,
Line 6, change "C" to -- 50 --.
Line 18, insert -- on -- after "FIG.1".
Line 25, change "paten t" to -- patent --.
Line 31, change "discusses" to -- discussed --.

Column 24,
Line 21, change "alterable" to -- alternative --.

Column 28,
Line 16, change "61" to -- 51 --.
Line 36, change "discord" to -- discoid --.
Line 60, change "volunteer" to -- volumeter --.

Column 29,
Line 13, insert -- , -- after "titanium".
Line 15, change "cement" to -- cermet --.

Column 31,
Line 32, change "perform" to -- preform --.
Line 65, change "volunteer" to -- volumeter --.

Column 34,
Line 4, change "W." to -- W, --.
Line 25, insert -- 33 -- after "entry orifice".

Column 37,
Line 38, change "$L_T=D$" to -- $L_T = D$ --.

Column 38,
Line 33, delete the "W" before "Wallace".
Line 53, change "77" to -- $77_1$ --.

Column 39,
Line 30, change "dual nt" to -- dual-element --.

Column 42,
Lines 11 and 12, change "volunteer" to -- volumeter --.

UNITED STATES PATENT AND TRADEMARK OFFICE
CERTIFICATE OF CORRECTION

PATENT NO.   : 6,175,227 B1
DATED        : January 16, 2001
INVENTOR(S)  : Graham, et al.

It is certified that error appears in the above-identified patent and that said Letters Patent is hereby corrected as shown below:

Column 43,
Line 37, change "a8" to -- 18 --.
Line 52, change "o f" to -- of --.

Column 44,
Line 49, delete the "5" before "3,924,180".

Column 45,
Line 40, change "a not her" to -- another --
Line 43, change "path s" to -- paths --.
Line 50, change "plus" to -- pulse --.

Column 46,
Line 18, change "43161,690" to -- 4,161,690 --.
Line 30, change "t he" to -- the --.
Line 53, change "in" to -- 15 --.

Column 47,
Line 7, change "50'" to -- 80' --.
Line 54, change "volunteer" to -- volumeter --.

Column 48,
Line 2, change "discriminate" to -- discriminant --.
Line 17, change "How ever" to -- However --.
Line 34, change "Activata on" to -- Activation --.
Lines 43 and 44, change "thi s" to -- this --.

Column 49,
Line 11, insert -- a -- before "volumeter".
Line 14, insert -- n -- before "sensitive zones".
Line 67, change "86," to -- 86j --.

Column 50,
Line 13, change "high-resisfivity" to -- high-resistivity --.

Column 51,
Line 31, change "$W_.$" to -- $W_1$ --.
Line 31, change the first "$W_2$" to -- $W_1$ --.

Column 52,
Line 40, delete the period after "aforesaid".

UNITED STATES PATENT AND TRADEMARK OFFICE
CERTIFICATE OF CORRECTION

PATENT NO. : 6,175,227 B1
DATED : January 16, 2001
INVENTOR(S) : Graham, et al.

It is certified that error appears in the above-identified patent and that said Letters Patent is hereby corrected as shown below:

Column 53,
Line 56, change "narrowed connective" to -- arrowed connectives --.
Line 60, change "he" to -- the --.
Line 62, change "portion s" to -- portions --.
Line 64, change "18C" to -- $18_C$ --.

Column 54,
Line 9, change "68" to -- 6B --
Line 42, change "Voluameter" to -- Volumeter --.

Column 56,
Line 46, change "narrowed" to -- arrowed --.

Column 58,
Line 30, change "volunteer" to -- volumeter --.
Line 38, change "liquid handling-system" to -- liquid-handling system --.

Column 60,
Line 51, change "liquid handling-system" to -- liquid-handling system --.

Signed and Sealed this

Sixteenth Day of October, 2001

Attest:

*Nicholas P. Godici*

NICHOLAS P. GODICI
*Attesting Officer*    *Acting Director of the United States Patent and Trademark Office*